United States Patent
Wu

(10) Patent No.: US 10,337,019 B2
(45) Date of Patent: Jul. 2, 2019

(54) FUNGAL ARTIFICIAL CHROMOSOMES, COMPOSITIONS, METHODS AND USES THEREFOR

(71) Applicant: Intact Genomics, Inc, Saint Louis, MO (US)

(72) Inventor: Chengcang Charles Wu, Saint Louis, MO (US)

(73) Assignee: INTACT GENOMICS, INC., Saint Louis, MO (US)

( * ) Notice: Subject to any disclaimer, the term of this patent is extended or adjusted under 35 U.S.C. 154(b) by 36 days.

(21) Appl. No.: 15/143,493

(22) Filed: Apr. 29, 2016

(65) Prior Publication Data

US 2017/0211077 A1   Jul. 27, 2017

Related U.S. Application Data

(60) Provisional application No. 62/286,542, filed on Jan. 25, 2016.

(51) Int. Cl.
| | |
|---|---|
| *C12N 15/80* | (2006.01) |
| *C12N 15/52* | (2006.01) |
| *C12N 15/69* | (2006.01) |
| *C12N 15/10* | (2006.01) |

(52) U.S. Cl.
CPC ......... *C12N 15/80* (2013.01); *C12N 15/1082* (2013.01); *C12N 15/1093* (2013.01); *C12N 15/52* (2013.01); *C12N 15/69* (2013.01); *C12N 2800/20* (2013.01); *C12N 2800/70* (2013.01); *C12N 2820/002* (2013.01); *C12N 2820/10* (2013.01); *C12N 2820/55* (2013.01)

(58) Field of Classification Search
None
See application file for complete search history.

(56) References Cited

U.S. PATENT DOCUMENTS

| | | | | |
|---|---|---|---|---|
| 5,928,867 A | * | 7/1999 | den Dunnen ...... | C12N 15/1051 435/6.17 |
| 2011/0185456 A1 | * | 7/2011 | Cheikh ............... | C07K 14/415 800/312 |

OTHER PUBLICATIONS

Carvalho et al., Appl. Microbiol. Biotechn., 87:1463-1473, 2010 (Year: 2010).*
Aleksenko, A. and Clutterbuck, A., Autonomous plasmid replication in Aspergillus nidulans: AMA1 and MATE elements, J. Fungal Genet. Biol., 1997, 21, 373-387.
Aleksenko, A., et al., Multiple copies of MATE elements support autonomous plasmid replication in Aspergillus nidulans., Mol. Microbiol., 1996a, 20, 427-434.
Aleksenko, A., et al., Integrative and replicative transformation of Penicillium canescens., Curr. Genet., 1995, 28, 474-477.
Aleksenko, A., et al., Gene expression from replicating plasmids in Aspergillus nidulans., Mol. Gen. Genet., 1996b, 253, 242-246.
Bird, D. and Bradshaw, R., Gene targeting is locus dependent in the filamentous fungus Aspergillus nidulans., Mol. Gen. Genet., 1997, 255, 219-225.
Bok, J.W. and Keller, N. P., Fast and easy method for construction of plasmid vectors using modified quick-change mutagenesis., Methods Mol. Biol., 2012, 944, 163-174.
Bok, J.W., et al., 2015, Fungal artificial chromosomes for mining of the fungal secondary metabolome., BMC Genomics, 2015, 16, 343.
Brakhage, A.A. and Schroeckh, V., Fungal secondary metabolites—strategies to activate silent gene clusters., Fungal Genet. Biol., 2011, 48, 15-22.
Burke, D., et al., Cloning of large segments of exogenous DNA into yeast by means of artificial chromosome vectors., Science, 1987, 236, 806-812.
Chiang, Y.M., et al., An efficient system for heterologous expression of secondary metabolite genes in Aspergillus nidulans., J. Am. Chem. Soc. 2013, 135, 7720-7731.
Copeland, N.G., et al., Recombineering: A powerful new tool for mouse functional genomics., Nat. Rev. Genet., 2001, 2, 769-779.
Fierro, F., et al., Autonomously replicating plasmids carrying the AMA1 region in Penicillium chrysogenum., Curr. Genet., 1996, 29, 482-489.
Gems, D., et al., An autonomously replicating plasmid transforms Aspergillus nidulans at high frequency., Gene, 1991, 98, 61-67.
Ioannou P.A., et al., A new bacteriophage P1-derived vector for the propagation of large human DNA fragments., Nat. Genet., 1994, 6, 84-89.
Keller, N.P. and Hohn, T.M., Metabolic Pathway Gene Clusters in Filamentous Fungi., Fungal Genet. Biol., 1997, 21, 17-29.
Kubodera, T., et al., Pyrithiamine resistance gene (ptrA) of Aspergillus oryzae: cloning, characterization and application as a dominant selectable marker for transformation., Biosci. Biotechnol. Biochem., 2000, 64, 1416-1426.
Nielsen, M.T., et al., Heterologous reconstitution of the intact geodin gene cluster in Aspergillus nidulans through a simple and versatile PCR based approach., PLoS One, 2013, 8, e72871.
Shizuya, H., et al., Cloning and stable maintenance of 300-kilobase-pair fragments of human DNA in *Escherichia coli* using an F-factor-based vector., Proc. Natl. Acad. Sci. U.S.A., 1992, 89, 8794-8797.
Sosio, M., et al., Artificial chromosomes for antibiotic-producing actinomycetes. Nat. Biotechnol., 2000, 18, 343-345.

(Continued)

*Primary Examiner* — Nancy A Treptow
(74) *Attorney, Agent, or Firm* — Polsinelli PC

(57) ABSTRACT

Fungal artificial chromosome (FAC) vectors are disclosed. A vector can be replicated in a bacterial or a fungal host, and can comprise an insert of heterologous DNA up to about 500 kilobases. A vector can be used for cloning and expressing a secondary metabolite (SM) gene cluster. An insert sequence can be modified by homologous recombination. A vector can be a plasmid comprising bacterial and fungal origins of replication, as well as bacterial and fungal selection marker genes. Also disclosed are vectors that can be integrated into a fungal genome, and dual function vectors which can be replicated in a bacterial or a fungal host and can also be integrated into a fungal genome. Also disclosed are methods of generating plasmid libraries including vectors comprising intact SM gene clusters.

19 Claims, 6 Drawing Sheets

Specification includes a Sequence Listing.

(56) References Cited

OTHER PUBLICATIONS

Szewczyk, E., et al., Fusion PCR and gene targeting in Aspergillus nidulans. Nat. Protoc., 2006, 1, 3111-3120.
Hamilton, C.M. A binary-BAC system for plant transformation with high-molecular-weight DNA., Gene, 1997, 200, 107-116.
Takken, F.L., et al., One-step method to convert vectors into binary vectors suited for Agrobacterium-mediated transformation., Curr. Genet., 2004, 45, 242-248.
Yin, W.B., et al., Discovery of cryptic polyketide metabolites from Dermatophytes using heterologous expression in Aspergillus nidulans., ACS Synth. Biol., 2013, 2, 629-634.
Zhang, M., et al., Preparation of megabase-sized DNA from a variety of organisms using the nuclei method for advanced genomics research., Nat. Protoc., 2012, 7, 467-478.

* cited by examiner

SEQUENCE LISTING

```
<160> NUMBER OF SEQ ID NOS: 17

<210> SEQ ID NO 1
<211> LENGTH: 68
<212> TYPE: DNA
<213> ORGANISM: Artificial Sequence
<220> FEATURE:
<223> OTHER INFORMATION: Amplification primer

<400> SEQUENCE: 1
tgggactttg tcgctcacga ttcgccgagt tgtatgggct gaccagtgac cgacctgcag    60
cctgttga                                                             68

<210> SEQ ID NO 2
<211> LENGTH: 43
<212> TYPE: DNA
<213> ORGANISM: Artificial Sequence
<220> FEATURE:
<223> OTHER INFORMATION: Amplification primer

<400> SEQUENCE: 2
ggtgccccaa gccttggatc cgtcgaggct gatcagcgag ctc                      43

<210> SEQ ID NO 3
<211> LENGTH: 45
<212> TYPE: DNA
<213> ORGANISM: Artificial Sequence
<220> FEATURE:
<223> OTHER INFORMATION: Amplification primer

<400> SEQUENCE: 3
tcgctgatca gcctcgacgg atccaaggct tggggcacct gcgtt                    45

<210> SEQ ID NO 4
<211> LENGTH: 71
<212> TYPE: DNA
<213> ORGANISM: Artificial Sequence
<220> FEATURE:
<223> OTHER INFORMATION: Amplification primer

<400> SEQUENCE: 4
tcctcatgaa ttagatggtt agatggacct accatcagga taggttccat tgtgatgtct    60
gctcaagcgg g                                                         71

<210> SEQ ID NO 5
<211> LENGTH: 8
<212> TYPE: DNA
<213> ORGANISM: Artificial Sequence
<220> FEATURE:
<223> OTHER INFORMATION: Linker

<400> SEQUENCE: 5
``` ctggaaag                                                                          8

<210> SEQ ID NO 6
<211> LENGTH: 12
<212> TYPE: DNA
<213> ORGANISM: Artificial Sequence
<220> FEATURE:
<223> OTHER INFORMATION: Linker

<400> SEQUENCE: 6
ctttccagca ca                                                                    12

<210> SEQ ID NO 7
<211> LENGTH: 15684
<212> TYPE: DNA
<213> ORGANISM: Artificial Sequence
<220> FEATURE:
<223> OTHER INFORMATION: Vector

<400> SEQUENCE: 7
ccaccacagt gggatccgaa gcttggaatt cacgtgactt gaagtcatta ccctgttatc    60
cctagcggcc gcactgaccc tatagtgagt cgtattaatt taaatcatac caacatggtc   120
aaataaaacg aaaggctcag tcgaaagact ggccgcccag cttatttttt gtatactgtt   180
ttgtgatagc acgaagtttt tccacggtat cttgttaaaa atatatattt gtggcgggct   240
tacctacatc aaattaataa gagactaatt ataaactaaa cacacaagca agctacttta   300
gggtaaaagt ttataaatgc ttttgacgta taaacgttgc ttgtatttat tattacaatt   360
aaaggtggat agaaaaccta gagactagtt agaaactaat ctcaggtttg cgttaaacta   420
aatcagagcc cgagaggtta acagaaccta aaggggact agatatccgg gtagggaaac   480
aaaaaaaaaa aacaagacag ccacatatta gggagactag ttagaagcta gttccaggac   540
taggaaaata aaagacaatg ataccacagt ctagttgaca actagataga ttctagattg   600
aggccaaagt ctctgagatc caggttagtt gcaactaata ctagtagta tctagtctcc   660 tataactctg aagctagaat aacttactac tattatcctc accactgttc agctgcgcaa   720
acggagtgat tgcaaggtgt tcagagacta gttattgact agtcagtgac tagcaataac   780
taacaaggta ttaacctacc atgtctgcca tcaccctgca cttcctcggg ctcagcagcc   840
ttttcctcct cattttcatg ctcatttttcc ttgtttaaga ctgtgactag tcaaagacta   900
gtccagaacc acaaggaga aatgtcttac cactttcttc attgcttgtc tcttttgcat   960
tatccatgtc tgcaactagt tagagtctag ttagtgacta gtccgacgag gacttgcttg  1020
tctccggatt gttggaggaa ctctccaggg cctcaagatc cacaacagag ccttctagaa  1080
gactggtcaa taactagttg gtctttgtct gagtctgact tacgaggttg catactcgct  1140 cccttttgcct cgtcaatcga tgagaaaaag cgccaaaact cgcaatatgg ctttgaacca  1200
cacggtgctg agactagtta gaatctagtc ccaaactagc ttggatagct tacctttgcc  1260
ctttgcgttg cgacaggtct tgcagggtat ggttcctttc tcaccagctg atttagctgc  1320
cttgctaccc tcacggcgga tctgcataaa gagtggctag aggttataaa ttagcactga  1380
tcctaggtac ggggctgaat gtaacttgcc tttcctttct catcgcgcgg caagacaggc  1440
ttgctcaaat tcctaccagt cacaggggta tgcacggcgt acggaccact tgaactagtc  1500
acagattagt tagcaactag tctgcattga atggctgtac ttacgggccc tcgccattgt  1560
cctgatcatt tccagcttca ccctcgttgc tgcaaagtag ttagtgacta gtcaaggact  1620
agttgaaatg ggagaagaaa ctcacgaatt ctcgacaccc ttagtattgt ggtccttgga  1680

```
cttggtgctg ctatatatta gctaatacac tagttagact cacagaaact tacgcagctc   1740
gcttgcgctt cttggtagga gtcggggttg ggagaacagt gccttcaaac aagccttcat   1800
accatgctac ttgactagtc agggactagt caccaagtaa tctagatagg acttgccttt   1860
ggcctccatc agttccttca tagtgggagg tccattgtgc aatgtaaact ccatgccgtg   1920
ggagttcttg tccttcaagt gcttgaccaa tatgtttctg ttggcagagg gaacctgtca   1980
actagttaat aactagtcag aaactagtat agcagtagac tcactgtacg cttgaggcat   2040
cccttcactc ggcagtagac ttcatatgga tggatatcag gcacgccatt gtcgtcctgt   2100
ggactagtca gtaactaggc ttaaagctag tcgggtcggc ttactatctt gaaatccggc   2160
agcgtaagct ccccgtcctt aactgcctcg agatagtgac agtactctgg ggactttcgg   2220
agatcgttat cgcgaatgct cggcatacta atcgttgact agtcttggac tagtcccgag   2280
caaaaaggat tggaggagga ggaggaaggt gagagtgaga caaagagcga aataagagct   2340
tcaaaggcta tctctaagca gtatgaaggt taagtatcta gttcttgact agatttaaaa   2400
gagatttcga ctagttatgt acctggagtt tggatatagg aatgtgttgt ggtaacgaaa   2460
tgtaaggggg aggaaagaaa aagtcggtca agaggtaact ctaagtcggc cattcctttt   2520
tgggaggcgc taaccataaa cggcatggtc gacttagagt tagctcaggg aatttaggga   2580
gttatctgcg accaccgagg aacggcggaa tgccaaagaa tcccgatgga gctctagctg   2640
gcggttgaca accccacctt ttggcgtttc tgcggcgttg caggcgggac tggatacttc   2700
gtagaaccag aaaggcaagg cagaacgcgc tcagcaagag tgttggaagt gatagcatga   2760
tgtgccttgt taactaggtc aaaatctgca ggtatgcttg atgttatcca aagtgtgaga   2820
gaggaaggtc caaacataca cgattgggag agggcctagg tataagagtt tttgagtaga   2880
acgcatgtga gcccagccat ctcgaggaga ttaaacacgg gccggcattt gatggctatg   2940
ttagtacccc aatggaaagc ctgagagtcc agtggtcgca gataactccc taaattccct   3000
gagctaactc taagtcgacc atgccgttta tggttagcgc ctcccaaaaa ggaatggccg   3060
acttagagtt acctcttgac cgacttttc tttcctcccc cttacatttc gttaccacaa   3120
cacattccta tatccaaact ccaggtacat aactagtcga atctcttttt aaatctagtc   3180
aagaactaga tacttaacct tcatactgct tagagatagc cttttgaagct cttatttcgc   3240 tctttgtctc actctcacct tcctcctcct cctccaatcc ttttttgctcg ggactagtcc   3300 aagactagtc aacgattagt atgccgagca ttcgcgataa cgatctccga aagtccccag   3360
agtactgtca ctatctcgag gcagttaagg acggggagtc tacgctgccg gatttcaaga   3420
tagtaagccg acccgactag ctttaagcct agttactgac tagtccacag gacgacaatg   3480
gcgtgcctga tatccatcca tatgaagtct actgccgagt gaagggatgc ctcaagcgta   3540
cagtgagtct actgctatac tagttttctga ctagttatta actagttgac aggttccctc   3600
tgccaacaga aacatattgg tcaagcactt gaaggacaag aactcccacg gcatggagtt   3660
tacattgcac aatggaccct ccactatgaa ggaactgatg gaggccaaag gcaagtccta   3720
tctagattac ttggtgacta gtccctgact agtcaagtag catggtatga aggcttgttt   3780
gaaggcactg ttctcccaac cccgactcct accaagaagc gcaagcgagc tcgtaagtt   3840 tctgtgagtc taactagtgt attagctaat atatagcagc accaagtcca aggaccacaa   3900
tactaagggt gtcgagaatt cgtgagtttc ttctccccatt tcaactagtc cttgactagt   3960
cactaactac tttgcagcaa cgagggtgaa gctggaaatg atcaggacaa tggcgagggc   4020
```

-continued

```
ccgtaagtac agccattcaa tgcagactag ttgctaacta atctgtgact agttcaagtg    4080
gtccgtacgc cgtgcatacc cctgtgactg gtaggaattt gagcaagcct gtcttgccgc    4140
gcgatgagaa aggaaaggca agttacattc agccccgtac ctaggatcag tgctaattta    4200
taacctctag ccactcttta tgcagatccg ccgtgagggt agcaaggcag ctaaatcagc    4260
tggtgagaaa ggaaccatac cctgcaagac ctgtcgcaac gcaaagggca aggtaagct    4320 atccaagcta gtttgggact agattctaac tagtctcagc accgtgtggt tcaaagccat    4380
attgcgagtt ttggcgcttt ttctcatcga ttgacgaggc aaagggagcg agtatgcaac    4440
ctcgtaagtc agactcagac aaagaccaac tagttattga ccagtcttct agaaggctct    4500
gttgtggatc ttgaggccct ggagagttcc tccaacaatc cggagacaag caagtcctcg    4560
tcggactagt cactaactag actctaacta gttgcagaca tggataatgc aaaagagaca    4620
agcaatgaag aaagtggtaa gacatttctc ctttgtggtt ctggactagt ctttgactag    4680
tcacagtctt aaacaaggaa aatgagcatg aaaatgagga ggaaaaggct gctgagcccg    4740
aggaagtgca gggtgatggc agacatggta ggttaatacc ttgttagtta ttgctagtca    4800
ctgactagtc aataactagt ctctgaacac cttgcaatca ctccgtttgc gcagctgaac    4860
agtggtgagg ataatagtag taagttattc tagcttcaga gttataggag actagatact    4920
aactagtatt agttgcaact aacctggatc tcagagactt tggcctcaat ctagaatcta    4980
tctagttgtc aactagactg tggtatcatt gtcttttatt ttcctagtcc tggaactagc    5040
ttctaactag tctccctaat atgtggctgt cttgtttttt tttttgttt ccctacccgg    5100 atatctagtc ccccttctagg ttctgttaac ctctcgggct ctgatttagt ttaacgcaaa    5160
cctgagatta gtttctaact agtctctagg ttttctatcc acctttaatt gtaataataa    5220
atacaagcaa cgtttatacg tcaaaagcat ttataaactt ttaccctaaa gtagcttgct    5280
tgtgtgttta gtttataatt agtctcttat taatttgatg taggtaagcc cgccacaaat    5340
atatattttt aacaagatac cgtggaaaaa cttcgtgcta tcacaaaaca gtatacaaaa    5400
aataagctga tccacaggac gggtgtggtc gccatgatcg cgtagtcgat agtggctcca    5460
agtagcgaag cgagcaggac tgggcggcgg ccaaagcggt cggacagtgc tccgagaacg    5520
ggtgcgcata gaaattgcat caacgcatat agcgctagca gcacgccata gtgactggcg    5580
atgctgtcgg aatggacgat atcccgcaag aggcccggca gtaccggcat aaccaagcct    5640
atgcctacag catccagggt gacggtgccg aggatgacga tgagcgcatt gttagatttc    5700
atacacggtg cctgactgcg ttagcaattt aactgtgata aactaccgca ttaaagcttc    5760
gacatcaccc ttacccaaac tatatccaat gagcaaagaa taacgagtca agcgggcgc    5820 attttcatc acatacgagt atgcacagtc aggactccac gtcatacatc aaaaacttgg    5880
aacgcatgag tctagctcag ctcggctctt ttccgatttt tgcgcagctt ctgttgcgga    5940
tcttgctgct tgtggagtct atgccccggc tgatgcattg aaacacaacg cgcagatgat    6000
ccaatcatac caaccagacg catcagcgcg tgtagctggg ggaagggtag gtggtgtagc    6060
ccagaaagcg acacggctgg ctttcaagaa gtttatcaac cctagacagc tttggagcgg    6120
atacccggct cttgtggcgc atagcttgcc agtgtcggcg atacagatgc ctctgtacga    6180
gacttttcgg tatcgaattt ctgaatatag attcggagat cgagagaagg tgctagaaag    6240
atcaagagat tatggaaaag aaacaggccc attcgacaat cggagaggct gcagcgacag    6300
ccgcgataag tgctgcagcc tcgggcggta tagccagtgt cttgacagca cccatggata    6360
tagtccggac acgaatcatg ctcgatgctg cagacacaac cgcacctcag aagaaaagga    6420
```

```
tgatcaatac cgtacgggag attatacgaa cagatggccc gagaggacta ttccgagggt    6480
gtgctatcaa cacgtttatg gccgctgtcg gatcagggtt atactttggt ctctacgaaa    6540
gcaccaaatg gtggctaggc tcggactcga tggataatag tgccatgtta gagtaagggg    6600
tgatgggaaa tcttgtatat aattgtgatt gtttgtacga tagtggccga ctgtacatta    6660
gtgatacccc actcttagaa aatagaccaa tctccagctg caccttcaga caatccgggt    6720
aaaaattctc gtctatgttg gagattggtg tgattttgaa acatgaccct tgactctgat    6780
cttgaatatg tccatatctc gaggcaggca tattattcat atagagaggg tatcccttag    6840
catcggtctg tcgtagtatc cgactgctga atttatgaat cgcatcatac ttgcgacata    6900
ctgccataaa aagagtacgt atccaccact acttattgcg caccaacacg cttcaggtat    6960
gcatcccatc cctctttctg gtaccgcttc gccgcctcca cgggatcagg agcagcataa    7020
attccacgac cagcaatgat aaagtcggca ccgcgtccaa cagcagattc aggagtctgg    7080
tattgctgtc ccagcttgtc tcccttcgag gagaggttga cacctgtcgt gaacacgacg    7140
aaatcctcct cctccgaagg agagctaact tcagactgaa cctcgcccag gtgacgcgtc    7200
gagacgaatc ccatcacaaa cttcttatac ttccgagcat agtcaacaga gaagtagta    7260 tattgaccgg tagccaaaga tcccttggat gtcatctccg caaggatcaa aaggcccctc    7320
tcagagccgt agggaaagtc ctcggccgaa gcagtctggg ctagagcctc gacgataccc    7380
tcaccgggca gaatactgca gttgatgatg tgggcccact cggagatgcg cagagtgccg    7440
ccatggtact gcttttggac tgtgtttccg atatcgatga acttgcgatc ttcgaagatg    7500
aggaaattgt gcttctctgc aagggccttc agaccggtga tggtctcttc gctgaaatcg    7560
gagaggatat cgatgtgagt tttgatcacg gcaatgtacg gaccgagtcc tgttaaataa    7620
tccaccatta accattatta gatcattatg taagtggcat ccccggtgcg catacggtca    7680
gccaaatcca gcagctcttt ggtggttgtc acgtcggccg aaacggtgac attggttttc    7740
ttggcctcgg caacctcaaa gagcttcttt acgagggcat tggggtgctt gctagcgcgt    7800
gcactgtagg tcaattgcga cttggaagac atgttggcga tggaggggta gcgcggggtt    7860
ctgcaactat cgtagaaatg agcacttagt ggttgaaacc ggcttattca gtagattaat    7920
acttgaagtt tttagtaatc agacagaata atcaggatgt ccaattacta cctcttaata    7980
tgtggaatga atgatagata taaattgtac gacaattgcc gcgaaaaatt aaaatggatc    8040
tatggagggg acagtcatgc actagccaca cgttcctccg cctgtggggt gagccacatg    8100
cctcatctgg accaaacaca tcgatgcagt cacatgcaga taagattagg gcctatcctt    8160
agggtacctg tccgcgcggg gattatgcct ggcttttgc ctgcttttga tatcctttca    8220
aggacatagc gataagtcca acctatcggc cataataat gtcaatgcca gcagcggctt    8280
gggcctagaa tattccatca gctactgaac aacttctaca tcacaatttg aaagctctaa    8340
gaattaatat agaagcactt accttcgcat tttctggtat attgttctga gatccatagg    8400
atcagcttat cgatgataag ctgtcaaaca tgagaattcg ggccgtcgac caattctcat    8460
gtttgacagc ttatcatcga atttctgcca ttcatccgct tattatcact tattcaggcg    8520
tagcaaccag gcgtttaagg gcaccaataa ctgccttaaa aaaattacgc cccgccctgc    8580
cactcatcgc agtactgttg taattcatta agcattctgc cgacatggaa gccatcacaa    8640
acggcatgat gaacctgaat cgccagcggc atcagcacct tgtcgccttg cgtataatat    8700
ttgcccatgg tgaaaacggg ggcgaagaag ttgtccatat tggccacgtt taaatcaaaa    8760
```

```
ctggtgaaac tcacccaggg attggctgag acgaaaaaca tattctcaat aaacccttta    8820
gggaaatagg ccaggttttc accgtaacac gccacatctt gcgaatatat gtgtagaaac    8880
tgccggaaat cgtcgtggta ttcactccag agcgatgaaa acgtttcagt ttgctcatgg    8940
aaaacggtgt aacaagggtg aacactatcc catatcacca gctcaccgtc tttcattgcc    9000
atacgtaatt ccagatgtaa attcatcatc aggcgggcaa gaatgtgaat aaaggccgga    9060
taaaacttgt gcttattttt ctttacggtc tttaaaaagg ccgtaatatc cagctgaacg    9120
gtctggttat aggtacattg agcaactgac tgaaatgcct caaaatgttc tttacgatgc    9180
cattgggata tatcaacggt ggtatatcca gtgatttttt tctccatttt agcttcctta    9240
gctcctgaaa atctcgataa ctcaaaaaat acgcccggta gtgatcttat ttcattatgg    9300
tgaaagttgg aacctcttac gtgccgatca acgtctcatt ttcgccaaaa gttggcccag    9360
ggcttcccgg tatcaacagg gacaccagga tttatttatt ctgcgaagtg atcttccgtc    9420
acaggtatTT attcgcgata agctcatgga gcggcgtaac cgtcgcacag gaaggacaga    9480
gaaagcgcgg atctgggaag tgacggacag aacggtcagg acctggattg gggaggcggt    9540
tgccgccgct gctgctgacg gtgtgacgtt ctctgttccg gtcacaccac atacgttccg    9600
ccattcctat gcgatgcaca tgctgtatgc cggtataccg ctgaaagttc tgcaaagcct    9660
gatgggacat aagtccatca gttcaacgga agtctacacg aaggtttttg cgctggatgt    9720
ggctgcccgg caccgggtgc agtttgcgat gccggagtct gatgcggttg cgatgctgaa    9780
acaattatcc tgagaataaa tgccttggcc tttatatgga aatgtggaac tgagtggata    9840
tgctgttttt gtctgttaaa cagagaagct ggctgttatc cactgagaag cgaacgaaac    9900
agtcgggaaa atctcccatt atcgtagaga tccgcattat taatctcagg agcctgtgta    9960
gcgtttatag gaagtagtgt tctgtcatga tgcctgcaag cggtaacgaa acgatttga   10020 atatgccttc aggaacaata gaaatcttcg tgcggtgtta cgttgaagtg gagcggatta   10080
tgtcagcaat ggacagaaca acctaatgaa cacagaacca tgatgtggtc tgtccttttA   10140
cagccagtag tgctcgccgc agtcgagcga cagggcgaag cccctggttg ccctcgccgc   10200
tgggctggcg gccgtctatg gccctgcaaa cgcgccagaa acgccgtcga agccgtgtgc   10260
gagacaccgc ggccggccgc cggcgttgtg gatacctcgc ggaaaacttg ccctcactg    10320 acagatgagg ggcggacgtt gacacttgag gggccgactc acccggcgcg cgttgacag    10380 atgaggggca ggctcgattt cggccggcga cgtggagctg gccagcctcg caaatcggcg   10440
aaaacgcctg attttacgcg agtttcccac agatgatgtg gacaagcctg gggataagtg   10500
ccctgcggta ttgacacttg aggggcgcga ctactgacag atgaggggcg cgatccttga   10560
cacttgaggg gcagagtgct gacagatgag gggcgcacct attgacattt gagggggctgt  10620 ccacaggcag aaaatccagc atttgcaagg gtttccgccc gttttTcggc caccgctaac   10680
ctgtctttta acctgctttt aaaccaatat ttataaacct tgttttttaac cagggctgcg   10740 ccctgtgcgc gtgaccgcgc acgccgaagg ggggtgcccc cccttctcga accctcccgg   10800
tcgagtgagc gaggaagcac cagggaacag cacttatata ttctgcttac acacgatgcc   10860
tgaaaaaact tcccctgggg ttatccactt atccacgggg atattttttat aattattttt   10920 tttatagttt ttagatcttc tttttttagag cgccttgtag gcctttatcc atgctggttc   10980
tagagaaggt gttgtgacaa attgcccttt cagtgtgaca aatcaccctc aaatgacagt   11040
cctgtctgtg acaaattgcc cttaaccctg tgacaaattg ccctcagaag aagctgtttt   11100
ttcacaaagt tatccctgct tattgactct ttttTatttA gtgtgacaat ctaaaaactt   11160
```

```
gtcacacttc acatggatct gtcatggcgg aaacagcggt tatcaatcac aagaaacgta    11220
aaaatagccc gcgaatcgtc cagtcaaacg acctcactga ggcggcatat agtctctccc    11280
gggatcaaaa acgtatgctg tatctgttcg ttgaccagat cagaaaatct gatggcaccc    11340
tacaggaaca tgacggtatc tgcgagatcc atgttgctaa atatgctgaa atattcggat    11400
tgacctctgc ggaagccagt aaggatatac ggcaggcatt gaagagtttc gcggggaagg    11460
aagtggtttt ttatcgccct gaagaggatg ccggcgatga aaaaggctat gaatcttttc    11520
cttggtttat caaacgtgcg cacagtccat ccagagggct ttacagtgta catatcaacc    11580
catatctcat tcccttcttt atcgggttac agaaccggtt tacgcagttt cggcttagtg    11640
aaacaaaaga aatcaccaat ccgtatgcca tgcgtttata cgaatccctg tgtcagtatc    11700
gtaagccgga tggctcaggc atcgtctctc tgaaaatcga ctggatcata gagcgttacc    11760
agctgcctca aagttaccag cgtatgcctg acttccgccg ccgcttcctg caggtctgtg    11820
ttaatgagat caacagcaga actccaatgc gcctctcata cattgagaaa agaaaggcc    11880 gccagacgac tcatatcgta ttttccttcc gcgatatcac ttccatgacg acaggatagg    11940
ctagtgataa taagtgactg aggtatgtgc tcttcttatc tccttttgta gtgttgctct    12000
tattttaaac aactttgcgg ttttttgatg actttgcgat tttgttgttg ctttgcagta    12060
aattgcaaga tttaataaaa aaacgcaaag caatgattaa aggatgttca gaatgaaact    12120
catggaaaca cttaaccagt gcataaacgc tggtcatgaa atgacgaagg ctatcgccat    12180
tgcacagttt aatgatgaca gcccggaagc gaggaaaata acccggcgct ggagaatagg    12240
tgaagcagcg gatttagttg gggtttcttc tcaggctatc agagatgccg agaaagcagg    12300
gcgactaccg cacccggata tggaaattcg aggacgggtt gagcaacgtg ttggttatac    12360
aattgaacaa attaatcata tgcgtgatgt gtttggtacg cgattgcgac gtgctgaaga    12420
cgtatttcca ccggtgatcg gggttgctgc ccataaagaa aggtggcgtt tacaaaacct    12480
cagtttctgt tcatcttgct caggatctgg ctctgaaggg gctacgtgtt ttgctcgtgg    12540
aaggtaacga cccccaggga acagcctcaa tgtatcacgg atgggtacca gatcttcata    12600
ttcatgcaga agacactctc ctgcctttct atcttgggga aaaggacgat gtcacttatg    12660
caataaagcc cacttgctgg ccggggcttg acattattcc ttcctgtctg gctctgcacc    12720
gtattgaaac tgagttaatg ggcaaatttg atgaaggtaa actgcccacc gatccacacc    12780
tgatgctccg actggccatt gaaactgttg ctcatgacta tgatgtcata gttattgaca    12840
gcgcgcctaa cctgggtatc ggcacgatta atgtcgtatg tgctgctgat gtgctgattg    12900
ttcccacgcc tgctgagttg tttgactaca cctccgcact gcagttttc gatatgcttc    12960 gtgatctgct caagaacgtt gatcttaaag ggttcgagcc tgatgtacgt attttgctta    13020
ccaaatacag caatagtaat ggctctcagt ccccgtggat ggaggagcaa attcgggatg    13080
cctggggaag catggttcta aaaaatgttg tacgtgaaac ggatgaagtt ggtaaaggtc    13140
agatccggat gagaactgtt tttgaacagg ccattgatca acgctcttca actggtgcct    13200
ggagaaatgc tctttctatt tgggaacctg tctgcaatga aattttcgat cgtctgatta    13260
aaccacgctg ggagattaga taatgaagcg tgcgcctgtt attccaaaac atacgctcaa    13320
tactcaaccg gttgaagata cttcgttatc gacaccagct gccccgatgg tggattcgtt    13380
aattgcgcgc gtaggagtaa tggctcgcgg taatgccatt actttgcctg tatgtggtcg    13440
ggatgtgaag tttactcttg aagtgctccg gggtgatagt gttgagaaga cctctcgggt    13500
```

```
atggtcaggt aatgaacgtg accaggagct gcttactgag gacgcactgg atgatctcat    13560
cccttctttt ctactgactg gtcaacagac accggcgttc ggtcgaagag tatctggtgt    13620
catagaaatt gccgatggga gtcgccgtcg taaagctgct gcacttaccg aaagtgatta    13680
tcgtgttctg gttggcgagc tggatgatga gcagatggct gcattatcca gattgggtaa    13740
cgattatcgc ccaacaagtg cttatgaacg tggtcagcgt tatgcaagcc gattgcagaa    13800
tgaatttgct ggaaatattt ctgcgctggc tgatgcggaa atatttcac gtaagattat    13860
tacccgctgt atcaacaccg ccaaattgcc taaatcagtt gttgctcttt tttctcaccc    13920
cggtgaacta tctgcccggt caggtgatgc acttcaaaaa gcctttacag ataaagagga    13980
attacttaag cagcaggcat ctaaccttca tgagcagaaa aaagctgggg tgatatttga    14040
agctgaagaa gttatcactc ttttaacttc tgtgcttaaa acgtcatctg catcaagaac    14100
tagtttaagc tcacgacatc agtttgctcc tggagcgaca gtattgtata agggcgataa    14160
aatggtgctt aacctggaca ggtctcgtgt tccaactgag tgtatagaga aaattgaggc    14220
cattcttaag gaacttgaaa agccagcacc ctgatgcgac cacgttttag tctacgttta    14280
tctgtcttta cttaatgtcc tttgttacag gccagaaagc ataactggcc tgaatattct    14340
ctctgggccc actgttccac ttgtatcgtc ggtctgataa tcagactggg accacggtcc    14400
cactcgtatc gtcggtctga ttattagtct gggaccacgg tcccactcgt atcgtcggtc    14460
tgattattag tctgggacca cggtcccact cgtatcgtcg gtctgataat cagactggga    14520
ccacggtccc actcgtatcg tcggtctgat tattagtctg gaccatggt cccactcgta    14580
tcgtcggtct gattattagt ctgggaccac ggtcccactc gtatcgtcgg tctgattatt    14640
agtctggaac cacggtccca ctcgtatcgt cggtctgatt attagtctgg gaccacggtc    14700
ccactcgtat cgtcggtctg attattagtc tgggaccacg atcccactcg tgttgtcggt    14760
ctgattatcg gtctgggacc acggtcccac ttgtattgtc gatcagacta tcagcgtgag    14820
actacgattc catcaatgcc tgtcaagggc aagtattgac atgtcgtcgt aacctgtaga    14880
acggagtaac ctcggtgtgc ggttgtatgc ctgctgtgga ttgctgctgt gtcctgctta    14940
tccacaacat tttgcgcacg gttatgtgga caaaatacct ggttaccag gccgtgccgg    15000
cacgttaacc gggctgcatc cgatgcaagt gtgtcgctgt cgacgagctc gcgagctcgg    15060
acatgaggtt gccccgtatt cagtgtcgct gatttgtatt gtctgaagtt gtttttacgt    15120
taagttgatg cagatcaatt aatacgatac ctgcgtcata attgattatt tgacgtggtt    15180
tgatggcctc cacgcacgtt gtgatatgta atgataatc attatcactt tacgggtcct    15240
ttccggtgat ccgacaggtt acggggcggc gacctcgcgg gttttcgcta tttatgaaaa    15300
ttttccggtt taaggcgttt ccgttcttct tcgtcataac ttaatgtttt tatttaaaat    15360
accctctgaa agaaaggaa acgacaggtg ctgaaagcga gcttttggc ctctgtcgtt    15420
tcctttctct gtttttgtcc gtggaatgaa caatggaagt ccgagctcat cgctaataac    15480
ttcgtatagc atacattata cgaagttata ttcgatgcgg ccaaggtgag ccagtgtgat    15540
tacatttgcg gcctaactgt ggccagtcca gttacgctgg agtcactagt atttaggtga    15600
cactatagaa gcgccgcta gggataacag ggtaatgaca acttgtccac gtggaattct    15660
aagcttagga tcccactgtg gtgg                                          15684
```

<210> SEQ ID NO 8
<211> LENGTH: 5250
<212> TYPE: DNA
<213> ORGANISM: Artificial Sequence
<220> FEATURE:
<223> OTHER INFORMATION: Fungal replication origin

<400> SEQUENCE: 8

```
agcttatttt ttgtatactg ttttgtgata gcacgaagtt tttccacggt atcttgttaa      60
aaatatatat ttgtggcggg cttacctaca tcaaattaat aagagactaa ttataaacta     120
aacacacaag caagctactt tagggtaaaa gtttataaat gcttttgacg tataaacgtt     180
gcttgtattt attattacaa ttaaaggtgg atagaaaacc tagagactag ttagaaacta     240
atctcaggtt tgcgttaaac taaatcagag cccgagaggt taacagaacc tagaagggga     300
ctagatatcc gggtagggaa acaaaaaaaa aaaacaagac agccacatat tagggagact     360
agttagaagc tagttccagg actaggaaaa taaaagacaa tgataccaca gtctagttga     420
caactagata gattctagat tgaggccaaa gtctctgaga tccaggttag ttgcaactaa     480
tactagttag tatctagtct cctataactc tgaagctaga ataacttact actattatcc     540
tcaccactgt tcagctgcgc aaacggagtg attgcaaggt gttcagagac tagttattga     600
ctagtcagtg actagcaata actaacaagg tattaaccta ccatgtctgc catcaccctg     660
cacttcctcg ggctcagcag ccttttcctc ctcattttca tgctcatttt ccttgtttaa     720
gactgtgact agtcaaagac tagtccagaa ccacaaagga gaaatgtctt accactttct     780
tcattgcttg tctcttttgc attatccatg tctgcaacta gttagagtct agttagtgac     840
tagtccgacg aggacttgct tgtctccgga ttgttggagg aactctccag ggcctcaaga     900
tccacaacag agccttctag aagactggtc aataactagt tggtctttgt ctgagtctga     960
cttacgaggt tgcatactcg ctcccttttgc ctcgtcaatc gatgagaaaa agcgccaaaa    1020
ctcgcaatat ggcttttgaac cacacggtgc tgagactagt tagaatctag tcccaaacta    1080
gcttggatag cttacctttg cccttgcgt tgcgacaggt cttgcagggt atggttcctt      1140
tctcaccagc tgatttagct gccttgctac cctcacggcg gatctgcata aagagtggct    1200
agaggttata aattagcact gatcctaggt acggggctga atgtaacttg cctttccttt    1260
ctcatcgcgc ggcaagacag gcttgctcaa attcctacca gtcacagggg tatgcacggc    1320
gtacggacca cttgaactag tcacagatta gttagcaact agtctgcatt gaatggctgt    1380
acttacgggc cctcgccatt gtcctgatca tttccagctt caccctcgtt gctgcaaagt    1440
agttagtgac tagtcaagga ctagttgaaa tgggagaaga aactcacgaa ttctcgacac    1500
ccttagtatt gtggtccttg gacttggtgc tgctatatat tagctaatac actagttaga    1560
ctcacagaaa cttacgcagc tcgcttgcgc ttcttggtag gagtcggggt tgggagaaca    1620
gtgccttcaa acaagccttc ataccatgct acttgactag tcagggacta gtcaccaagt    1680
aatctagata ggacttgcct ttggcctcca tcagttcctt catagtggga ggtccattgt    1740
gcaatgtaaa ctccatgccg tgggagttct tgtccttcaa gtgcttgacc aatatgtttc    1800
tgttggcaga gggaacctgt caactagtta ataactagtc agaaactagt atagcagtag    1860
actcactgta cgcttgaggc atcccttcac tcggcagtag acttcatatg gatggatatc    1920
aggcacgcca ttgtcgtcct gtggactagt cagtaactag gcttaaagct agtcgggtcg    1980
gcttactatc ttgaaatccg gcagcgtaag ctccccgtcc ttaactgcct cgagatagtg    2040
acagtactct ggggactttc ggagatcgtt atcgcgaatg ctcggcatac taatcgttga    2100
ctagtcttgg actagtcccg agcaaaaagg attggaggag gaggaggaag gtgagagtga    2160
gacaaagagc gaaataagag cttcaaaggc tatctctaag cagtatgaag gttaagtatc    2220
```

-continued

```
tagttcttga ctagatttaa aagagatttc gactagttat gtacctggag tttggatata    2280
ggaatgtgtt gtggtaacga aatgtaaggg ggaggaaaga aaaagtcggt caagaggtaa    2340
ctctaagtcg gccattcctt tttgggaggc gctaaccata aacggcatgg tcgacttaga    2400
gttagctcag ggaatttagg gagttatctg cgaccaccga ggaacggcgg aatgccaaag    2460
aatcccgatg gagctctagc tggcggttga caaccccacc ttttggcgtt tctgcggcgt    2520
tgcaggcggg actggatact tcgtagaacc agaaaggcaa ggcagaacgc gctcagcaag    2580
agtgttggaa gtgatagcat gatgtgcctt gttaactagg tcaaaatctg caggtatgct    2640
tgatgttatc caaagtgtga gagaggaagg tccaaacata cacgattggg agagggccta    2700
ggtataagag ttttttgagta aacgcatgt gagcccagcc atctcgagga gattaaacac    2760
gggccggcat ttgatggcta tgttagtacc ccaatggaaa gcctgagagt ccagtggtcg    2820
cagataactc cctaaattcc ctgagctaac tctaagtcga ccatgccgtt tatggttagc    2880
gcctcccaaa aaggaatggc cgacttagag ttacctcttg accgactttt tctttcctcc    2940
cccttacatt tcgttaccac aacacattcc tatatccaaa ctccaggtac ataactagtc    3000
gaaatctctt ttaaatctag tcaagaacta gatacttaac cttcatactg cttagagata    3060
gcctttgaag ctcttatttc gctctttgtc tcactctcac cttcctcctc ctcctccaat    3120 ccttttttgct cgggactagt ccaagactag tcaacgatta gtatgccgag cattcgcgat    3180
aacgatctcc gaaagtcccc agagtactgt cactatctcg aggcagttaa ggacggggag    3240
cttacgctgc cggatttcaa gatagtaagc cgacccgact agctttaagc ctagttactg    3300
actagtccac aggacgacaa tggcgtgcct gatatccatc catatgaagt ctactgccga    3360
gtgaagggat gcctcaagcg tacagtgagt ctactgctat actagtttct gactagttat    3420
taactagttg acaggttccc tctgccaaca gaaacatatt ggtcaagcac ttgaaggaca    3480
agaactccca cggcatggag tttacattgc acaatggacc tcccactatg aaggaactga    3540
tggaggccaa aggcaagtcc tatctagatt acttggtgac tagtccctga ctagtcaagt    3600
agcatggtat gaaggcttgt ttgaaggcac tgttctccca accccgactc ctaccaagaa    3660
gcgcaagcga gctgcgtaag tttctgtgag tctaactagt gtattagcta atatatagca    3720
gcaccaagtc caaggaccac aatactaagg gtgtcgagaa ttcgtgagtt tcttctccca    3780
tttcaactag tccttgacta gtcactaact actttgcagc aacgagggtg aagctggaaa    3840
tgatcaggac aatggcgagg gcccgtaagt acagccattc aatgcagact agttgctaac    3900
taatctgtga ctagttcaag tggtccgtac gccgtgcata cccctgtgac tggtaggaat    3960
ttgagcaagc ctgtcttgcc gcgcgatgag aaaggaaagg caagttacat tcagcccgt    4020 acctaggatc agtgctaatt tataacctct agccactctt tatgcagatc cgccgtgagg    4080
gtagcaaggc agctaaatca gctggtgaga aaggaaccat accctgcaag acctgtcgca    4140
acgcaaaggg caaggtaagc tatccaagc tagtttggga ctagattcta actagtctca    4200
gcaccgtgtg gttcaaagcc atattgcgag ttttggcgct ttttctcatc gattgacgag    4260
gcaaagggag cgagtatgca acctcgtaag tcagactcag acaaagacca actagttatt    4320
gaccagtctt ctagaaggct ctgttgtgga tcttgaggcc ctggagagtt cctccaacaa    4380
tccggagaca agcaagtcct cgtcggacta gtcactaact agactctaac tagttgcaga    4440
catggataat gcaaaagaga caagcaatga agaaagtggt aagacatttc tcctttgtgg    4500
ttctggacta gtctttgact agtcacagtc ttaaacaagg aaaatgagca tgaaaatgag    4560
gaggaaaagg ctgctgagcc cgaggaagtg cagggtgatg gcagacatgg taggttaata    4620
```

```
ccttgttagt tattgctagt cactgactag tcaataacta gtctctgaac accttgcaat    4680
cactccgttt gcgcagctga acagtggtga ggataatagt agtaagttat tctagcttca    4740
gagttatagg agactagata ctaactagta ttagttgcaa ctaacctgga tctcagagac    4800
tttggcctca atctagaatc tatctagttg tcaactagac tgtggtatca ttgtctttta    4860
ttttcctagt cctggaacta gcttctaact agtctcccta atatgtggct gtcttgtttt    4920 tttttttgt ttccctaccc ggatatctag tccccttcta ggttctgtta acctctcggg    4980
ctctgattta gtttaacgca aacctgagat tagtttctaa ctagtctcta ggttttctat    5040
ccacctttaa ttgtaataat aaatacaagc aacgtttata cgtcaaaagc atttataaac    5100
ttttacccta aagtagcttg cttgtgtgtt tagtttataa ttagtctctt attaatttga    5160
tgtaggtaag cccgccacaa atatatattt ttaacaagat accgtggaaa aacttcgtgc    5220
tatcacaaaa cagtatacaa aaaataagct                                     5250
```

<210> SEQ ID NO 9
<211> LENGTH: 3031
<212> TYPE: DNA
<213> ORGANISM: Artificial Sequence
<220> FEATURE:
<223> OTHER INFORMATION: fungal selection marker

<400> SEQUENCE: 9

```
gatccacagg acgggtgtgg tcgccatgat cgcgtagtcg atagtggctc caagtagcga     60
agcgagcagg actgggcggc ggccaaagcg gtcggacagt gctccgagaa cgggtgcgca    120
tagaaattgc atcaacgcat atagcgctag cagcacgcca tagtgactgg cgatgctgtc    180
ggaatggacg atatcccgca agaggcccgg cagtaccggc ataaccaagc ctatgcctac    240
agcatccagg gtgacggtgc cgaggatgac gatgagcgca ttgttagatt tcatacacgg    300
tgcctgactg cgttagcaat ttaactgtga taaactaccg cattaaagct tcgacatcac    360
ccttacccaa actatatcca atgagcaaag aataacgagt caaagcgggc gcatttttca    420
tcacatacga gtatgcacag tcaggactcc acgtcataca tcaaaaactt ggaacgcatg    480
agtctagctc agctcggctc ttttccgatt tttgcgcagc ttctgttgcg gatcttgctg    540
cttgtggagt ctatgccccg gctgatgcat tgaaacacaa cgcgcagatg atccaatcat    600
accaaccaga cgcatcagcg cgtgtagctg ggggaagggt aggtggtgta gcccagaaag    660
cgacacggct ggctttcaag aagtttatca accctagaca gctttggagc ggatacccgg    720
ctcttgtggc gcatagcttg ccagtgtcgg cgatacagat gcctctgtac gagacttttc    780
ggtatcgaat ttctgaatat agattcggag atcgagagaa ggtgctagaa agatcaagag    840
attatggaaa agaaacaggc ccattcgaca atcgagaggg ctgcagcgac agccgcgata    900
agtgctgcag cctcgggcgg tatagccagt gtcttgacag cacccatgga tatagtccgg    960
acacgaatca tgctcgatgc tgcagacaca accgcacctc agaagaaaag gatgatcaat   1020
accgtacggg agattatacg aacagatggc ccgagaggac tattccgagg gtgtgctatc   1080
aacacgttta tggccgctgt cggatcaggg ttatactttg gtctctacga aagcaccaaa   1140
tggtggctag gctcggactc gatggataat agtgccatgt tagagtaagg ggtgatggga   1200
aatcttgtat ataattgtga ttgtttgtac gatagtggcc gactgtacat tagtgatacc   1260
ccactcttag aaaatagacc aatctccagc tgcaccttca gacaatccgg gtaaaaattc   1320
tcgtctatgt tggagattgg tgtgattttg aaacatgacc cttgactctg atcttgaata   1380
```

-continued

```
tgtccatatc tcgaggcagg catattattc atatagagag ggtatccctt agcatcggtc    1440
tgtcgtagta tccgactgct gaatttatga atcgcatcat acttgcgaca tactgccata    1500
aaaagagtac gtatccacca ctacttattg cgcaccaaca cgcttcaggt atgcatccca    1560
tccctctttc tggtaccgct cgccgcctc cacgggatca ggagcagcat aaattccacg     1620
accagcaatg ataaagtcgg caccgcgtcc aacagcagat tcaggagtct ggtattgctg    1680
tcccagcttg tctcccttcg aggagaggtt gacacctgtc gtgaacacga cgaaatcctc    1740
ctcctccgaa ggagagctaa cttcagactg aacctcgccc aggtgacgcg tcgagacgaa    1800
tcccatcaca aacttcttat acttccgagc atagtcaaca gaagaagtag tatattgacc    1860
ggtagccaaa gatcccttgg atgtcatctc cgcaaggatc aaaaggcccc tctcagagcc    1920
gtagggaaag tcctcggccg aagcagtctg ggctagagcc tcgacgatac cctcaccggg    1980
cagaatactg cagttgatga tgtgggccca ctcggagatg cgcagagtgc cgccatggta    2040
ctgcttttgg actgtgtttc cgatatcgat gaacttgcga tcttcgaaga tgaggaaatt    2100
gtgcttctct gcaagggcct tcagaccggt gatggtctct tcgctgaaat cggagaggat    2160
atcgatgtga gttttgatca cggcaatgta cggaccgagt cctgttaaat aatccaccat    2220
taaccattat tagatcatta tgtaagtggc atccccggtg cgcatacggt cagccaaatc    2280
cagcagctct ttggtggttg tcacgtcggc cgaaacggtg acattggttt tcttggcctc    2340
ggcaacctca aagagcttct ttacgagggc attggggtgc ttgctagcgc gtgcactgta    2400
ggtcaattgc gacttggaag acatgttggc gatggagggg tagcgcgggg ttctgcaact    2460
atcgtagaaa tgagcactta gtggttgaaa ccggcttatt cagtagatta atacttgaag    2520
tttttagtaa tcagacagaa taatcaggat gtccaattac tacctcttaa tatgtggaat    2580
gaatgataga tataaattgt acgacaattg ccgcgaaaaa ttaaaatgga tctatggagg    2640
ggacagtcat gcactagcca cacgttcctc cgcctgtggg gtgagccaca tgcctcatct    2700
ggaccaaaca catcgatgca gtcacatgca gataagatta gggcctatcc ttagggtacc    2760
tgtccgcgcg gggattatgc ctggcttttt gcctgctttt gatatccttt caaggacata    2820
gcgataagtc caaccttatc ggccataata atgtcaatgc cagcagcggc ttgggcctag    2880
aatattccat cagctactga acaacttcta catcacaatt tgaaagctct aagaattaat    2940
atagaagcac ttaccttcgc attttctggt atattgttct gagatccata ggatcagctt    3000
atcgatgata agctgtcaaa catgagaatt c                                   3031
```

<210> SEQ ID NO 10
<211> LENGTH: 277
<212> TYPE: PRT
<213> ORGANISM: Artificial Sequence
<220> FEATURE:
<223> OTHER INFORMATION: fungal selection marker

<400> SEQUENCE: 10

Met Ser Ser Lys Ser Gln Leu Thr Tyr Ser Ala Arg Ala Ser Lys His
1               5                   10                  15

Pro Asn Ala Leu Val Lys Lys Leu Phe Glu Val Ala Glu Ala Lys Lys
            20                  25                  30

Thr Asn Val Thr Val Ser Ala Asp Val Thr Thr Lys Glu Leu Leu
        35                  40                  45

Asp Leu Ala Asp Arg Leu Gly Pro Tyr Ile Ala Val Ile Lys Thr His
    50                  55                  60

Ile Asp Ile Leu Ser Asp Phe Ser Glu Glu Thr Ile Thr Gly Leu Lys

```
                65                  70                  75                  80
Ala Leu Ala Glu Lys His Asn Phe Leu Ile Phe Glu Asp Arg Lys Phe
                        85                  90                  95

Ile Asp Ile Gly Asn Thr Val Gln Lys Gln Tyr His Gly Gly Thr Leu
                    100                 105                 110

Arg Ile Ser Glu Trp Ala His Ile Ile Asn Cys Ser Ile Leu Pro Gly
                115                 120                 125

Glu Gly Ile Val Glu Ala Leu Ala Gln Thr Ala Ser Ala Glu Asp Phe
            130                 135                 140

Pro Tyr Gly Ser Glu Arg Gly Leu Leu Ile Leu Ala Glu Met Thr Ser
145                 150                 155                 160

Lys Gly Ser Leu Ala Thr Gly Gln Tyr Thr Thr Ser Ser Val Asp Tyr
                165                 170                 175

Ala Arg Lys Tyr Lys Lys Phe Val Met Gly Phe Val Ser Thr Arg His
                180                 185                 190

Leu Gly Glu Val Gln Ser Glu Val Ser Ser Pro Ser Glu Glu Glu Asp
                195                 200                 205

Phe Val Val Phe Thr Thr Gly Val Asn Leu Ser Ser Lys Gly Asp Lys
            210                 215                 220

Leu Gly Gln Gln Tyr Gln Thr Pro Glu Ser Ala Val Gly Arg Gly Ala
225                 230                 235                 240

Asp Phe Ile Ile Ala Gly Arg Gly Ile Tyr Ala Ala Pro Asp Pro Val
                245                 250                 255

Glu Ala Ala Lys Arg Tyr Gln Lys Glu Gly Trp Asp Ala Tyr Leu Lys
                260                 265                 270

Arg Val Gly Ala Gln
                275

<210> SEQ ID NO 11
<211> LENGTH: 12699
<212> TYPE: DNA
<213> ORGANISM: Artificial Sequence
<220> FEATURE:
<223> OTHER INFORMATION: Vector

<400> SEQUENCE: 11
ccaccacagt gggatccgaa gcttggaatt cacgtgactt gaagtcatta ccctgttatc      60
cctatgattt aatagctcca tgtcaacaag aataaaacgc gttttcgggt ttacctcttc     120
cagatacagc tcatctgcaa tgcattaatg cattgactgc aacctagtaa cgccttcagg     180
ctccggcgaa gagaagaata gcttagcaga gctattttca ttttcgggag acagatcaa     240
gcagatcaac ggtcgtcaag agacctacga gactgaggaa tccgctcttg ctccacgcg     300
actatatatt tgtctctaat tgtactttga catgctcctc ttctttactc tgatagcttg     360
actatgaaaa ttccgtcacc agccctgggt tcgcaaagat aattgcatgt tcttccttg     420
aactctcaag cctacaggac acacattcat cgtaggtata aacctcgaaa tcattcctac     480
taagatggta tacaatagta accatggttg cctagtgaat gctccgtaac acccaatacg     540
ccggccgaaa cttttttaca actctcctat gagtcgttta cccagaatgc acaggtacac     600
ttgtttagag gtaatccttc tttctagaag tcctcgtgta ctgtgtaagc gcccactcca     660
catctccact cgagcctttt tcgagcgaac ctcccctgat ctcgaataat ctcatcgtca     720
tgcgcggtcc aacttctgct agttcggcat cctatatcc cgtcttaacg aaaacgtggt     780
gacgaacctc aatgctatcc tctttatta caaaggtgac cacgcggttt ccaacttttc     840
```

```
cagcttctcg gggagggaaa agatgcttca gaatttgaac cacgcgcttg cccagttttg    900
tcttgaaacc ctcaaagatc aagtgcgggt agctctctga cacagtcccg cgggcagcgt    960
tgggaatatc ggcacgtaga caacattat gcagggagaa gctggctgtc gggccatgag   1020
gaagatgtga gatcgtcatc gcagtagggg taccacggtg ttcggcggcc gcactgaccc   1080
tatagtgagt cgtattaatt taaatcatac caacatggtc aaataaaacg aaaggctcag   1140
tcgaaagact ggccgcccga tccacaggac gggtgtggtc gccatgatcg cgtagtcgat   1200
agtggctcca agtagcgaag cgagcaggac tgggcggcgg ccaaagcggt cggacagtgc   1260
tccgagaacg ggtgcgcata gaaattgcat caacgcatat agcgctagca gcacgccata   1320
gtgactggcg atgctgtcgg aatggacgat atcccgcaag aggcccggca gtaccggcat   1380
aaccaagcct atgcctacag catccagggt gacggtgccg aggatgacga tgagcgcatt   1440
gttagatttc atacacggtg cctgactgcg ttagcaattt aactgtgata aactaccgca   1500
ttaaagcttc gacatcaccc ttacccaaac tatatccaat gagcaaagaa taacgagtca   1560
aagcgggcgc attttcatc acatacgagt atgcacagtc aggactccac gtcatacatc   1620
aaaaacttgg aacgcatgag tctagctcag ctcggctctt ttccgatttt tgcgcagctt   1680
ctgttgcgga tcttgctgct tgtggagtct atgcccggc tgatgcattg aaacacaacg   1740
cgcagatgat ccaatcatac caaccagacg catcagcgcg tgtagctggg ggaagggtag   1800
gtggtgtagc ccagaaagcg acacggctgg cttttcaagaa gtttatcaac cctagacagc   1860
tttggagcgg atacccggct cttgtggcgc atagcttgcc agtgtcggcg atacagatgc   1920
ctctgtacga gacttttcgg tatcgaattt ctgaatatag attcggagat cgagagaagg   1980
tgctagaaag atcaagagat tatggaaaag aaacaggccc attcgacaat cggagaggct   2040
gcagcgacag ccgcgataag tgctgcagcc tcgggcggta tagccagtgt cttgacagca   2100
cccatggata tagtccggac acgaatcatg ctcgatgctg cagacacaac cgcacctcag   2160
aagaaaagga tgatcaatac cgtacgggag attatacgaa cagatggccc gagaggacta   2220
ttccgagggt gtgctatcaa cacgtttatg gccgctgtcg gatcagggtt atactttggt   2280
ctctacgaaa gcaccaaatg gtggctaggc tcggactcga tggataatag tgccatgtta   2340
gagtaagggg tgatgggaaa tcttgtatat aattgtgatt gtttgtacga tagtggccga   2400
ctgtacatta gtgataccc actcttagaa aatagaccaa tctccagctg cacccttcaga   2460
caatccgggt aaaaattctc gtctatgttg gagattggtg tgattttgaa acatgaccct   2520
tgactctgat cttgaatatg tccatatctc gaggcaggca tattattcat atagagaggg   2580
tatcccttag catcggtctg tcgtagtatc cgactgctga atttatgaat cgcatcatac   2640
ttgcgacata ctgccataaa aagagtacgt atccaccact acttattgcg caccaacacg   2700
cttcaggtat gcatcccatc cctctttctg gtaccgcttc gccgcctcca cgggatcagg   2760
agcagcataa attccacgac cagcaatgat aaagtcggca ccgcgtccaa cagcagattc   2820
aggagtctgg tattgctgtc ccagcttgtc tcccttcgag gagaggttga cacctgtcgt   2880
gaacacgacg aaatcctcct cctccgaagg agagctaact tcagactgaa cctcgcccag   2940
gtgacgcgtc gagacgaatc ccatcacaaa cttcttatac ttccgagcat agtcaacaga   3000
agaagtagta tattgaccgg tagccaaaga tcccttggat gtcatctccg caaggatcaa   3060
aaggcccctc tcagagccgt agggaaagtc ctcggccgaa gcagtctggg ctagagcctc   3120
gacgataccc tcaccgggca gaatactgca gttgatgatg tgggcccact cggagatgcg   3180
cagagtgccg ccatggtact gcttttggac tgtgtttccg atatcgatga acttgcgatc   3240
```

```
ttcgaagatg aggaaattgt gcttctctgc aagggccttc agaccggtga tggtctcttc    3300
gctgaaatcg gagaggatat cgatgtgagt tttgatcacg gcaatgtacg gaccgagtcc    3360
tgttaaataa tccaccatta accattatta gatcattatg taagtggcat ccccggtgcg    3420
catacggtca gccaaatcca gcagctcttt ggtggttgtc acgtcggccg aaacggtgac    3480
attggttttc ttggcctcgg caacctcaaa gagcttcttt acgagggcat tggggtgctt    3540
gctagcgcgt gcactgtagg tcaattgcga cttggaagac atgttggcga tggagggggta   3600 gcgcggggtt ctgcaactat cgtagaaatg agcacttagt ggttgaaacc ggcttattca    3660
gtagattaat acttgaagtt tttagtaatc agacagaata atcaggatgt ccaattacta    3720
cctcttaata tgtggaatga atgatagata taaattgtac gacaattgcc gcgaaaaatt    3780
aaaatggatc tatggagggg acagtcatgc actagccaca cgttcctccg cctgtggggt    3840
gagccacatg cctcatctgg accaaacaca tcgatgcagt cacatgcaga taagattagg    3900
gcctatcctt agggtacctg tccgcgcggg gattatgcct ggcttttgc ctgcttttga     3960 tatcctttca aggacatagc gataagtcca accttatcgg ccataataat gtcaatgcca    4020
gcagcggctt gggcctagaa tattccatca gctactgaac aacttctaca tcacaatttg    4080
aaagctctaa gaattaatat agaagcactt accttcgcat tttctggtat attgttctga    4140
gatccatagg atcagcttat cgatgataag ctgtcaaaca tgagaattcg gccgtcgac     4200 caattctcat gtttgacagc ttatcatcga atttctgcca ttcatccgct tattatcact    4260
tattcaggcg tagcaaccag gcgtttaagg gcaccaataa ctgccttaaa aaaagtcgag    4320
gctgatcagc gagctctaga gaattgatcc cctcagaaga actcgtcaag aaggcgatag    4380
aaggcgatgc gctgcgaatc gggagcggcg ataccgtaaa gcacgaggaa gcggtcagcc    4440
cattcgccgc caagctcttc agcaatatca cgggtagcca acgctatgtc ctgatagcgg    4500
tccgccacac ccagccggcc acagtcgatg aatccagaaa agcggccatt ttccaccatg    4560
atattcggca agcaggcatc gccatgggtc acgacgagat catcgccgtc gggcatgcgc    4620
gccttgagcc tggcgaacag ttcggctggc gcgagcccct gatgctcttc gtccagatca    4680
tcctgatcga caagaccggc ttccatccga gtacgtgctc gctcgatgcg atgtttcgct    4740
tggtggtcga tgggcaggt agccggatca agcgtatgca gccgccgcat tgcatcagcc    4800
atgatggata ctttctcggc aggagcaagg tgagatgaca ggagatcctg ccccggcact    4860
tcgcccaata gcagccagtc ccttcccgct tcagtgacaa cgtcgagcac agctgcgcaa    4920
ggaacgcccg tcgtggccag ccacgatagc cgcgctgcct cgtcctgcag ttcattcagg    4980
gcaccggaca ggtcggtctt gacaaaaaga accgggcgcc cctgcgctga cagccggaac    5040
acggcggcat cagagcagcc gattgtctgt tgtgcccagt catagccgaa tagcctctcc    5100
acccaagcgg ccggagaacc tgcgtgcaat ccatcttgtt caatggccga tcccatggtt    5160
tagttcctca ccttgtcgta ttatactatg ccgatatact atgccgatga ttaattgtca    5220
acaggctgca ggtcgtttag cttccttagc tcctgaaaat ctcgataact caaaaaatac    5280
gcccggtagt gatcttattt cattatggtg aaagttggaa cctcttacgt gccgatcaac    5340
gtctcatttt cgccaaaagt tggcccaggg cttcccggta tcaacaggga caccaggatt    5400
tatttattct gcgaagtgat cttccgtcac aggtatttat tcgcgataag ctcatggagc    5460
ggcgtaaccg tcgcacagga aggacagaga aagcgcggat ctgggaagtg acggacagaa    5520
cggtcaggac ctggattggg gaggcggttg ccgccgctgc tgctgacggt gtgacgttct    5580
```

```
ctgttccggt cacaccacat acgttccgcc attcctatgc gatgcacatg ctgtatgccg    5640
gtataccgct gaaagttctg caaagcctga tgggacataa gtccatcagt tcaacggaag    5700
tctacacgaa ggttttttgcg ctggatgtgg ctgcccggca ccgggtgcag tttgcgatgc   5760
cggagtctga tgcggttgcg atgctgaaac aattatcctg agaataaatg ccttggcctt    5820
tatatggaaa tgtggaactg agtggatatg ctgttttttgt ctgttaaaca gagaagctgg   5880
ctgttatcca ctgagaagcg aacgaaacag tcgggaaaat ctcccattat cgtagagatc    5940
cgcattatta atctcaggag cctgtgtagc gtttatagga agtagtgttc tgtcatgatg    6000
cctgcaagcg gtaacgaaaa cgatttgaat atgccttcag gaacaataga aatcttcgtg    6060
cggtgttacg ttgaagtgga gcggattatg tcagcaatgg acagaacaac ctaatgaaca    6120
cagaaccatg atgtggtctg tccttttaca gccagtagtg ctcgccgcag tcgagcgaca    6180
gggcgaagcc cctggttgcc ctcgccgctg ggctggcggc cgtctatggc cctgcaaacg    6240
cgccagaaac gccgtcgaag ccgtgtgcga gacaccgcgg ccggccgccg gcgttgtgga    6300
tacctcgcgg aaaacttggc cctcactgac agatgagggg cggacgttga cacttgaggg    6360
gccgactcac ccggcgcggc gttgacagat gaggggcagg ctcgatttcg gccggcgacg    6420
tggagctggc cagcctcgca aatcggcgaa aacgcctgat tttacgcgag tttcccacag    6480
atgatgtgga caagcctggg gataagtgcc ctgcggtatt gacacttgag gggcgcgact    6540
actgacagat gaggggcgcg atccttgaca cttgagggggc agagtgctga cagatgaggg    6600
gcgcacctat tgacatttga ggggctgtcc acaggcagaa aatccagcat ttgcaagggt    6660
ttccgcccgt ttttcggcca ccgctaacct gtcttttaac ctgcttttaa accaatattt    6720
ataaaccttg ttttttaacca gggctgcgcc ctgtgcgcgt gaccgcgcac gccgaagggg    6780
ggtgcccccc cttctcgaac cctcccggtc gagtgagcga ggaagcacca gggaacagca    6840
cttatatatt ctgcttacac acgatgcctg aaaaaacttc ccttggggtt atccacttat    6900
ccacggggat attttttataa ttattttttt tatagttttt agatcttctt ttttagagcg    6960
ccttgtaggc ctttatccat gctggttcta gagaaggtgt tgtgacaaat tgccctttca    7020
gtgtgacaaa tcaccctcaa atgacagtcc tgtctgtgac aaattgccct taaccctgtg    7080
acaaattgcc ctcagaagaa gctgttttttt cacaaagtta tccctgctta ttgactcttt    7140
tttatttagt gtgacaatct aaaaacttgt cacacttcac atggatctgt catggcggaa    7200
acagcggtta tcaatcacaa gaaacgtaaa aatagcccgc gaatcgtcca gtcaaacgac    7260
ctcactgagg cggcatatag tctctcccgg gatcaaaaac gtatgctgta tctgttcgtt    7320
gaccagatca gaaaatctga tggcaccctca caggaacatg acggtatctg cgagatccat    7380
gttgctaaat atgctgaaat attcggattg acctctgcgg aagccagtaa ggatatacgg    7440
caggcattga agagtttcgc ggggaaggaa gtggtttttt atcgccctga agaggatgcc    7500
ggcgatgaaa aaggctatga atcttttcct tggtttatca aacgtgcgca cagtccatcc    7560
agagggcttt acagtgtaca tatcaaccca tatctcattc ccttctttat cgggttacag    7620
aaccggttta cgcagtttcg gcttagtgaa acaaaagaaa tcaccaatcc gtatgccatg    7680
cgtttatacg aatccctgtg tcagtatcgt aagccggatg ctcaggcat cgtctctctg    7740
aaaatcgact ggatcataga gcgttaccag ctgcctcaaa gttaccagcg tatgcctgac    7800
ttccgccgcc gcttcctgca ggtctgtgtt aatgagatca acagcagaac tccaatgcgc    7860
ctctcataca ttgagaaaaa gaaaggccgc cagacgactg atatcgtatt ttccttccgc    7920
gatatcactt ccatgacgac aggataggct agtgataata agtgactgag gtatgtgctc    7980
```

```
ttcttatctc cttttgtagt gttgctctta ttttaaacaa ctttgcggtt ttttgatgac    8040
tttgcgattt tgttgttgct ttgcagtaaa ttgcaagatt taataaaaaa acgcaaagca    8100
atgattaaag gatgttcaga atgaaactca tggaaacact taaccagtgc ataaacgctg    8160
gtcatgaaat gacgaaggct atcgccattg cacagtttaa tgatgacagc ccggaagcga    8220
ggaaaataac ccggcgctgg agaataggtg aagcagcgga tttagttggg gtttcttctc    8280
aggctatcag agatgccgag aaagcagggc gactaccgca cccggatatg gaaattcgag    8340
gacgggttga gcaacgtgtt ggttatacaa ttgaacaaat taatcatatg cgtgatgtgt    8400
ttggtacgcg attgcgacgt gctgaagacg tatttccacc ggtgatcggg gttgctgccc    8460
ataaagaaag gtggcgttta caaaacctca gtttctgttc atcttgctca ggatctggct    8520
ctgaaggggc tacgtgtttt gctcgtggaa ggtaacgacc cccagggaac agcctcaatg    8580
tatcacggat gggtaccaga tcttcatatt catgcagaag acactctcct gcctttctat    8640
cttggggaaa aggacgatgt cacttatgca ataaagccca cttgctggcc ggggcttgac    8700
attattcctt cctgtctggc tctgcaccgt attgaaactg agttaatggg caaatttgat    8760
gaaggtaaac tgcccaccga tccacacctg atgctccgac tggccattga aactgttgct    8820
catgactatg atgtcatagt tattgacagc gcgcctaacc tgggtatcgg cacgattaat    8880
gtcgtatgtg ctgctgatgt gctgattgtt cccacgcctg ctgagttgtt tgactacacc    8940
tccgcactgc agttttttcga tatgcttcgt gatctgctca agaacgttga tcttaaaggg    9000
ttcgagcctg atgtacgtat tttgcttacc aaatacagca atagtaatgg ctctcagtcc    9060
ccgtggatgg aggagcaaat tcgggatgcc tggggaagca tggttctaaa aatgttgta    9120 cgtgaaacgg atgaagttgg taaaggtcag atccggatga aactgttttt tgaacaggcc    9180
attgatcaac gctcttcaac tggtgcctgg agaaatgctc tttctatttg ggaacctgtc    9240
tgcaatgaaa ttttcgatcg tctgattaaa ccacgctggg agattagata atgaagcgtg    9300
cgcctgttat tccaaaacat acgctcaata ctcaaccggt tgaagatact tcgttatcga    9360
caccagctgc cccgatggtg gattcgttaa ttgcgcgcgt aggagtaatg gctcgcggta    9420
atgccattac tttgcctgta tgtggtcggg atgtgaagtt tactcttgaa gtgctccggg    9480
gtgatagtgt tgagaagacc tctcgggtat ggtcaggtaa tgaacgtgac caggagctgc    9540
ttactgagga cgcactggat gatctcatcc cttcttttct actgactggt caacagacac    9600
cggcgttcgg tcgaagagta tctggtgtca tagaaattgc cgatgggagt cgccgtcgta    9660
aagctgctga cttaccgaa agtgattatc gtgttctggt tggcgagctg gatgatgagc    9720
agatggctgc attatccaga ttgggtaacg attatcgccc aacaagtgct tatgaacgtg    9780
gtcagcgtta tgcaagccga ttgcagaatg aatttgctgg aaatatttct gcgctggctg    9840
atgcggaaaa tatttcacgt aagattatta cccgctgtat caacaccgcc aaattgccta    9900
aatcagttgt tgctctttt tctcaccccg gtgaactatc tgcccggtca ggtgatgcac    9960
ttcaaaaagc ctttacagat aaagaggaat tacttaagca gcaggcatct aaccttcatg   10020
agcagaaaaa agctggggtg atatttgaag ctgaagaagt tatcactctt ttaacttctg   10080
tgcttaaaac gtcatctgca tcaagaacta gtttaagctc acgacatcag tttgctcctg   10140
gagcgacagt attgtataag ggcgataaaa tggtgcttaa cctggacagg tctcgtgttc   10200
caactgagtg tatagagaaa attgaggcca ttccttaagga acttgaaaag ccagcaccct   10260
gatgcgacca cgttttagtc tacgtttatc tgtctttact taatgtcctt tgttacaggc   10320
```

```
cagaaagcat aactggcctg aatattctct ctgggcccac tgttccactt gtatcgtcgg    10380
tctgataatc agactgggac cacggtccca ctcgtatcgt cggtctgatt attagtctgg    10440
gaccacggtc ccactcgtat cgtcggtctg attattagtc tgggaccacg gtcccactcg    10500
tatcgtcggt ctgataatca gactgggacc acggtccac tcgtatcgtc ggtctgatta    10560
ttagtctggg accatggtcc cactcgtatc gtcggtctga ttattagtct gggaccacgg    10620
tcccactcgt atcgtcggtc tgattattag tctggaacca cggtcccact cgtatcgtcg    10680
gtctgattat tagtctggga ccacggtccc actcgtatcg tcggtctgat tattagtctg    10740
ggaccacgat cccactcgtg ttgtcggtct gattatcggt ctgggaccac ggtcccactt    10800
gtattgtcga tcagactatc agcgtgagac tacgattcca tcaatgcctg tcaagggcaa    10860
gtattgacat gtcgtcgtaa cctgtagaac ggagtaacct cggtgtgcgg ttgtatgcct    10920
gctgtggatt gctgctgtgt cctgcttatc cacaacattt tgcgcacggt tatgtggaca    10980
aaatacctgg ttacccaggc cgtgccggca cgttaaccgg gctgcatccg atgcaagtgt    11040
gtcgctgtcg acgagctcgc gagctcggac atgaggttgc cccgtattca gtgtcgctga    11100
tttgtattgt ctgaagttgt ttttacgtta agttgatgca gatcaattaa tacgatacct    11160
gcgtcataat tgattatttg acgtggtttg atggcctcca cgcacgttgt gatatgtaga    11220
tgataatcat tatcactttta cgggtccttt ccggtgatcc gacaggttac ggggcggcga    11280
cctcgcgggt tttcgctatt tatgaaaatt ttccggttta aggcgtttcc gttcttcttc    11340
gtcataactt aatgttttta tttaaaatac cctctgaaaa gaaaggaaac gacaggtgct    11400
gaaagcgagc tttttggcct ctgtcgtttc ctttctctgt ttttgtccgt ggaatgaaca    11460
atggaagtcc gagctcatcg ctaataactt cgtatagcat acattatacg aagttatatt    11520
cgatgcggcc aaggtgagcc agtgtgatta catttgcggc ctaactgtgg ccagtccagt    11580
tacgctggag tcactagtat ttaggtgaca ctatagaagc ggccgcgaat tcatgccagt    11640
tgttccagtg atcttcgttt cgaagatgga catccaattt gtgcaagtta ttcggcctac    11700
ctggctgtgg ccgaggcagc gttatcatga ccgtcgctgt tcaaagataa ggcgagaagt    11760
ttgcgggctg tcttgacgat atggcttcgt tcagacagat atagttcccg gagtcgcagg    11820
ctgctattct tctccgaaac aaactcggct gcactgtttc catcaccggg tctggcgttt    11880
gaggatgtca gcgaaactcg gccgcaagtg acaccgaaaa gtatcgactc cggtgcccgt    11940
ttcaagctag tggcttcctc aacagcgagt cggccaggag acgtgaagca ggacgggttg    12000
ccatccagac cgtgaccgaa cgcgttgatt tcatcaatcc cagccttttc gctcaaccaa    12060
agagcatcgg ctttgatttc cttcaggtca tacgaggctt gtgcaatggt ctccgcatgg    12120
atatcgcgtg ctgttctcct atcaactcgg aattttgtct tagggatgg cgtaggaacc    12180
tcgaatgctg atcaggatgt gacaaaaacg actcgaaaac ccgggttcat cggtgtgctt    12240
tcgggatcgc aagcgtaaag aaagattcac tcttccaaga cctagaagta tagcaaatca    12300
gcagcagacc atcaatgtat agcgaatgcg cccatacaaa acgtgaactc cccggagaag    12360
cactttgtcc agggacggga ataggcttc cggaacggga gcattggcag cacagctata    12420
tcattctaag taaacaaatg taatgagcaa gcggacgagt gctgaaacct cctatgccgt    12480
gaaggccgac gaaagcgcgt tgttggatta agtcgacaga agatgatatt gaaggagcat    12540
ttttgggctt ggctggagct agtggaggtc aacacatcaa tgctattttg gtttagtcgt    12600
ccaggcggat cacaaaattt gtgtcgtttg acataggat aacagggtaa tgacaacttg    12660
tccacgtgga attctaagct taggatccca ctgtggtgg                           12699
```

<210> SEQ ID NO 12
<211> LENGTH: 1000
<212> TYPE: DNA
<213> ORGANISM: Artificial Sequence
<220> FEATURE:
<223> OTHER INFORMATION: 3' A. nidulans trpC gene homologous region

<400> SEQUENCE: 12

```
tgatttaata gctccatgtc aacaagaata aaacgcgttt tcgggtttac ctcttccaga      60
tacagctcat ctgcaatgca ttaatgcatt gactgcaacc tagtaacgcc ttcaggctcc     120
ggcgaagaga agaatagctt agcagagcta ttttcatttt cgggagacga gatcaagcag     180
atcaacggtc gtcaagagac ctacgagact gaggaatccg ctcttggctc cacgcgacta     240
tatatttgtc tctaattgta ctttgacatg ctcctcttct ttactctgat agcttgacta     300
tgaaaattcc gtcaccagcc ctgggttcgc aaagataatt gcatgtttct tccttgaact     360
ctcaagccta caggacacac attcatcgta ggtataaacc tcgaaatcat tcctactaag     420
atggtataca atagtaacca tggttgccta gtgaatgctc cgtaacaccc aatacgccgg     480
ccgaaacttt tttacaactc tcctatgagt cgtttaccca gaatgcacag gtacacttgt     540
ttagaggtaa tccttctttc tagaagtcct cgtgtactgt gtaagcgccc actccacatc     600
tccactcgag cctttttcga gcgaacctcc cctgatctcg aataatctca tcgtcatgcg     660
cggtccaact tctgctagtt cggcatcctt atatcccgtc ttaacgaaaa cgtggtgacg     720
aacctcaatg ctatcctctt tatttacaaa ggtgaccacg cggttttcaa cttttccagc     780
ttctcgggga gggaaaagat gcttcagaat ttgaaccacg cgcttgccca gttttgtctt     840
gaaaccctca agatcaagt  gcgggtagct ctctgacaca gtcccgcggg cagcgttggg     900
aatatcggca cgtagaacaa cattatgcag ggagaagctg gctgtcgggc catgaggaag     960
atgtgagatc gtcatcgcag tagggggtacc acggtgttcg                         1000
```

<210> SEQ ID NO 13
<211> LENGTH: 1007
<212> TYPE: DNA
<213> ORGANISM: Artificial Sequence
<220> FEATURE:
<223> OTHER INFORMATION: 5' of A. nidulans trpC gene

<400> SEQUENCE: 13

```
gaattcatgc cagttgttcc agtgatcttc gtttcgaaga tggacatcca atttgtgcaa      60
gttattcggc ctacctggct gtggccgagg cagcgttatc atgaccgtcg ctgttcaaag     120
ataaggcgag aagtttgcgg gctgtcttga cgatatggct tcgttcagac agatatagtt     180
cccggagtcg caggctgcta ttcttctccg aaacaaactc ggctgcactg tttccatcac     240
cgggtctggc gtttgaggat gtcagcgaaa ctcggccgca agtgacaccg aaaagtatcg     300
actccggtgc ccgtttcaag ctagtggctt cctcaacagc gagtcggcca ggagacgtga     360
agcaggacgg gttgccatcc agaccgtgac cgaacgcgtt gatttcatca tcccagcct      420
tttcgctcaa ccaaagagca tcggctttga tttccttcag gtcatacgag gcttgtgcaa     480
tggtctccgc atggatatcg cgtgctgttc tcctatcaac tcggaatttt gtcttagggg     540
atggcgtagg aacctcgaat gctgatcagg atgtgacaaa aacgactcga aacccgggt      600
tcatcggtgt gctttcggga tcgcaagcgt aagaaaagat tcactcttcc aagacctaga     660
agtatagcaa atcagcagca gaccatcaat gtatagcgaa tgcgcccata caaaacgtga     720
```

| | |
|---|---|
| actccccgga gaagcacttt gtccagggac gggaaatagg cttccggaac gggagcattg | 780 |
| gcagcacagc tatatcattc taagtaaaca aatgtaatga gcaagcggac gagtgctgaa | 840 |
| acctcctatg ccgtgaaggc cgacgaaagc gcgttgttgg attaagtcga cagaagatga | 900 |
| tattgaagga gcattttttgg gcttggctgg agctagtgga ggtcaacaca tcaatgctat | 960 |
| tttggtttag tcgtccaggc ggatcacaaa atttgtgtcg tttgaca | 1007 |

<210> SEQ ID NO 14
<211> LENGTH: 17997
<212> TYPE: DNA
<213> ORGANISM: Artificial Sequence
<220> FEATURE:
<223> OTHER INFORMATION: Vector

<400> SEQUENCE: 14

| | |
|---|---|
| ccaccacagt gggatccgaa gcttggaatt cacgtgactt gaagtcatta ccctgttatc | 60 |
| cctagcggcc gctctagaac tagtggatct caggctgcca cgtcttcagt gccgtcctgc | 120 |
| gcatcatcct catcgtcgtc tgtagggggc ttcgcccatg taatgaaagc gcgcttctcg | 180 |
| atgggcgttc cctggccccg cctgttgta gatttggtta cgacaatctt gtccacaaac | 240 |
| aagccaacga agacccttttt gtcatctaca ctcgctctac cccaccatga tttcggccca | 300 |
| gtagggtctg catccgcatc ttccgggaac cactggtcca gcggcagctt cggagcctcc | 360 |
| gcggcctcca gctcggccaa tcttttcctcg caccctgct gacgcagggt gagcgcagct | 420 |
| tgctgtttac ggaagtgctt gcgccccact gggccgtcgt acgcgcccgc agctcgatcc | 480 |
| tcatacagct cttcaagagc attcagtgcg tcggctctct ctgcaacgag gttggctcgt | 540 |
| tcgcccgact tctcaggggc ctcggtgagt ttaccgaatc ttctagcagc ctcccacagc | 600 |
| agggccaggt tctcctcgtc gccttccgca tgccttatct tgttgaagat ccgctcagca | 660 |
| acaaacttat ccaatgcagc catagaaaca ttacaggttc cctcgtgctg tccaggagcg | 720 |
| gaggggtcaa caaccttccg gcggcggcag cgataagagt ccttgatact ttcctccccct | 780 |
| ctcttcgatg tcataacagc gccgcattca cagtacaatt tatccattgc gctgagaatc | 840 |
| gcctgaccac gactgagacc cttcccccgt cctcggccat ccagccacgc tgcagctca | 900 |
| taccactcag ccggttctat aatggggccg caatccagtt caaccggtcg tagagtgatt | 960 |
| ggatcgcgtt gaattctgta cccctcgatc ttcgttgtcg gtgtgccatc gggcttcttc | 1020 |
| ttataaatca cctcagcggc aaagccggcg atcctaggat cccgcagaat cctcatgaca | 1080 |
| gtcgcgggat cccaggcaga cgaagcagtt ttcttcccaa tggtctcgcc gcgcgtcggt | 1140 |
| acggcatctg cgtccatgcg cttgcagagg ccggtaatgc tccccgggtg gatggcagcc | 1200 |
| tgtgagccag gcttaaaggg caagtgcttg tgagtcttga tctctcgcca ccaccatcgt | 1260 |
| attacatcag gctcaaattc gaaagggccg gtcagtggtg tggtcgaatg tgccaatttg | 1320 |
| ttaatcacta cgttcaccat gcgaccattc cttgtaatct ccttcgtttc gaaaccagt | 1380 |
| tcgaagccat aagggggcctt ccccccccaca taacctccca attcccttttg aaggttcttt | 1440 |
| gtatccagga tcttagcgga tttgagggaa gattccttgt gtgatgcatc cagccgcata | 1500 |
| attagatgaa tcaagtccat cacgttgccc tggcggaaga ccccttcttg cgtcgaaacg | 1560 |
| atagtgacgc ccagggcgag caactctgag acgatcggaa tagcatccat aaccttcagc | 1620 |
| ctgctgaagc gagaaacatc atatacaata atcatattga gtcttccgc cctgcattca | 1680 |
| ttgagaatcc gctcaaactc agggcgttcg gcggtgccaa aggcgctggt gcctggggcc | 1740 |
| tctgaaaaat ggccaacaaa tctaaatctc ccgccatccc gctccacctc gcgctgaagg | 1800 |

```
tcagcggcct tgtcttcatt ggcagagcgc tgggtggctg gcgaagctgc agagctgttc    1860
tcgcgttccc tcgactgtcg gtcgtacgct ccggcatagg tatctacacc tgtgactacg    1920
ccttgtgtca ttttgaggcg aggtgatagg attggaagag ttctaattaa ctgagtagag    1980
aactgttgat tgttggttga tgatgttggt gagactgaga accttggggg tctttatata    2040
gatgttcagc tatgcgggga tgcgatcctg ggtaggaga gcacgtacgg ggccccgctc     2100
gtttgtggct ctccgtgcgg acatcccgtg cggacagtac cagaaagtgc tccgtctctg    2160
ctctatacgg ctctatacgc gtacctcttg aacggtgcgt ggagaggagt ggtgtgtcaa    2220
tttccgcccc gccctcgtgc ggttccgcat gcatccaatc ctaggtcgga actatcccga    2280
gctgcggatg ccgatgcgga cggacaagtg ggaactatca caatcagctt ttcagctggg    2340
ggttattgga tggtagctcc acacaggcgg agaaatacga agggacttac agtgttccgg    2400
ccgtgtcaaa gtgtctgtcg gcgaccctac gcccccaact gagagaactc aaaggttacc    2460
ccagttgggg cagcttattt tttgtatact gttttgtgat agcacgaagt ttttccacgg    2520
tatcttgtta aaaatatata tttgtggcgg gcttacctac atcaaattaa taagagacta    2580
attataaact aaacacacaa gcaagctact ttagggtaaa agtttataaa tgcttttgac    2640
gtataaacgt tgcttgtatt tattattaca attaaaggtg gatagaaaac ctagagacta    2700
gttagaaact aatctcaggt ttgcgttaaa ctaaatcaga gcccgagagg ttaacagaac    2760
ctagaagggg actagatatc cgggtaggga aacaaaaaaa aaaaacaaga cagccacata    2820
ttagggagac tagttagaag ctagttccag gactaggaaa ataaaagaca atgataccac    2880
agtctagttg acaactagat agattctaga ttgaggccaa agtctctgag atccaggtta    2940
gttgcaacta atactagtta gtatctagtc tcctataact ctgaagctag ataaacttac    3000
tactattatc ctcaccactg ttcagctgcg caaacggagt gattgcaagg tgttcagaga    3060
ctagttattg actagtcagt gactagcaat aactaacaag gtattaaccct accatgtctg    3120 ccatcaccct gcacttcctc gggctcagca gccttttcct cctcattttc atgctcattt    3180
tccttgttta agactgtgac tagtcaaaga ctagtccaga accacaaagg agaaatgtct    3240
taccactttc ttcattgctt gtctcttttg cattatccat gtctgcaact agttagagtc    3300
tagttagtga ctagtccgac gaggacttgc ttgtctccgg attgttggag gaactctcca    3360
gggcctcaag atccacaaca gagccttcta gaagactggt caataactag ttggtctttg    3420
tctgagtctg acttacgagg ttgcatactc gctccctttg cctcgtcaat cgatgagaaa    3480
aagcgccaaa actcgcaata tggctttgaa ccacacggtg ctgagactag ttagaatcta    3540
gtcccaaact agcttggata gcttaccttt gcccctttgcg ttgcgacagg tcttgcaggg    3600 tatgttcct ttctcaccag ctgatttagc tgccttgcta ccctcacggc ggatctgcat     3660
aaagagtggc tagaggttat aaattagcac tgatcctagg tacgggctg aatgtaactt     3720 gcctttcctt tctcatcgcg cggcaagaca ggcttgctca aattcctacc agtcacaggg    3780
gtatgcacgg cgtacggacc acttgaacta gtcacagatt agttagcaac tagtctgcat    3840
tgaatggctg tacttacggg ccctcgccat tgtcctgatc atttccagct tcaccctcgt    3900
tgctgcaaag tagttagtga ctagtcaagg actagtgaa atgggagaag aaactcacga    3960
attctcgaca cccttagtat tgtggtcctt ggacttggtg ctgctatata ttagctaata    4020
cactagttag actcacagaa acttacgcag ctcgcttgcg cttcttggta ggagtcgggg    4080
ttgggagaac agtgccttca acaagccctt cataccatgc tacttgacta gtcagggact    4140
```

```
agtcaccaag taatctagat aggacttgcc tttggcctcc atcagttcct tcatagtggg      4200
aggtccattg tgcaatgtaa actccatgcc gtgggagttc ttgtccttca agtgcttgac      4260
caatatgttt ctgttggcag agggaacctg tcaactagtt aataactagt cagaaactag      4320
tatagcagta gactcactgt acgcttgagg catcccttca ctcggcagta gacttcatat      4380
ggatggatat caggcacgcc attgtcgtcc tgtggactag tcagtaacta ggcttaaagc      4440
tagtcgggtc ggcttactat cttgaaatcc ggcagcgtaa gctccccgtc cttaactgcc      4500
tcgagatagt gacagtactc tggggacttt cggagatcgt tatcgcgaat gctcggcata      4560
ctaatcgttg actagtcttg gactagtccc gagcaaaaag gattggagga ggaggaggaa      4620
ggtgagagtg agacaaagag cgaaataaga gcttcaaagg ctatctctaa gcagtatgaa      4680
ggttaagtat ctagttcttg actagattta aaagagattt cgactagtta tgtacctgga      4740
gtttggatat aggaatgtgt tgtggtaacg aaatgtaagg gggaggaaag aaaaagtcgg      4800
tcaagaggta actctaagtc ggccattcct ttttgggagg cgctaaccat aaacggcatg      4860
gtcgacttag agttagctca gggaatttag ggagttatct gcgaccaccg aggaacggcg      4920
gaatgccaaa gaatcccgat ggagctctag ctggcggttg acaaccccac cttttggcgt      4980
ttctgcggcg ttgcaggcgg gactggatac ttcgtagaac cagaaaggca aggcagaacg      5040
cgctcagcaa gagtgttgga agtgatagca tgatgtgcct tgttaactag gtcaaaatct      5100
gcaggtatgc ttgatgttat ccaaagtgtg agagaggaag gtccaaacat acacgattgg      5160
gagagggcct aggtataaga gtttttgagt agaacgcatg tgagcccagc catctcgagg      5220
agattaaaca cgggccggca tttgatggct atgttagtac cccaatggaa agcctgagag      5280
tccagtggtc gcagataact ccctaaattc cctgagctaa ctctaagtcg accatgccgt      5340
ttatggttag cgcctcccaa aaaggaatgg ccgacttaga gttacctctt gaccgacttt      5400
ttctttcctc ccccttacat ttcgttacca caacacattc ctatatccaa actccaggta      5460
cataactagt cgaaatctct tttaaatcta gtcaagaact agatacttaa ccttcatact      5520
gcttagagat agcctttgaa gctcttattt cgctctttgt ctcactctca ccttcctcct      5580
cctcctccaa tcctttttgc tcgggactag tccaagacta gtcaacgatt agtatgccga      5640
gcattcgcga taacgatctc cgaaagtccc cagagtactg tcactatctc gaggcagtta      5700
aggacgggga gcttacgctg ccggatttca agatagtaag ccgacccgac tagctttaag      5760
cctagttact gactagtcca caggacgaca atggcgtgcc tgatatccat ccatatgaag      5820
tctactgccg agtgaaggga tgcctcaagc gtacagtgag tctactgcta tactagtttc      5880
tgactagtta ttaactagtt gacaggttcc ctctgccaac agaaacatat tggtcaagca      5940
cttgaaggac aagaactccc acggcatgga gtttacattg cacaatggac ctcccactat      6000
gaaggaactg atggaggcca aaggcaagtc ctatctagat tacttggtga ctagtccctg      6060
actagtcaag tagcatggta tgaaggcttg tttgaaggca ctgttctccc aacccccgact      6120 cctaccaaga agcgcaagcg agctgcgtaa gtttctgtga gtctaactag tgtattagct      6180
aatatatagc agcaccaagt ccaaggacca caatactaag ggtgtcgaga attcgtgagt      6240
ttcttctccc atttcaacta gtccttgact agtcactaac tactttgcag caacgagggt      6300
gaagctggaa atgatcagga caatggcgag ggcccgtaag tacagccatt caatgcagac      6360
tagttgctaa ctaatctgtg actagttcaa gtggtccgta cgccgtgcat acccctgtga      6420
ctggtaggaa tttgagcaag cctgtcttgc cgcgcgatga gaaaggaaag gcaagttaca      6480
ttcagccccg tacctaggat cagtgctaat ttataaccct agccactct ttatgcagat      6540
```

```
ccgccgtgag ggtagcaagg cagctaaatc agctggtgag aaaggaacca taccctgcaa    6600
gacctgtcgc aacgcaaagg gcaaaggtaa gctatccaag ctagtttggg actagattct    6660
aactagtctc agcaccgtgt ggttcaaagc catattgcga gttttggcgc tttttctcat    6720
cgattgacga ggcaaaggga gcgagtatgc aacctcgtaa gtcagactca gacaaagacc    6780
aactagttat tgaccagtct tctagaaggc tctgttgtgg atcttgaggc cctggagagt    6840
tcctccaaca atccggagac aagcaagtcc tcgtcggact agtcactaac tagactctaa    6900
ctagttgcag acatggataa tgcaaaagag acaagcaatg aagaaagtgg taagacattt    6960
ctcctttgtg gttctggact agtctttgac tagtcacagt cttaaacaag aaaatgagc    7020 atgaaaatga ggaggaaaag gctgctgagc ccgaggaagt gcagggtgat ggcagacatg    7080
gtaggttaat accttgttag ttattgctag tcactgacta gtcaataact agtctctgaa    7140
caccttgcaa tcactccgtt tgcgcagctg aacagtggtg aggataatag tagtaagtta    7200
ttctagcttc agagttatag gagactagat actaactagt attagttgca actaacctgg    7260
atctcagaga cttttggcctc aatctagaat ctatctagtt gtcaactaga ctgtggtatc    7320
attgtctttt attttcctag tcctggaact agcttctaac tagtctccct aatatgtggc    7380
tgtcttgttt ttttttttg tttccctacc cggatatcta gtccccttct aggttctgtt    7440
aacctctcgg gctctgattt agtttaacgc aaacctgaga ttagtttcta actagtctct    7500
aggttttcta tccaccttta attgtaataa taaatacaag caacgtttat acgtcaaaag    7560
catttataaa cttttaccct aaagtagctt gcttgtgtgt ttagtttata attagtctct    7620
tattaatttg atgtaggtaa gcccgccaca aatatatatt tttaacaaga taccgtggaa    7680
aaacttcgtg ctatcacaaa acagtataca aaaataagc tgatccacag gacgggtgtg    7740
gtcgccatga tcgcgtagtc gatagtggct ccaagtagcg aagcgagcag gactgggcgg    7800
cggccaaagc ggtcggacag tgctccgaga acgggtgcgc atagaaattg catcaacgca    7860
tatagcgcta gcagcacgcc atagtgactg gcgatgctgt cggaatggac gatatcccgc    7920
aagaggcccg gcagtaccgg cataaccaag cctatgccta cagcatccag ggtgacggtg    7980
ccgaggatga cgatgagcgc attgttagat ttcatacacg gtgcctgact gcgttagcaa    8040
tttaactgtg ataaactacc gcattaaagc ttcgacatca cccttaccca aactatatcc    8100
aatgagcaaa gaataacgag tcaaagcggg cgcattttc atcacatacg agtatgcaca    8160
gtcaggactc cacgtcatac atcaaaaact tggaacgcat gagtctagct cagctcggct    8220
cttttccgat ttttgcgcag cttctgttgc ggatcttgct gcttgtggag tctatgcccc    8280
ggctgatgca ttgaaacaca acgcgcagat gatccaatca taccaaccag acgcatcagc    8340
gcgtgtagct gggggaaggg taggtggtgt agcccagaaa gcgacacggc tggctttcaa    8400
gaagtttatc aaccctagac agctttggag cggatacccg gctcttgtgg cgcatagctt    8460
gccagtgtcg gcgatacaga tgcctctgta cgagactttt cggtatcgaa tttctgaata    8520
tagattcgga gatcgagaga aggtgctaga aagatcaaga gattatggaa aagaaacagg    8580
cccattcgac aatcggagag gctgcagcga cagccgcgat aagtgctgca gcctcgggcg    8640
gtatagccag tgtcttgaca gcacccatgg atatagtccg gacacgaatc atgctcgatg    8700
ctgcagacac aaccgcacct cagaagaaaa ggatgatcaa taccgtacgg gagattatac    8760
gaacagatgg cccgagagga ctattccgag ggtgtgctat caacacgttt atggccgctg    8820
tcggatcagg gttatacttt ggtctctacg aaagcaccaa atggtggcta ggctcggact    8880
```

```
cgatggataa tagtgccatg ttagagtaag gggtgatggg aaatcttgta tataattgtg    8940
attgtttgta cgatagtggc cgactgtaca ttagtgatac cccactctta gaaaatagac    9000
caatctccag ctgcaccttc agacaatccg ggtaaaaatt ctcgtctatg ttggagattg    9060
gtgtgatttt gaaacatgac ccttgactct gatcttgaat atgtccatat ctcgaggcag    9120
gcatattatt catatagaga gggtatccct tagcatcggt ctgtcgtagt atccgactgc    9180
tgaatttatg aatcgcatca tacttgcgac atactgccat aaaaagagta cgtatccacc    9240
actacttatt gcgcaccaac acgcttcagg tatgcatccc atccctcttt ctggtaccgc    9300
ttcgccgcct ccacgggatc aggagcagca taaattccac gaccagcaat gataaagtcg    9360
gcaccgcgtc aacagcaga ttcaggagtc tggtattgct gtcccagctt gtctcccttc    9420
gaggagaggt tgacacctgt cgtgaacacg acgaaatcct cctcctccga aggagagcta    9480
acttcagact gaacctcgcc caggtgacgc gtcgagacga atcccatcac aaacttctta    9540
tacttccgag catagtcaac agaagaagta gtatattgac cggtagccaa agatcccttg    9600
gatgtcatct ccgcaaggat caaaaggccc ctctcagagc cgtagggaaa gtcctcggcc    9660
gaagcagtct gggctagagc ctcgacgata ccctcaccgg gcagaatact gcagttgatg    9720
atgtgggccc actcggagat gcgcagagtg ccgccatggt actgcttttg gactgtgttt    9780
ccgatatcga tgaacttgcg atcttcgaag atgaggaaat tgtgcttctc tgcaagggcc    9840
ttcagaccgg tgatggtctc ttcgctgaaa tcggagagga tatcgatgtg agttttgatc    9900
acggcaatgt acggaccgag tcctgttaaa taatccacca ttaaccatta ttagatcatt    9960
atgtaagtgg catccccggt gcgcatacgg tcagccaaat ccagcagctc tttggtggtt   10020
gtcacgtcgg ccgaaacggt gacattggtt ttcttggcct cggcaaccte aaagagcttc   10080
tttacgaggg cattggggtg cttgctagcg cgtgcactgt aggtcaattg cgacttggaa   10140
gacatgttgg cgatggaggg gtagcgcggg gttctgcaac tatcgtagaa atgagcactt   10200
agtggttgaa accggcttat tcagtagatt aatacttgaa gttttttagta atcagacaga   10260
ataatcagga tgtccaatta ctacctctta atatgtggaa tgaatgatag atataaattg   10320
tacgacaatt gccgcgaaaa attaaaatgg atctatggag gggacagtca tgcactagcc   10380
acacgttcct ccgcctgtgg ggtgagccac atgcctcatc tggaccaaac acatcgatgc   10440
agtcacatgc agataagatt agggcctatc cttagggtac ctgtccgcgc ggggattatg   10500
cctggctttt tgcctgcttt tgatatcctt tcaaggacat agcgataagt ccaaccttat   10560
cggccataat aatgtcaatg ccagcagcgg cttgggccta gaatattcca tcagctactg   10620
aacaacttct acatcacaat ttgaaagctc taagaattaa tatagaagca cttaccttcg   10680
cattttctgg tatattgttc tgagatccat aggatcagct tatcgatgat aagctgtcaa   10740
acatgagaat tcgggccgtc gaccaattct catgtttgac agcttatcat cgaatttctg   10800
ccattcatcc gcttattatc acttattcag gcgtagcaac caggcgttta agggcaccaa   10860
taactgcctt aaaaaaatta cgccccgccc tgccactcat cgcagtactg ttgtaattca   10920
ttaagcattc tgccgacatg gaagccatca caaacggcat gatgaacctg aatcgccagc   10980
ggcatcagca ccttgtcgcc ttgcgtataa tatttgccca tggtgaaaac gggggcgaag   11040
aagttgtcca tattggccac gtttaaatca aaactggtga aactcaccca gggattggct   11100
gagacgaaaa acatattctc aataaaccct ttagggaaat aggccaggtt ttcaccgtaa   11160
cacgccacat cttgcgaata tatgtgtaga aactgccgga aatcgtcgtg gtattcactc   11220
cagagcgatg aaaacgtttc agtttgctca tggaaaacgg tgtaacaagg gtgaacacta   11280
```

```
tcccatatca ccagctcacc gtctttcatt gccatacgta attccagatg taaattcatc    11340
atcaggcggg caagaatgtg aataaaggcc ggataaaact tgtgcttatt tttctttacg    11400
gtctttaaaa aggccgtaat atccagctga acggtctggt tataggtaca ttgagcaact    11460
gactgaaatg cctcaaaatg ttctttacga tgccattggg atatatcaac ggtggtatat    11520
ccagtgattt ttttctccat tttagcttcc ttagctcctg aaaatctcga taactcaaaa    11580
aatacgcccg gtagtgatct tatttcatta tggtgaaagt tggaacctct tacgtgccga    11640
tcaacgtctc attttcgcca aaagttggcc cagggcttcc cggtatcaac agggacacca    11700
ggatttattt attctgcgaa gtgatcttcc gtcacaggta tttattcgcg ataagctcat    11760
ggagcggcgt aaccgtcgca caggaaggac agagaaagcg cggatctggg aagtgacgga    11820
cagaacggtc aggacctgga ttggggaggc ggttgccgcc gctgctgctg acggtgtgac    11880
gttctctgtt ccgtcacac cacatacgtt ccgccattcc tatgcgatgc acatgctgta    11940
tgccggtata ccgctgaaag ttctgcaaag cctgatggga cataagtcca tcagttcaac    12000
ggaagtctac acgaaggttt ttgcgctgga tgtggctgcc cggcaccggg tgcagtttgc    12060
gatgccggag tctgatgcgg ttgcgatgct gaaacaatta tcctgagaat aaatgccttg    12120
gcctttatat ggaaatgtgg aactgagtgg atatgctgtt tttgtctgtt aaacagagaa    12180
gctggctgtt atccactgag aagcgaacga acagtcgggg aaaatctccc attatcgtag    12240
agatccgcat tattaatctc aggagcctgt gtagcgttta taggaagtag tgttctgtca    12300
tgatgcctgc aagcggtaac gaaaacgatt gaatatgcc ttcaggaaca atagaaatct    12360
tcgtgcggtg ttacgttgaa gtggagcgga ttatgtcagc aatggacaga acaacctaat    12420
gaacacagaa ccatgatgtg gtctgtcctt ttacagccag tagtgctcgc cgcagtcgag    12480
cgacagggcg aagcccctgg ttgccctcgc cgctgggctg gcggccgtct atggccctgc    12540
aaacgcgcca gaaacgccgt cgaagccgtg tgcgagacac cgcggccggc cgccggcgtt    12600
gtggatacct cgcggaaaac ttggccctca ctgacagatg aggggcggac gttgacactt    12660
gaggggccga ctcacccggc gcggcgttga cagatgaggg gcaggctcga tttcggccgg    12720
cgacgtggag ctggccagcc tcgcaaatcg gcgaaaacgc ctgattttac gcgagtttcc    12780
cacagatgat gtggacaagc ctggggataa gtgccctgcg gtattgacac ttgaggggcg    12840
cgactactga cagatgaggg gcgcgatcct tgacacttga ggggcagagt gctgacagat    12900
gaggggcgca cctattgaca tttgaggggc tgtccacagg cagaaaatcc agcatttgca    12960
agggtttccg cccgtttttc ggccaccgct aacctgtctt ttaacctgct tttaaaccaa    13020
tatttataaa ccttgttttt aaccagggct gcgccctgtg cgcgtgaccg cgcacgccga    13080
aggggggtgc ccccccttct cgaacccctcc cggtcgagtg agcgaggaag caccaggaa    13140 cagcacttat atattctgct tacacacgat gcctgaaaaa acttcccttg ggttatcca    13200 cttatccacg gggatatttt tataattatt ttttttatag tttttagatc ttctttttta    13260
gagcgccttg taggccttta tccatgctgg ttctagagaa ggtgttgtga caaattgccc    13320
tttcagtgtg acaaatcacc ctcaaatgac agtcctgtct gtgacaaatt gcccttaacc    13380
ctgtgacaaa ttgccctcag aagaagctgt ttttcacaa agttatccct gcttattgac    13440
tcttttttat ttagtgtgac aatctaaaaa cttgtcacac ttcacatgga tctgtcatgg    13500
cggaaacagc ggttatcaat cacaagaaac gtaaaaatag cccgcgaatc gtccagtcaa    13560
acgacctcac tgaggcggca tatagtctct cccgggatca aaaacgtatg ctgtatctgt    13620
```

```
tcgttgacca gatcagaaaa tctgatggca ccctacagga acatgacggt atctgcgaga    13680
tccatgttgc taaatatgct gaaatattcg gattgacctc tgcggaagcc agtaaggata    13740
tacggcaggc attgaagagt tcgcgggga aggaagtggt tttttatcgc cctgaagagg    13800
atgccggcga tgaaaaaggc tatgaatctt ttccttggtt tatcaaacgt gcgcacagtc    13860
catccagagg gctttacagt gtacatatca acccatatct cattcccttc tttatcgggt    13920
tacagaaccg gtttacgcag tttcggctta gtgaaacaaa agaaatcacc aatccgtatg    13980
ccatgcgttt atacgaatcc ctgtgtcagt atcgtaagcc ggatggctca ggcatcgtct    14040
ctctgaaaat cgactggatc atagagcgtt accagctgcc tcaaagttac cagcgtatgc    14100
ctgacttccg ccgccgcttc ctgcaggtct gtgttaatga gatcaacagc agaactccaa    14160
tgcgcctctc atacattgag aaaaagaaag gccgccagac gactcatatc gtattttcct    14220
tccgcgatat cacttccatg acgacaggat aggctagtga taataagtga ctgaggtatg    14280
tgctcttctt atctcctttt gtagtgttgc tcttatttta aacaactttg cggttttttg    14340
atgactttgc gattttgttg ttgctttgca gtaaattgca agatttaata aaaaaacgca    14400
aagcaatgat taaaggatgt tcagaatgaa actcatggaa acacttaacc agtgcataaa    14460
cgctggtcat gaaatgacga aggctatcgc cattgcacag tttaatgatg acagcccgga    14520
agcgaggaaa ataacccggc gctggagaat aggtgaagca gcggatttag ttggggtttc    14580
ttctcaggct atcagagatg ccgagaaagc agggcgacta ccgcacccgg atatggaaat    14640
tcgaggacgg gttgagcaac gtgttggtta caattgaa caaattaatc atatgcgtga    14700
tgtgtttggt acgcgattgc gacgtgctga agacgtattt ccaccggtga tcggggttgc    14760
tgcccataaa gaaaggtggc gtttacaaaa cctcagtttc tgttcatctt gctcaggatc    14820
tggctctgaa ggggctacgt gttttgctcg tggaaggtaa cgaccccag ggaacagcct    14880 caatgtatca cggatgggta ccagatcttc atattcatgc agaagacact ctcctgcctt    14940
tctatcttgg ggaaaggac gatgtcactt atgcaataaa gcccacttgc tggccggggc    15000
ttgacattat tccttcctgt ctggctctgc accgtattga aactgagtta atgggcaaat    15060
ttgatgaagg taaactgccc accgatccac acctgatgct ccgactggcc attgaaactg    15120
ttgctcatga ctatgatgtc atagttattg acagcgcgcc taacctgggt atcggcacga    15180
ttaatgtcgt atgtgctgct gatgtgctga ttgttcccac gcctgctgag ttgtttgact    15240
acacctccgc actgcagttt ttcgatatgc ttcgtgatct gctcaagaac gttgatctta    15300
aagggttcga gcctgatgta cgtatttttgc ttaccaaata cagcaatagt aatggctctc    15360
agtccccgtg gatggaggag caaattcggg atgcctgggg aagcatggtt ctaaaaaatg    15420
ttgtacgtga aacggatgaa gttggtaaag gtcagatccg gatgagaact gtttttgaac    15480
aggccattga tcaacgctct tcaactggtg cctggagaaa tgctcttct atttgggaac    15540 ctgtctgcaa tgaaattttc gatcgtctga ttaaaccacg ctgggagatt agataatgaa    15600
gcgtgcgcct gttattccaa aacatacgct caatactcaa ccggttgaag atacttcgtt    15660
atcgacacca gctgccccga tggtggattc gttaattgcg cgcgtaggag taatggctcg    15720
cggtaatgcc attactttgc ctgtatgtgg tcggatgtg aagtttactc ttgaagtgct    15780
ccggggtgat agtgttgaga agacctctcg ggtatggtca ggtaatgaac gtgaccagga    15840
gctgcttact gaggacgcac tggatgatct catcccttct tttctactga ctggtcaaca    15900
gacaccggcg ttcggtcgaa gagtatctgg tgtcatagaa attgccgatg ggagtcgccc    15960
tcgtaaagct gctgcactta ccgaaagtga ttatcgtgtt ctggttggcg agctggatga    16020
```

```
tgagcagatg gctgcattat ccagattggg taacgattat cgcccaacaa gtgcttatga    16080
acgtggtcag cgttatgcaa gccgattgca gaatgaattt gctggaaata tttctgcgct    16140
ggctgatgcg gaaatatttt cacgtaagat tattacccgc tgtatcaaca ccgccaaatt    16200
gcctaaatca gttgttgctc ttttttctca ccccggtgaa ctatctgccc ggtcaggtga    16260
tgcacttcaa aaagccttta cagataaaga ggaattactt aagcagcagg catctaacct    16320
tcatgagcag aaaaaagctg gggtgatatt tgaagctgaa gaagttatca ctcttttaac    16380
ttctgtgctt aaaacgtcat ctgcatcaag aactagttta agctcacgac atcagtttgc    16440
tcctggagcg acagtattgt ataagggcga taaaatggtg cttaacctgg acaggtctcg    16500
tgttccaact gagtgtatag agaaaattga ggccattctt aaggaacttg aaaagccagc    16560
accctgatgc gaccacgttt tagtctacgt ttatctgtct ttacttaatg tcctttgtta    16620
caggccagaa agcataactg gcctgaatat tctctctggg cccactgttc cacttgtatc    16680
gtcggtctga taatcagact gggaccacgg tcccactcgt atcgtcggtc tgattattag    16740
tctgggacca cggtcccact cgtatcgtcg gtctgattat tagtctggga ccacggtccc    16800
actcgtatcg tcggtctgat aatcagactg gaccacggt cccactcgta tcgtcggtct    16860
gattattagt ctgggaccat ggtcccactc gtatcgtcgg tctgattatt agtctgggac    16920
cacggtccca ctcgtatcgt cggtctgatt attagtctgg aaccacggtc ccactcgtat    16980
cgtcggtctg attattagtc tgggaccacg gtcccactcg tatcgtcggt ctgattatta    17040
gtctgggacc acgatcccac tcgtgttgtc ggtctgatta tcggtctggg accacggtcc    17100
cacttgtatt gtcgatcaga ctatcagcgt gagactacga ttccatcaat gcctgtcaag    17160
ggcaagtatt gacatgtcgt cgtaacctgt agaacggagt aacctcggtg tgcggttgta    17220
tgcctgctgt ggattgctgc tgtgtcctgc ttatccacaa cattttgcgc acggttatgt    17280
ggacaaaata cctggttacc caggccgtgc cggcacgtta accgggctgc atccgatgca    17340
agtgtgtcgc tgtcgacgag ctcgcgagct cggacatgag gttgcccgt attcagtgtc    17400 gctgatttgt attgtctgaa gttgttttta cgttaagttg atgcagatca attaatacga    17460
tacctgcgtc ataattgatt atttgacgtg gtttgatggc ctccacgcac gttgtgatat    17520
gtagatgata atcattatca ctttacgggt cctttccggt gatccgacag gttacggggc    17580
ggcgacctcg cgggttttcg ctatttatga aaattttccg gttaaggcg tttccgttct    17640 tcttcgtcat aacttaatgt ttttatttaa aataccctct gaaaagaaag gaaacgacag    17700
gtgctgaaag cgagcttttt ggcctctgtc gtttcctttc tctgtttttg tccgtggaat    17760
gaacaatgga agtccgagct catcgctaat aacttcgtat agcatacatt atacgaagtt    17820
atattcgatg cggccaaggt gagccagtgt gattacattt gcggcctaac tgtggccagt    17880
ccagttacgc tggagtcact agtatttagg tgacactata gaagcggccg ctagggataa    17940
cagggtaatg acaacttgtc cacgtggaat tctaagctta ggatcccact gtggtgg       17997
```

<210> SEQ ID NO 15
<211> LENGTH: 485
<212> TYPE: DNA
<213> ORGANISM: Artificial Sequence
<220> FEATURE:
<223> OTHER INFORMATION: fungal inducible promoter

<400> SEQUENCE: 15

```
tttgaggcga ggtgatagga ttggaagagt tctaattaac tgagtagaga actgttgatt         60
```

```
gttggttgat gatgttggtg agactgagaa ccttgggggt ctttatatag atgttcagct    120
atgcggggat gcgatcctgg ggtaggagag cacgtacggg gccccgctcg tttgtggctc    180
tccgtgcgga catcccgtgc ggacagtacc agaaagtgct ccgtctctgc tctatacggc    240
tctatacgcg tacctcttga acggtgcgtg gagaggagtg gtgtgtcaat ttccgccccg    300
ccctcgtgcg gttccgcatg catccaatcc taggtcggaa ctatcccgag ctgcggatgc    360
cgatgcggac ggacaagtgg gaactatcac aatcagcttt tcagctgggg gttattggat    420
ggtagctcca cacaggcgga gaaatacgaa gggacttaca gtgttccggc cgtgtcaaag    480
tgtct                                                                485

<210> SEQ ID NO 16
<211> LENGTH: 1842
<212> TYPE: DNA
<213> ORGANISM: Artificial Sequence
<220> FEATURE:
<223> OTHER INFORMATION: fungal codon optomized integrase gene

<400> SEQUENCE: 16
tcaggctgcc acgtcttcag tgccgtcctg cgcatcatcc tcatcgtcgt ctgtagggggg    60 cttcgcccat gtaatggaag cgcgcttctc gatgggcgtt ccctggcccc ggcctgttgt    120
agatttggtt acgacaatct tgtccacaaa caagccaacg aagacccttt tgtcatctac    180
actcgctcta ccccaccatg atttcggccc agtagggtct gcatccgcat cttccgggaa    240
ccactggtcc agcggcagct tcggagcctc cgcggcctcc agctcggcca atctttcctc    300
ggcaccctgc tgacgcaggg tgagcgcagc ttgctgttta cggaagtgct tgcgccccac    360
tgggccgtcg tacgcgcccg cagctcgatc ctcatacagc tcttcaagag cattcagtgc    420
gtcggctctc tctgcaacga ggttggctcg ttcgcccgac ttctcagggg cctcggtgag    480
tttaccgaat cttctagcag cctcccacag cagggccagg gtctcctcgt cgccttccgc    540
atgccttatc ttgttgaaga tccgctcagc aacaaactta tccaatgcag ccatagaaac    600
attacaggtt ccctcgtgct gtccaggagc ggaggggtca acaaccttcc ggcggcggca    660
gcgataagag tccttgatac tttcctcccc tctcttcgat gtcataacag cgccgcattc    720
acagtacaat ttatccattg cgctgagaat cgcctgacca cgactgagac ccttcccccg    780
tcctcggcca tccagccacg cctgcagctc ataccactca gccggttcta taatggggcc    840
gcaatccagt tcaaccggtc gtagagtgat tggatcgcgt tgaattctgt accccctcgat    900 cttcgttgtc ggtgtgccat cgggcttctt cttataaatc acctcagcgg caaagccggc    960
gatcctagga tcccgcagaa tcctcatgac agtcgcggga tcccaggcag acgaagcagt    1020
tttcttccca atggtctcgc cgcgcgtcgg tacggcatct gcgtccatgc gcttgcagag    1080
gccggtaatg ctccccgggt ggatggcagc ctgtgagcca ggcttaaagg gcaagtgctt    1140
gtgagtcttg atctctcgcc accaccatcg tattacatca ggctcaaatt cgaaagggcc    1200
ggtcagtggt gtggtcgaat gtgccaattt gttaatcact acgttcacca tgcgaccatt    1260
ccttgtaatc tccttcgttt ccgaaaccag ttcgaagcca taggggcct tcccccccac    1320 ataacctccc aattcccttt gaaggttctt tgtatccagg atcttagcgg atttgaggga    1380
agattccttg tgtgatgcat ccagccgcat aattagatga atcaagtcca tcacgttgcc    1440
ctggcggaag accccttctt gcgtcgaaac gatagtgacg cccagggcga gcaactctga    1500
gacgatcgga atagcatcca taaccttcag cctgctgaag cgagaaacat catatacaat    1560
aatcatattg agtctcccg ccctgcattc attgagaatc cgctcaaact cagggcgttc    1620
```

```
ggcggtgcca aaggcgctgg tgcctggggc ctctgaaaaa tggcaacaa  atctaaatct   1680 cccgccatcc cgctccacct cgcgctgaag gtcagcggcc ttgtcttcat tggcagagcg   1740
ctgggtggct ggcgaagctg cagagctgtt ctcgcgttcc ctcgactgtc ggtcgtacgc   1800
tccggcatag gtatctacac ctgtgactac gccttgtgtc at                     1842
```

<210> SEQ ID NO 17
<211> LENGTH: 613
<212> TYPE: PRT
<213> ORGANISM: Artificial Sequence
<220> FEATURE:
<223> OTHER INFORMATION: fungal codon optomized integrase

<400> SEQUENCE: 17

```
Met Thr Gln Gly Val Val Thr Gly Val Asp Thr Tyr Ala Gly Ala Tyr
  1               5                  10                  15

Asp Arg Gln Ser Arg Glu Arg Glu Asn Ser Ser Ala Ala Ser Pro Ala
             20                  25                  30

Thr Gln Arg Ser Ala Asn Glu Asp Lys Ala Ala Asp Leu Gln Arg Glu
         35                  40                  45

Val Glu Arg Asp Gly Gly Arg Phe Arg Phe Val Gly His Phe Ser Glu
     50                  55                  60

Ala Pro Gly Thr Ser Ala Phe Gly Thr Ala Glu Arg Pro Glu Phe Glu
 65                  70                  75                  80

Arg Ile Leu Asn Glu Cys Arg Ala Gly Arg Leu Asn Met Ile Ile Val
                 85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
        115                 120                 125

Glu Gly Val Phe Arg Gln Gly Asn Val Met Asp Leu Ile His Leu Ile
    130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
        275                 280                 285

Leu Arg Asp Pro Arg Ile Ala Gly Phe Ala Ala Glu Val Ile Tyr Lys
    290                 295                 300

Lys Lys Pro Asp Gly Thr Pro Thr Thr Lys Ile Glu Gly Tyr Arg Ile
305                 310                 315                 320
```

-continued

```
Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
                340                 345                 350

Arg Gly Arg Gly Lys Gly Leu Ser Arg Gly Gln Ala Ile Leu Ser Ala
                355                 360                 365

Met Asp Lys Leu Tyr Cys Glu Cys Gly Ala Val Met Thr Ser Lys Arg
        370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
                420                 425                 430

Arg His Ala Glu Gly Asp Glu Glu Thr Leu Ala Leu Leu Trp Glu Ala
                435                 440                 445

Ala Arg Arg Phe Gly Lys Leu Thr Glu Ala Pro Glu Lys Ser Gly Glu
        450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
                500                 505                 510

Gly Ala Glu Glu Arg Leu Ala Glu Leu Glu Ala Ala Glu Ala Pro Lys
                515                 520                 525

Leu Pro Leu Asp Gln Trp Phe Pro Glu Asp Ala Asp Ala Asp Pro Thr
        530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Val Thr Lys Ser Thr Thr
                565                 570                 575

Gly Arg Gly Gln Gly Thr Pro Ile Glu Lys Arg Ala Ser Ile Thr Trp
                580                 585                 590

Ala Lys Pro Pro Thr Asp Asp Asp Glu Asp Asp Ala Gln Asp Gly Thr
        595                 600                 605

Glu Asp Val Ala Ala
610
```

FUNGAL ARTIFICIAL CHROMOSOMES, COMPOSITIONS, METHODS AND USES THEREFOR

CROSS REFERENCE TO RELATED APPLICATIONS

This application claims benefit of and priority to U.S. Provisional patent application 62/286,542 filed Jan. 25, 2016. This application is hereby incorporated by reference in its entirety.

GOVERNMENT SUPPORT

This invention was made with government support under R43/44AI094885 awarded by the National Institutes of Health. The government has certain rights in the invention.

REFERENCE TO A SEQUENCE LISTING

The Sequence Listing, which is a part of the present disclosure, includes text file 0749sequence_ST25.txt, an 86 kilobyte file created on Apr. 29, 2016. This file comprises primer nucleotide and/or amino acid sequences of the present invention. The subject matter of the Sequence Listing is incorporated herein by reference in its entirety.

INTRODUCTION

Fungi contain an extensive but unexplored biosynthetic capacity, and can serve as reservoirs for novel bioactive compounds (Kobayashi, A., et al., Agric. Biol. Chem., 1988, 52, 3119-3123.; Kuno, F., et al., J. Antibiot. (Tokyo), 1996, 49, 742-747; Kumar, C. G., et al, Lett. Appl. Microbiol., 2011, 53, 350-358; Wu, M. C., et al., Curr. Opin. Biotechnol., 2012, 23, 931-940; Du, L., et al., Angew. Chem. Int. Ed. Engl., 2014, 53, 804-809; Fang, S. M., et al., Mar. Drugs, 2014, 12, 1788-1814; Leitlo, A. L. and Enguita, F. J., Microbiol. Res., 2014, 169, 652-665).

Filamentous fungi produce secondary metabolites (SMs) which have historically been a rich source of lead compounds for the pharmaceutical industry. Fungi produce 45% of bioactive molecules from all microbial sources (Bérdy, J., J. Antibiot (Tokyo), 2012, 65, 385-395). These compounds, derived from terpene, polyketide, and non-ribosomal peptide pathways (Keller, N. P., et al., Nat Rev Microbiol. 2005, 3: 937-947) display a broad range of useful antibiotic and pharmaceutical activities. A recent literature survey of fungal metabolites covering 1500 compounds that were isolated and characterized between 1993 and 2001, showed that more than half of the molecules had antibacterial, antifungal or antitumor activity (Pelaez, F., Handbook of Industrial Mycology (ed. An, Z.) 49-92 (Marcel Dekker, New York. 2005). Examples of fungal natural products having therapeutic or economic significance include the antibiotic penicillin from *Penicillium chrysogenum*, the immunosuppressant cyclosporine (a cyclic peptide) from *Tolypocladium inflatum*, and the cholesterol-lowering mevinolin (a.k.a. lovastatin, a polyketide) from *Aspergillus terreus*.

Fungal genomes can harbor 50 or more different SM gene clusters ranging from 20 to greater than 100 kb in size (Nordberg, H. et al., Nucleic Acids Res., 2014, 42 (Database issue), D26-31). Conservative estimates suggest that there are more than 5 million fungal species (Blackwell, M., Am. J. Bot., 2011, 98, 426-438), of which fewer than 5% have been described and less than 1% are available in the world's culture collections (Colwell, R. R., Microbial biodiversity and biotechnology. Washington, D.C.: Joseph Henry Press; p. 279-88, 1997). In addition, because each of these fungal genomes may harbor 50 or more different SM gene clusters ranging from 20 kb to greater than 100 kb in size (Nordberg, H. et al., Nucleic Acids Res., 2014, 42 (Database issue), D26-31), the number undiscovered SMs is presumably extremely large.

Several approaches to induce expression of SM clusters have been successful. These include overexpressing cluster-specific transcription factors or enzymatic genes, deleting or overexpressing chromatin-modifying genes, overexpressing trans-acting activators and deleting trans-acting inhibitors (Palmer, J. M. and Keller, N. P., Curr. Opin. Microbiol. 2010, 13: 431-436; Brakhage, A. A. and Schroeckh, V., Fungal Genet. Biol., 2011, 48, 15-22; Strauss, J. and Reyes-Dominguez, Y., Fungal Genet. Biol., 2011, 48, 62-69; Hong, S. Y., et al., Toxins (Basel) 2013, 5, 683-702). expression of heterologous SM genes (Itoh, T. et al., Methods Mol Biol 2012, 944, 175-182; Chiang, Y. M., et al., J. Am. Chem. Soc., 2013, 135, 7720-7731; Nielsen, M. T., et al., PLoS ONE 2013, 8: e72871; Tsunematsu, Y., et al., Nat Prod Rep 2013, 30: 1139-1149; Yin, W. B., et al. ACS Synth Biol 2013, 2: 629-634).

Expression of heterologous clusters in fungi is one approach to identify SM compounds, biosynthetic SM proteins and genes. Recently, this approach has been reported for synthesis of the *A. terreus*-encoded compounds geodin and asperfuranone in *A. nidulans* (Chiang, Y. M., et al., J. Am. Chem. Soc., 2013, 135, 7720-7731; Nielsen, M. T., et al., PLoS ONE, 2013, 8, e72871). *A. nidulans* was also used to heterologously express a dermatophyte-derived gene cluster responsible for the synthesis of neosartoricin B (Yin, W. B., et al., ACS Synth. Biol., 2013, 2, 629-634). These studies utilized a shuttle vector that included a ColE1 origin of replication, a yeast centromere sequence and an autonomously replicating sequence. This vector was used to create a single full length cluster in *A. nidulans*. These technologies require considerable time and effort to express just one heterologous cluster. These technologies are also only compatible with inserts smaller than about 20 kilobases (kb).

Large insert DNA cloning vectors are well established in a variety of systems, including: yeast artificial chromosome (YAC, Burke, D., et al., Science, 1987, 236, 806-812), bacterial artificial chromosome (BAC, Shizuya, H., et al., Proc. Natl. Acad. Sci. USA., 1992, 89, 8794-8797), P1-derived artificial chromosome (PAC, Ioannou, P. A., et al., Nat. Genet., 1994, 6, 84-89), *E. coli*-plant shuttle BAC, also called binary BAC (BIBAC, Hamilton, C. M., Gene, 1997, 200, 107-116), *E. coli-Streptomyces* artificial chromosome (ESAC, Sosio, M., et al., Nat. Biotechnol., 2000, 18, 343-345). However these plasmid systems are not compatible with fungi. A previously reported *E. coli*-fungus shuttle plasmid vector can neither accommodate nor maintain 100 kb or larger DNA fragments (Yin, W. B., et al., ACS Synth. Biol., 2013, 2, 629-634).

*A. nidulans* AMA1 is a fungal replication element that has been used in an *E. coli*-fungus shuttle vector for small plasmids (Gems, D., et al., Gene, 1991, 98, 61-67; Aleksenko, A. and Clutterbuck, A., J. Fungal Genet. Biol., 1997, 21, 373-387; Kubodera, T. et al. Biosci. Biotechnol. Biochem., 2000, 64, 1416-1426). There were also fungal shuttle plasmids or vectors reported for integration (Tiburn, J., et al., Gene. 1983, 26:205-221; Golduran, G. H. and Morris, N. R., Methods in Molecular Genetics 1995, 6, 48-65 Microbial Gene Techniques Edited by Kenneth W. Adolph; Kubodera, T., et al., Biosci. Biotechnol. Biochem., 2000, 64, 1416-1426; Arentshorst, M., et al., Fungal Biology and Biotechnology, 2015, 2, 2), autonomous replication or extra-chromosomal maintenance (Gems, D., et al., Gene, 1991, 98, 61-67; Golduran, G. H. and Morris, N. R., Methods in Molecular Genetics 1995, 6, 48-65 Microbial Gene Techniques Edited by Kenneth W. Adolph; Kubodera, T. et al. Biosci. Biotechnol. Biochem., 2000, 64, 1416-1426). However, these shuttle plasmids or vectors cannot be used to clone and transform very large DNA (such as 20 kb or larger). A previous attempt to introduce up to 75 Kb of fungal DNA into *Fusarium oxysporum* and *A. awamori* using an *Agrobacterium tumefaciens* transformation system yielded few transformants with large DNA inserts. Furthermore, no attempts to examine stability of heterologous DNA, let alone expression, were made (Takken, F. L., et al., Curr. Genet., 2004, 45, 242-248).

Bacterial artificial chromosomes (BACs) have been widely used for genomic DNA sequencing, positional cloning, and mapping in prokaryotes and eukaryotes including filamentous fungi (Zhu, H., et al., Fungal Genet. Biol., 1997, 21, 337-347; Nishimura, M., et al., Biosci. Biotechnol. Biochem., 1998, 62, 1515-1521; Adler, H. et al., Rev. Med. Virol., 2003, 13, 111-121; Diener, S. E., et al., Fungal Genet. Biol., 2004, 41, 1077-1087; Srivastava, S. K., et al., PLoS One 2014, 9: e81832). Although large-insert DNA systems have also been applied for heterologous expression of microbial natural product biosynthetic pathways and metagenomic studies, there has been limited success reported. (Béjà, O., Curr. Opin. Biotechnol., 2004, 15, 187-190; Lorenz, P. and Eck, J., Nat. Rev. Microbiol., 2005, 3, 510-516; Ongley, S. E., et al., Nat. Prod. Rep., 2013, 30, 1121-1138). Challenges with these systems include: 1) DNA cloning bias; 2) small DNA insert size; 3) lack of advanced heterologous expression hosts and 4) insufficient high-resolution chemical and data analysis pipelines. One reason for these challenges is that to date almost all BAC libraries are produced using partial restriction digestion (Wu, C. C., et al., Encyclopedia of Molecular Cell Biology and Molecular Medicine Volume 3 (2nd Edition), Edited by Meyers R. A., Wiley-VCH Verlag GmbH: Weinheim, Germany 2004, pp 385-425 2004; Zhang, M., et al., Nat. Protoc., 2012, 7, 467-478). Partial restriction digestion can be biased because the occurrence of restriction sites is highly variable and non-random in any genome including fungal genomes. Certain genomic regions can contain an excess of the restriction sites or lack them altogether, for example in regions of genomic DNA that contain highly repetitive sequences, such as centromeres and telomeres (Godiska, R., et al., Bias-Free Cloning of 'Unclonable' DNA for Simplified Genomic Finishing. In DNA Sequencing III: Dealing with Difficult Templates. Sudbury, M A: Jones and Bartlett Publishers: 2008). As a result, some sequences can be difficult or impossible to determine, even with multiple biased partial digestion libraries and up to 50× coverage.

Additionally, DNA fragments from rare or frequent cutting genomic regions can be either too large or too small for DNA fragment fractionation and can be excluded from cloning. Fragmentation of high molecular weight (HMW) genomic DNA by mechanical shearing, such as sonication, nebulization and hydroshearing, can generate small DNA fragments (10 kb or smaller). These methods can be unsuitable for preparing fragments ranging from 100 kb-300 kb. Freeze-thaw cycles have been reported to result in large DNA fragmentation, but these methods are not efficient enough for routine use (Osoegawa, K., et al., Genomics., 2007, 89, 291-299).

Red/ET (Red alpha/beta or RecE/T) tools have been developed for efficient large DNA or BAC-based recombinant engineering (Copeland, N. G., et al., Nat. Rev. Genet. 2001, 2: 769-779; Muyrers, J. P. P. et al., Trends in Bioch. Sci., 2001, 26, 325-331). Engineered large DNA or BACs have been routinely used for generating transgenic animals, such as mice, and for the functional study of large genes or pathways in mammals, such as humans (Johnson, S. J. and Wade-Martins, R. A., Biochem. Soc. Trans. 2011, 39, 862-867).

BAC-based large gene expression in animal models (Johnson, S. J. and Wade-Martins, R. A., Biochem. Soc. Trans. 2011, 39, 862-867) cannot be directly applied to study fungal SM pathways or discovery of natural products (NPs).

There is thus an unmet need for new methods and compositions for cloning large stretches of fungal DNA, such as entire clusters of genes involved in biosynthesis of secondary metabolites.

SUMMARY

Because of an unmet need for new tools to study fungal genes, the present inventor has developed vectors and methods for generating libraries of SM gene clusters that can be propagated and expressed in a fungal host.

In some embodiments, the present teachings include a fungal artificial chromosome (FAC). In various aspects, a fungal artificial chromosome can comprise at least one bacterial origin of replication, a bacterial selectable marker gene, a fungal selectable marker gene and a fungal autonomous replicating element. In various aspects, a FAC can be a shuttle vector or plasmid that can replicate in a bacterial host such as, for example, and without limitation *E. coli* as well as a fungal host, such as, for example and without limitation a filamentous fungus such as an *Aspergillus*. In some configurations, the *Aspergillus* can be *Aspergillus nidulans*.

In some configurations, a fungal artificial chromosome of the present teachings can be a dual-function fungal artificial chromosome (FACdual). In various configurations, a FACdual can comprise at least one bacterial origin of replication, a bacterial selectable marker gene, a fungal autonomous replicating element, an integration site for recombination with a host, an integrase gene, and a fungal selectable marker gene. In some configurations, the integration site can be, without limitation, an attP site. In some configurations, the integrase gene can be, without limitation, a fungal codon-optimized phi31 integrase gene. In some configurations, a FACdual can further comprise a fungal-operative promoter such as a fungal inducible promoter. In various configurations, the fungal-operative promoter can be operably linked to the integrase gene. In various aspects, a fungal inducible promoter can be an alcA(p) (Romero, B., et al., Fungal Genet. Biol. 2003 40, 103-114). In various aspects, a fungal inducible promoter can be a glaA(p) (Smith, T. L., et al., Gene, 1990, 88, 259-262). In various aspects, a fungal inducible promoter can be a sucA promoter (Roth, A. H., et al., Appl Microbiol Biotechnol., 2010, 86, 659-670).

In various configurations, a fungal autonomous replicating element can be any fungal autonomous replicating element, such as, without limitation, an AMA1 autonomous replicating element.

In some embodiments, the present teachings include a fungal artificial chromosome integration vector (FACint). In various configurations, a fungal artificial chromosome integration vector can comprise at least one bacterial origin of replication, a bacterial selectable marker gene, two fungal DNA sequences in the same orientation, and a fungal selectable marker gene. In various configurations, the two fungal sequences can be sequences homologous to a host fungal DNA. In various configurations, two fungal homologous DNA sequences can be, for example and without limitation, *Aspergillus* 1,007-bp 5'trpC and 1,000-bp 3'trpC homologous sequences. In various aspects, a FACint can replicate in a prokaryotic host such as, without limitation, an *E. coli*. In various aspects, a FACint can integrate into the genome of a fungal host such as, without limitation, an *Aspergillus* fungus such as an *Aspergillus nidulans*. In various aspects, a FACint can serve as a shuttle vector or plasmid. In various aspects, the bacterial selectable marker gene can be any bacterial selectable marker gene known to skilled artisans, such as, but not limited to a kanamycin-resistance gene (kanR).

In various configurations, a vector of the present teachings, i.e., a FAC, a FACdual or a FACint of the present teachings, can further comprise a cloning site comprising a plurality of recognition sites for endonucleases that bind and cut DNA at specific sequences. Endonuclease recognition sequences include recognition sequences of restriction endonucleases from prokaryotes and homing endonucleases from eukaryotes (as used herein, "restriction enzymes"). In some configurations, a cloning site can comprise a plurality of recognition sites for restriction enzymes that generate incompatible (i.e., non-complementary or non-palindromic) single-stranded overhangs upon digestion of the FAC. In some aspects, a cloning site can include recognition sequences for one or more restriction enzymes such as, without limitation, Bsr I, I-CeuI, BstXI, I-SceI or a combination thereof. In some aspects, a recognition sequence can be a recognition sequence of a restriction enzyme such as, without limitation, BstXI, I-SceI or a combination thereof. In some aspects, a cloning site can include a pair of restriction enzyme recognition sites in a tandem orientation. In some aspects, a cloning site can include a pair of restriction enzyme recognition sites in an opposing, "head-to-head" orientation. In some aspects a cloning site can include, in order, recognition sites for I-SceI, BstXI, BstXI, and I-SceI. In some aspects, the I-SceI sites can be in a head-to-head orientation with each other. In some aspects, the BstXI sites can be in a head-to-head orientation with each other. In some configurations, a cloning site can further comprise one or more recognition sites for other restriction enzymes such as, for example, Bam HI, Hind III, Eco RI, or NotI.

In various configurations, a vector of the present teachings can be maintained and can replicate in a prokaryotic host such as, without limitation, an *E. coli*, or in a eukaryotic fungal host such as, without limitation, an *Aspergillus* such as *A. nidulans*.

In some configurations, a vector of the present teachings can include a low-copy number bacterial origin of replication, an inducible high-copy number bacterial origin of replication, or a combination thereof, i.e., both a low-copy number and an inducible high-copy number bacterial origins of replication. In various aspects, a low-copy number bacterial origin of replication can be, for example and without limitation, an oriS. In various aspects, an inducible high-copy number bacterial origin of replication can be, for example and without limitation, an oriV. In various configurations, the high copy number origin of replication can be controlled by a replication initiation protein gene encoded in the *E. coli* host genome or a plasmid. In various configurations, the replication initiation protein gene can be TrfA. In various configurations, an inducible promoter can be operably linked to the replication initiation protein gene. In various configurations, the inducible promoter can be any bacterial inducible promoter, such as, without limitation, an arabinose-inducible promoter, a lac promoter, an IPTG-inducible T3 promoter, an IPTG-inducible T5 promoter or a rhamnose-inducible (rhaBAD) promoter.

In some configurations, a vector of the present teachings can include one or more genes for selectable markers for bacteria such as *E. coli*, such as, without limitation, a chloramphenicol resistance gene (camR or CAT), kanR, ampR, genR, tetA, strepR, galK or a combination thereof. In various aspects, a selectable marker can be used for positive selection (e.g., selecting for the presence of ampicillin resistance or galK (galactokinase) activity) or negative selection (e.g., selecting for the absence of galK activity (Warming, S., et al., Nucleic Acids Res. 2005, Vol. 33, No. 4 e36)).

In some configurations, a vector of the present teachings can include a fungal selectable marker gene, such as, without limitation, pyrG, ptrA, trpC or a combination thereof. In some aspects, a fungal selection marker gene can be a pyrG gene.

In some configurations, a vector of the present teachings can include an insertion of DNA from an exogenous source. In various configurations, a DNA insert can be an insertion at the cloning site. In various configurations, a DNA insert can be from any source, such as a virus, a prokaryotic microorganism, a eukaryotic microorganism, a plant, an animal, a human, or a cDNA generated from an RNA. In some configurations, a source of DNA can be the genome of a eukaryotic microorganism, such as a yeast or a filamentous fungus. In some configurations, a source of DNA can be an *Aspergillus* fungus, including any *Aspergillus* species. In some configurations, a source of DNA can be an *Aspergillus* fungus other than *Aspergillus nidulans*. In some configurations, a source of a DNA insert can be an *Aspergillus* fungus such as, without limitation, *A. acidus*, *A. aculeatinus*, *A. aculeatus*, *A. aeneus*, *A. affinis*, *A. alabamensis*, *A. alliaceus*, *A. amazonicus*, *A. ambiguus*, *A. amoenus*, *A. amstelodami*, *A. amyloliquefaciens*, *A. amylovorus*, *A. anomalus*, *A. anthodesmis*, *A. apicalis*, *A. appendiculatus*, *A. arachidicola*, *A. arenarius*, *A. arvii*, *A. asperescens*, *A. assulatus*, *A. astellatus*, *A. aurantiobrunneus*, *A. aureofulgens*, *A. aureolatus*, *A. aureoterreus*, *A. aureus*, *A. auricomus*, *A. australensis*, *A. austroafricanus*, *A. avenaceus*, *A. awamori*, *A. bacticus*, *A. bahamensis*, *A. biplanus*, *A. bisporus*, *A. bombycis*, *A. brasiliensis*, *A. brevipes*, *A. brevistipitatus*, *A. bridgeri*, *A. brunneo-uniseriatus*, *A. brunneoviolaceu*, *A. caelatus*, *A. caesiellus*, *A. caespitosus*, *A. calidoustus*, *A. campestris*, *A. candidus*, *A. capensis*, *A. carbonarius*, *A. carneus*, *A. cavernicola*, *A. cavernicola*, *A. cervinus*, *A. chevalieri*, *A. chungii*, *A. cibarius*, *A. clavatoflavus*, *A. clavatonanicus*, *A. clavatus*, *A. conicus*, *A. conjunctus*, *A. conversis*, *A. coreanus*, *A. coremiiformis*, *A. costaricensis*, *A. costiformis*, *A. creber*, *A. cretensis*, *A. cristatus*, *A. crustosus*, *A. crystallinus*, *A. cvjetkovicii*, *A. deflectus*, *A. delacroixii*, *A. delicatus*, *A. densus*, *A. dentatulus*, *A. depauperatus*, *A. dessyi*, *A. digitatus*, *A. dimorphicus*, *A. diplocystis*, *A. discophorus*, *A. disjunctus*, *A. diversus*, *A. dorothicus*, *A. dubius*, *A. dubius*, *A. duricaulis*, *A. dybowskii*, *A. eburneocremeus*, *A. eburneus*, *A. echinosporus*, *A. echinulatus*, *A. ecuadorensis*, *A. efthsus*, *A. egyptiacus*, *A. elatior*, *A. elegans*, *A. ellipsoideus*. *A. ellipticus*, *A. elongatus*, *A. equitis*, *A. erythrocephalus*, *A. falconensis*, *A. fasciculatus*. *A. fennelliae*, *A. ferrugineus*, *A. ferrugineus*, *A. ficuum*, *A. fiemonthi*, *A. filifera*, *A. fimetarius*, *A. fimeti*, *A. fischeri*, *A. fischerianus*, *A. flaschentraegeri*, *A. flavescens*, *A. flavidus*, *A. flavipes*, *A. flavofurcatus*, *A. flavoviridescens*, *A. flavus*, *A. flocculosus*, A. floriformis, A. foeniculicola, A. foetidus, A. fonsecaeus, A. foutoynontii, A. foveolatus, A. fresenii, A. fruticans, A. fruticulosus, A. fujiokensis, A. fuliginosus, A. fulvus, A. fumaricus, A. fumigatiaffinis, A. fumigatoides, A. fumigatus, A. fumisynnematus, A. fungoides, A. funiculosus, A. fuscus, A. galeritus, A. giganteus, A. gigantosulphureus, A. gigas, A. glaber, A. glaucoaffinis, A. glauconiveus, A. glaucus, A. globosus, A. godfrini, A. gorakhpurensis, A. gracilis, A. granulatus, A. granulosus, A. gratioti, A. greconis, A. griseus, A. guttifer, A. gymnosardae, A. halophilicus, A. halophilus, A. helicothrix, A. hennebergii, A. herbariorum, A. heterocaryoticus, A. heteromorphus, A. heterothallicus, A. heyangensis, A. hiratsukae, A. hollandicus, A. homomorphus, A. hortae, A. humicola, A. humus, A. ibericus, A. igneus, A. iizukae, A. implicatus, A. incrassatus, A. indicus, A. indohii, A. ingratus, A. insecticola, A. insuetus, A. insulicola, A. intermedius, A. inuii, A. itaconicus, A. ivoriensis, A. janus, A. japonicus, A. jeanselmei, A. kambarensis, A. kanagawaensis, A. kassunensis, A. katsuobushi, A. keveii, A. koningii, A. laciniosus, A. lacticoffeatus, A. laneus, A. lanosus, A. laokiashanensis, A. lateralis, A. lentulus, A. lepidophyton, A. leporis, A. leucocarpus, A. lignieresii, A. longivesica, A. longobasidia, A. luchensi, A. luchuensis, A. lucknowensis, A. luteoniger, A. luteovirescens, A. lutescens, A. luteus, A. macfiei, A. macrosporus, A. malignus, A. malodoratus, A. malvaceus, A. mandshuricus, A. manginii, A. mannitosus, A. maritimus, A. mattletii, A. maximus, A. medius, A. melitensis, A. melleus, A. mellinus, A. mencieri, A. michelii, A. microcephalus, A. microcysticus, A. microsporus, A. microthecius, A. microviridicitrinus, A. minimus, A. minisclerotigenes, A. minor, A. minutus, A. miyajii, A. miyakoensis, A. mollis, A. montenegroi, A. montevidensis, A. mucoroides, A. mucoroideus, A. muelleri, A. multicolor, A. multiplicatus, A. muricatus, A. muscivora, A. mutabilis, A. mycetomi-villabruzzii, A. mycobanche, A. nakazawae, A. nantae, A. nanus, A. navahoensis, A. neobridgeri, A. ncocarnoyi, A. neoellipticus, A. neoglaber, A. nidulellus, A. niger, A. nigrescens, A. nigricans, A. nishimurae, A. niveoglaucus, A. niveus, A. noclting, A. nominus, A. nomius, A. novofumigatus, A. novus, A. ochraceopetaliformis, A. ochraceoroseus, A. ochraceoruber, A. ochraceus, A. okazakii, A. olivaceofuscus, A. olivaceus, A. olivascens, A. olivicola, A. omanensis, A. onikii, A. oosporus, A. ornatulus, A. ornatus, A. oryzae, A. ostianus. A. otanii, A. ovalispermus, A. paleaceus, A. pallidus, A. panamensis, A. paradoxus, A. parasiticus, A. parrulus, A. parvathecius, A. parvisclerotigenus, A. parviverruculosus, A. parvulu, A. paulistensi, A. penicillatus, A. penicilliformis, A. penicillioides. A. penicillioideum, A. penicillopsis, A. periconioides, A. perniciosus, A. persii, A. petrakii, A. peyronelii, A. phaeocephalus, A. phialiseptatus, A. phoenicis, A. pidoplichknovii, A. piperis, A. polychromus, A. pouchetii, A. primulinus, A. profusus, A. proliferans, A. protuberus, A. pseudocaelatus, A. pseudocarbonarius, A. pseudocitricus, A. pseudoclavatus, A. pseudodeflectus, A. pseudoelatior, A. pseudoelegans, A. pseudoflavus, A. pseudoglaucus, A. pseudoheteromorphus, A. pseudoniger, A. pseudoniger, A. pseudonomius, A. pseudotamarii, A. pulchellus, A. pulmonum-hominis, A. pulverulentus, A. pulvinus, A. puniccus, A. purpureofuscus, A. purpureus, A. pusillus, A. pyramidus, A. pyri, A. qinqixianii, A. qizutongii, A. quadricinctus, A. quadricingens, A. quadrifidus, A. quadrilineatus, A. quercinus, A. quininae, A. quitensis, A. racemosus. A. raianus, A. rambellii, A. ramosus, A. raperi, A. recurvatus, A. rehmii, A. repandus, A. repens, A. reptans, A. restrictus, A. rhizopodus, A. robustus, A. roseoglobosus, A. roseoglobulosus, A. roseovelutinus, A. roseus, A. roseus. A. ruber, A. rubrobrunneus, A. rubnrum, A. rufescens, A. rugulosus, A. rugulovalvus, A. rutilans, A. sacchari, A. saitoi, A. salviicola, A. sartoryi, A. scheelei, A. schiemanniae, A. sclerogenus, A. sclerotiicarbonarius, A. sclerotioniger, A. sclerotiorum, A. sejunctus, A. septatus, A. sepultus, A. silvaticus, A. simplex, A. sojae, A. sparsus, A. spathulatus, A. spectabilis, A. spelunceus, A. spiculosus, A. spinosus, A. spinulosus, A. spiralis, A. stella-maris, A. stellatus, A. stellifer, A. stercoreus, A. sterigmatophorus, A. steynii, A. stramenius, A. striatulus, A. striatus, A. stromatoides, A. strychni, A. subfuscus, A. subgriscus, A. sublatus, A. sublcvisporus, A. subolivaceus, A. subsessilis, A. subunguis, A. sulphureus, A. sulphureus, A. sunderbanii, A. sydowii, A. sylvaticus, A. syncephalis, A. tabacinus, A. taichungensis, A. takakii, A. taklimakanensis, A. tamari, A. tapirirae, A. tardus, A. tatenoi, A. terrestris, A. terreus, A. terricola, A. testaceocolorans, A. tetrazonus, A. thermomutatus, A. thomi, A. tiraboschii, A. togoensis, A. tokelau, A. tonophilus, A. toxicarius, A. tritici, A. tsurutac, A. tuberculatus, A. tubingensis, A. tunctanus, A. udagawae, A. umbrinus, A. umbrosus, A. undulatus, A. unguis, A. unilateralis, A. usamii, A. ustilago, A. ustus, A. uvarum, A. vadensis, A. vancampcnhoutii, A. varanasensis, A. variabilis, A. varians, A. variecolor, A. variegatus, A. velutinus, A. venezuelensis, A. versicolor, A. vinosobubalinus, A. violaceobrunneus, A. violaceofuscus, A. violaceus, A. virens, A. viridigriseus, A. viridinutans, A. vitellinus, A. vitis, A. vitricola, A. wangduanlii, A. warcupii, A. wehmeri, A. welwitschiae, A. wentii, A. wcstendorpii, A. westerdijkiae, A. xerophilus, A. yezoensis, A. zhaoqingensis or A. zonatus.

In various configurations, a vector of the present teachings (i.e., a FAC, a FACdual or a FACint of the present teachings) can include an insert which can be at least 10 kb in length, at least 20 kb in length, at least 30 kb in length, at least 40 kb in length, at least 50 kb in length, at least 60 kb in length, at least 70 kb in length, at least 80 kb in length, at least 90 kb in length, at least 100 kb in length, at least 110 kb in length, or at least 120 kb in length. In various configurations, an insert can be up to 500 kb in length, up to 400 kb in length, up to 300 kb in length, up to 200 kb in length, or up to 150 kb in length. Thus, in various configurations, a vector of the present teachings can include an insert ranging, for example and without limitation, from 30 kb up to 500 kb, from 40 kb up to 400 kb, from 50 kb up to 300 kb, or from 100 kb to 500 kb.

In various configurations, a vector of the present teachings can include an insert which can comprise, consist essentially of, or consist of at least one secondary metabolite (SM) gene cluster. In various configurations, a vector of the present teachings can include an insert which can comprise, consist essentially of, or consist of at least one secondary metabolite (SM) gene cluster and all genes of this gene cluster encoding a final metabolite product from a fungus. In various aspect, the SM gene cluster can be from a fungal species heterologous to a host fungal species of a vector of the present teachings. In various aspects, the SM gene cluster can be from a fungal species other than A. nidulans, and the host fungal species can be A. nidulans. In various configurations, an insert comprising an SM gene cluster can be up to 500 kb in length, up to 400 kb in length, up to 300 kb in length, up to 200 kb in length, or up to 150 kb in length. Thus, in various configurations, a vector of the present teachings can include an SM gene cluster ranging, for example and without limitation, from 30 kb up to 500 kb, from 40 kb up to 400 kb, from 50 kb up to 300 kb, from 100 kb to 500 kb, from 100 kb to 400 kb, or from 100 kb to 300 kb. In various configurations, an SM gene cluster comprised by a vector of the present teachings can be a complete gene cluster. In some aspects, expression of an SM gene cluster in a heterologous fungal host can be used to recreate a biosynthetic pathway of a secondary metabolite.

In various configurations, the present teachings include a host fungus comprising a vector of the present teachings (i.e., a FAC, a FACdual, or a FACint). In various aspects, the host fungus can be a filamentous fungus, such as, without limitation, an *Aspergillus* fungus. In various aspects, the fungus can be an *Aspergillus nidulans* fungus. In various configurations, a host fungus comprising a vector of the present teachings comprising an SM gene cluster can express genes of the cluster. Because the genes of an SM gene cluster comprised by a vector of the present teachings are in a fungal environment, naturally occurring gene expression, post-transcriptional and post-translational regulation and modifications, as well as synthesis of secondary metabolites, can be duplicated or closely approximated. In some aspects, one or more genes of an SM gene cluster can be modified to effect an increase or a decrease in expression levels, or to alter protein structure.

In various configurations, a secondary metabolite (SM) gene cluster comprised by vector of the present teachings can be modified with one or more targeted insertions, one or more targeted deletions, or a combination thereof. In various aspects, a modification can lead to enhanced expression of one or more genes comprised by an SM gene cluster. In various aspects, a modification can lead to reduced expression of one or more genes comprised by an SM gene cluster. In various aspects, a modification can lead to activation of a cryptic gene. In various aspects, a modification can be a targeted insertion into a specific site in an SM gene cluster. In various aspects, a modification can be a targeted deletion of a portion of an SM gene cluster. In some aspects, the vector can be a FAC, a FACdual a FACint of the present teachings.

In some embodiments, the present teachings include methods of inserting a DNA sequence into a targeted location in a secondary metabolite (SM) gene cluster. In various configurations, these methods can comprise providing a vector of the present teachings (i.e., a FAC, a FACdual or a FACint of the present teachings) comprising a secondary metabolite (SM) gene cluster; providing an insertion DNA comprising, consisting essentially of, or consisting of a) a first sequence homologous to a sequence flanking a first side of the targeted location, b) a sequence to be inserted, c) a second sequence homologous to a sequence flanking a second side of the targeted location and d) a bacterial selectable marker; transforming the vector and the insertion DNA into an *E. coli* strain that expresses Red/ET recombinase enzymes; and selecting a transformed *E. coli* cell that comprises the bacterial selectable marker. Without being limited by theory, it is believed that insertion of a sequence at a targeted location can be achieved through homologous recombination between the insertion DNA and the SM gene cluster comprised by the vector. In some configurations, the bacterial selectable marker of the insertion DNA can be a marker other than a bacterial selectable marker comprised by the vector prior to the transformation. In various configurations, the bacterial selectable marker can be a positive selection marker or a negative selection marker. In some aspects, the vector can be a FAC.

In some embodiments, the present teachings include methods of deleting a targeted DNA sequence from a secondary metabolite (SM) gene cluster. In various configurations, these methods can comprise providing a vector of the present teachings (i.e., a FAC, a FACdual or a FACint of the present teachings) comprising a secondary metabolite (SM) gene cluster; providing a deletion DNA comprising a) a first sequence homologous to a sequence flanking a first side of the targeted DNA sequence, b) a second sequence homologous to a sequence flanking a second side of the targeted DNA sequence, and c) a bacterial selectable marker; transforming the vector and the insertion DNA into an *E. coli* strain that expresses Red/ET recombinase enzymes; and selecting a transformed *E. coli* cell that comprises the bacterial selectable marker. Without being limited by theory, it is believed that deletion of a targeted sequence can be achieved through homologous recombination between the deletion DNA and the SM gene cluster comprised by the vector. In some configurations, the bacterial selectable marker of the deletion DNA can be a marker other than a bacterial selectable marker comprised by the vector prior to the transformation. In various configurations, the bacterial selectable marker can be a positive selection marker or a negative selection marker. In some aspects, the vector can be a FAC of the present teachings.

In some embodiments, the present teachings include methods of constructing unbiased libraries in a vector of the present teachings. In various configurations, these methods can comprise providing high molecular weight (HMW) genomic DNA from a source of DNA such as a fungus; mechanically shearing the HMW genomic DNA into fragments of 100 kb-300 kb in length; generating blunt ends on the DNA fragments; ligating restriction enzyme linkers such as BstXI linkers to the blunt ends, thereby generating linker-ligated DNA fragments; purifying the linker-ligated DNA fragments by pulse field gel electrophoresis; and ligating the purified and linker-ligated DNA fragments into a restriction enzyme-cut vector such as a BstXI-cut vector of the present teachings. In various aspects, the methods can further comprise transforming a host microorganism with the ligated, restriction enzyme-cut vector. In various configurations, the host microorganism can be an *E. coli* or a second fungus such as, for example, an *A. nidulans*. In various configurations, the restriction enzyme can be BstXI. In various configurations, the vector can be a FAC of the present teachings. In various aspects, the source of the DNA can be a filamentous fungus such as, without limitation, an *Aspergillus* fungus, such as an *Aspergillus* other than *A. nidulans*. In some aspects, the host microorganism can be an *Aspergillus* fungus such as *A. nidulans*. In various aspects, the source of high molecular weight genomic DNA can be a fungal species other than the host fungal species. In various aspects, the HMW genomic DNA can be fungal genomic DNA heterologous to the host fungal species. In various aspects, the HMW genomic DNA can be fungal genomic DNA comprising a secondary metabolite gene cluster.

DETAILED DESCRIPTION

Figure 1C:
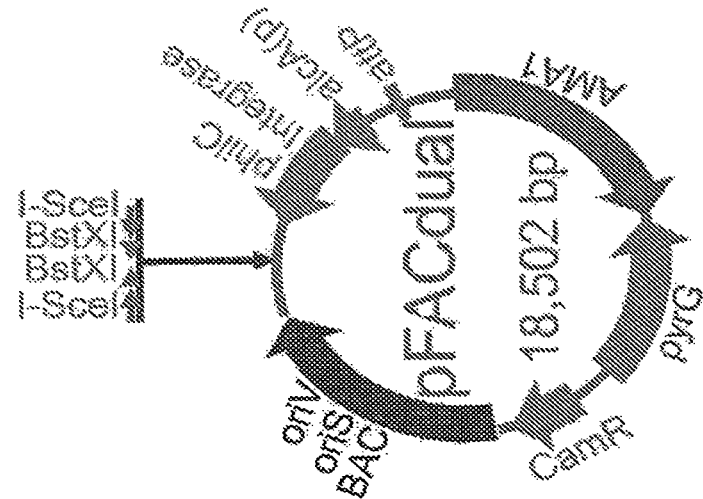
FIG. 1A-C illustrate diagrams of FAC vectors of the present teachings.

The present teachings provide vectors and methods for the production of unbiased large-insert genomic libraries, for capturing complete sets of large intact SM gene pathways from a fungus. The vectors can be used to shuttle large intact SM gene clusters between a fungal host and a bacterial host. *A. nidulans* can be used as a host for heterologous expression of SM gene clusters. In addition, vectors of the present teaching allow targeted modification of SM gene clusters with insertions and deletions using homologous recombination.

The present inventor has constructed unbiased fungal shuttle BAC (FAC) libraries with average insert sizes of 100 kb or larger from six sequenced fungi: *Aspergillius aculeatus, A. wentii, A. terretus, Fusarium solani, Penicillium expansum,* and *P. marneffei*. The average insert size in each library is such that an individual vector can contain a complete SM pathway, or a fungal secondary metabolite gene cluster which can range from 20 kb to over 80 kb. In some configurations, one vector can comprise all the genes of a SM biosynthetic pathway.

The new FAC libraries were created using randomly sheared DNA and without restriction partial digestion, another milestone in the field, removing bias and thus improving the quality of the library. With the FAC libraries, the present inventor has successfully captured 263 of 271 intact SM gene clusters or pathways predicted from the 6 sequenced fungi as individual FAC clones (Table 1).

The present inventor has demonstrated that large vectors such as vectors comprising intact SM gene clusters can be shuttled into a fungal host for stable plasmid maintenance. In addition, heterologous expression in an *A. nidulans* host of large SM gene clusters that are at least 150 kb has been achieved. In some configurations, A vector of the present teachings can contain a full-length SM gene cluster that can be regulated by the regulatory elements of a fungal host.

In some aspects, a vector comprising an intact SM gene cluster (such as a vector comprising an insert of about 100 kb) can be modified by a Red/ET technique, for fungal functional SM study. The present teachings include methods for the precise modification of fungal intact SM gene clusters at any selected DNA sequence position. The methods can be used, for example and without limitation, for activating cryptic, silent and or low-expression SM gene clusters, characterizing a gene or genetic element within a fungal SM gene cluster, and natural product (NP) discovery. Examples of modifications of 55 SM gene clusters or pathways are listed in Table 2.

In some configurations, an antibiotic resistance gene (for example, but without limitation a resistance gene for kanamycin, ampicillin or carbenicillin, erythromycin, tetracycline, gentamicin sulfate, penicillin, streptomycin, spectromycin, or chloramphenicol), can be used to select bacterial colonies harboring a vector comprising a modified SM gene cluster. Such vectors can be grown in *E. coli* on LB media with antibiotics appropriate for the both the vector and RED/ET selection markers. In some aspects, a selected colony can be grown within one day.

Figures 4A, 4B:
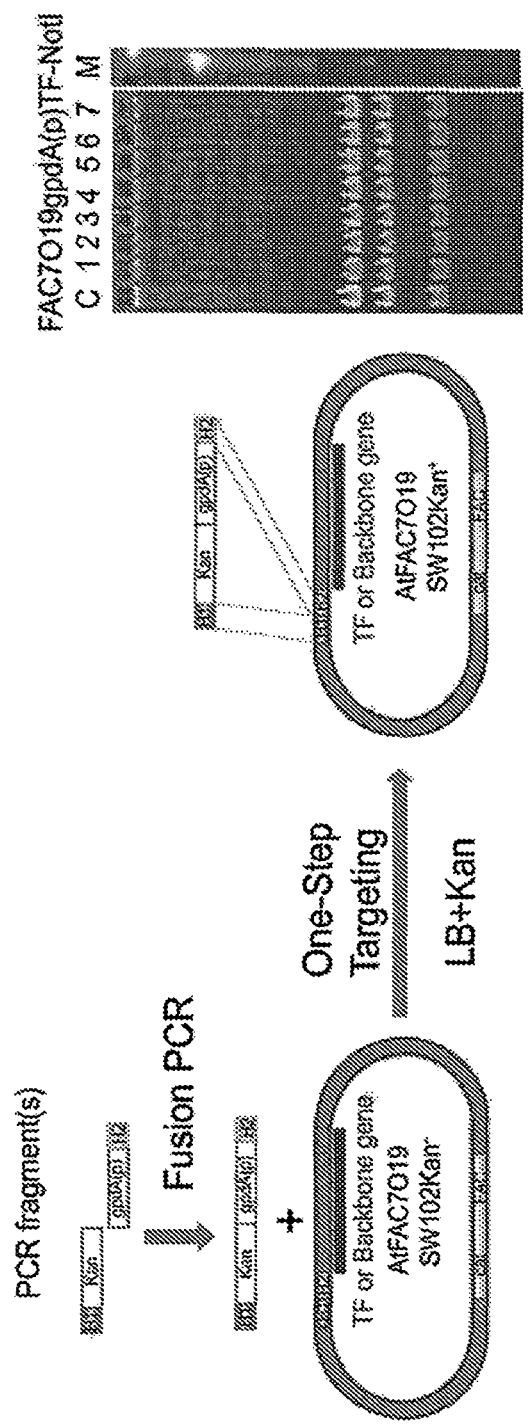
FIG. 4A-B Illustrate schematic overview of one-step precise FAC modification and molecular confirmation of successful fusion PCR.
Figure 5:
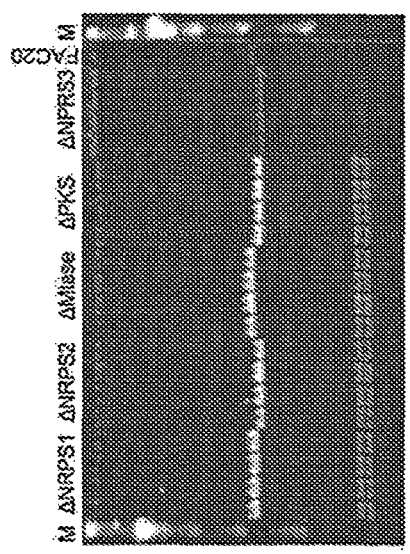
FIG. 5 A CHEFF gel shows five precise gene deletions of AtFAC9J20 (FAC20).

In some configurations, the present teachings include a fusion PCR approach which combines a selectable marker (e.g. KanR or galK gene) and a promoter (such as, but without limitation, gpdA(p), alcA(p), glaA(p), or pkiA (A)) as one PCR product for modifying a SM gene cluster (e.g. FIGS. 4A-B and 5).

In some configurations, the present teachings include methods for expressing a toxic SM compound, without the need to coexpress a resistance gene that can transport a toxic SM compound out of the cell. These methods use a vector comprising an inducible strong promoter such as alcA(p). In these methods, cells are initially grown without an inducing agent. When the cells reach a sufficient density, an inducing agent is added, and the cells express the genes of a secondary metabolite pathway. This approach can be used for the production of a toxic SM compound.

Figure 6:
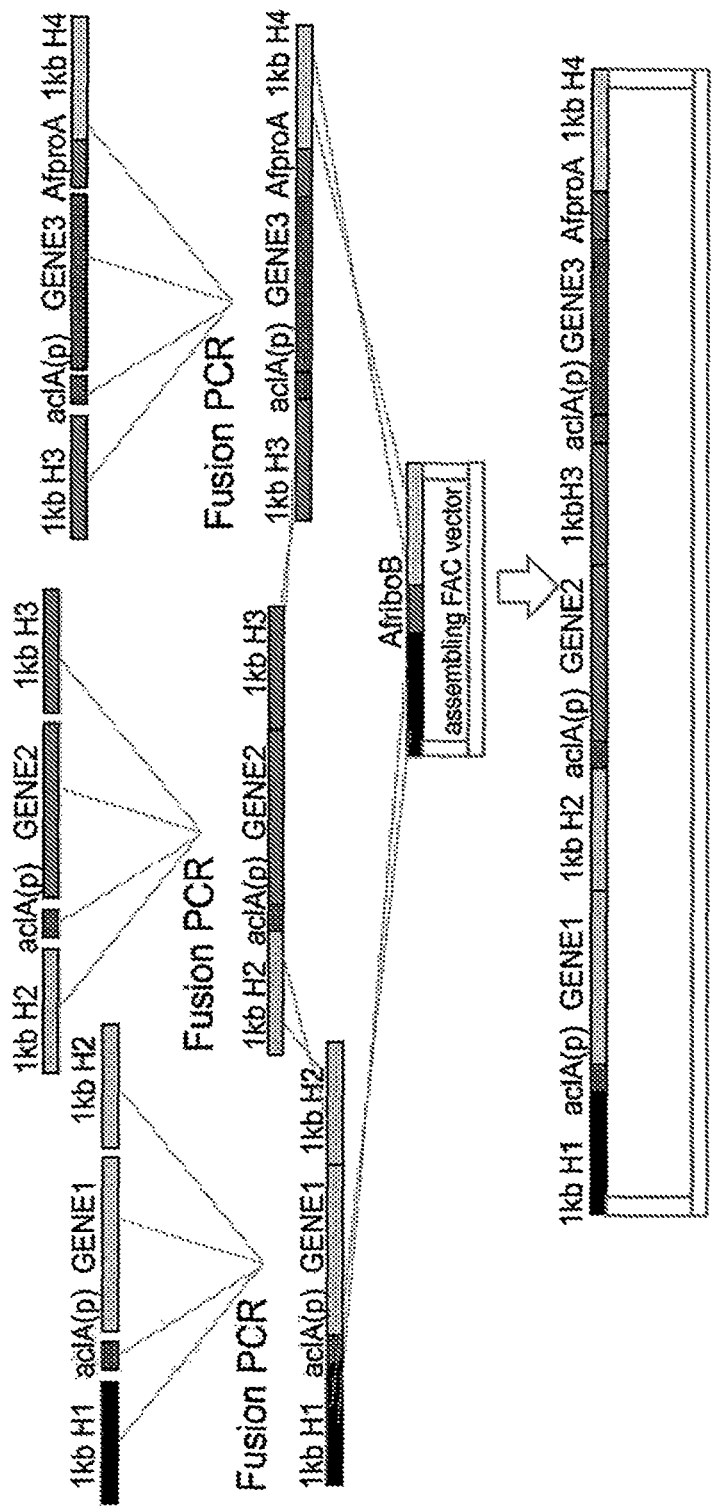
FIG. 6 A schematic diagram of assembling a synthetic SM gene cluster by the FAC system in *A. nidulans*.

In some configurations, vectors of the present teaching provide tools for assembling synthetic SM gene clusters in *A. nidulan* by fungal homologous recombination (FIG. 6). Individual genes (for example Gene1, Gene2, and Gene3, or more, total ~100 kb in size) can be either completely synthesized according to bioinformatics designs or cloned and fused with an inducible strong promoter (such as, but without limitation alcA(p)) and flanking homologous sequences (about 1 kb, H1, H2, H3, H4 and more). These genes and the cloning ready vectors (pFAC or pFACdual) containing the flanking homologous sequences of the synthetic SM gene cluster (e.g. H1, and H4) can be simultaneously transformed into *A. nidulans* to assemble the synthetic SM gene cluster by homologous recombination. Fungal selection markers such as AfpyroA and AfriboB (Szewczyk, E, et al., Nat. Protoc., 2006, 1, 3111-3120) can be used for the selection of a vector with a synthetic SM gene cluster. Unlike the previous genomic integration reported in the art (Szewczyk, E., et al., Nat. Protoc., 2006, 1, 3111-3120; Chiang, Y. M., et al., J. Am. Chem. Soc., 2013, 135, 7720-7731), a synthetic SM gene cluster-FAC of the present teachings can be isolated from *A. nidulans* and then shuttled back into *E. coli*. In some configurations, a FAC can be further modified, for example by adding regulatory elements or genes in *E. coli* or in vitro.

In some configurations, the present teachings include methods for assembly of novel synthetic SM gene clusters in *A. nidulan* by fungal homologous recombination (FIG. 6)

The present teachings disclose three types of vectors for the cloning of large inserts. These vectors can be used for replication and maintenance of large inserts as artificial chromosomes or for integration of large inserts into the host fungal genome. In various configurations, a plasmid that can be used as a fungal artificial chromosome can be a P1-based vector, a BAC-based vector, or a shuttle BAC vector that can be used to replicate large inserts in *E. coli* and fungal hosts.

In various configurations a vector of the present teachings can contain features for replication and maintenance of the plasmid in *E. coli*. A vector can comprise an origin of replication for *E. coli*, such as low-copy number origin, for example but without limitation an origin derived from an F plasmid. A low-copy number origin of replication can include, without limitation, an oriS. A vector can also comprise an origin of replication for *E. coli* that can be an inducible high-copy replication origin, such as, but without limitation, an oriV. A vector can also include an *E. coli* selection marker gene, such as a gene that confers resistance to an antibiotic such as, but without limitation: chloramphenicol, kanamycin, ampicillin or carbenicillin, erythromycin, tetracycline, gentamicin sulfate, penicillin, streptomycin, or spectromycin. In some configurations, a vector can also comprise at least one cloning site, which can be a multiple cloning site. In some aspects, a cloning site can comprise a pair of restriction sites wherein digestion with a restriction enzyme generates non-complementary single-stranded overhangs that can be ligated to specific linkers. Suitable enzymes include enzymes that can produce non-complementary single-stranded overhangs, such as non-palindromic overhangs such as overhangs resulting from digestion with an enzyme such as, without limitation, BstXI, BseYI, I-CeuI, I-SceI, PI-PspI, PI-SceI, AlwNI, BglI, BslI, BstAPI, DrdI, MwoI, PflMI, or SfiI. In some configurations, a second cloning site can comprise a pair restriction sites which flank the first cloning site enzyme cut sites wherein digestion with a second enzyme targeting these sites generates non-complementary single-stranded overhangs. Suitable enzymes include rare cutters that can create non-complementary single-stranded overhangs such as, but without limitation I-SceI, PI-PspI, and I-CeuI. Without being limited by theory, the combination of these two restriction enzyme site pairs can facilitate clean excision of the cloned large DNA fragment and exchange with other FAC plasmids, such as FAC integration plasmids. In various configurations, the high-copy number origin of replication can be regulated by a replication initiation protein that can be integrated into a host *E. coli* cell's genome on an inducible promoter, such as but without limitation an arabinose inducible promoter, a T5 promoter, a T7 promoter, a rhaBAD promoter or a β-galactosidase promoter. The replication initiation protein can be, for example and without limitation, TrfA.

In some configurations, a plasmid of the present teachings can be a BAC plasmid, which can comprise *E. coli* genes including oriS, repE, parA, and parB. (Shizuya, H., et al., *Proc. Nat'l. Acad. Sci. USA*. 1992, 89, 8794-8797). In various configurations, a plasmid of the present teachings can be a P1-derived vector which can comprise a plasmid replicon, a P1 lytic replicon, and a SacB selection gene. (Ioannou, P. A., et al., *Nat. Genet.*, 1994, 6, 84-89). In various configurations, a plasmid of the present teachings can be a binary bacterial artificial chromosome (BIBAC) and can comprise a minimal origin of replication from the *E. coli* F plasmid and a minimal origin of replication of the *Agrobacterium rhizogenes* R$_i$ plasmid (Hamilton, C. M., *Gene*, 1997, 200, 107-116). In various configurations, a plasmid of the present teachings can be an *E. coli*-*Streptomyces* artificial chromosome (ESAC) plasmid, which can comprise an attP-int-tsr cassette (Sosio, M. et al. *Nat. Biotechnol.*, 2000, 18, 343-345). Each of these plasmids can further comprise a fungal replication element such as an AMA1 autonomous replicating element.

In some configurations, a FAC vector can contain features for their replication in fungal cells. These include a fungal origin of replication, such as, but without limitation autonomous maintenance in *Aspergillus* (AMA1, SEQ ID NO: 8). A FAC vector can also contain a fungal selection marker gene, such as but without limitation, orotidine-5'-phosphate decarboxylase gene (pyrG, originated from *A. parasiticus*, SEQ ID NO: 9 and SEQ ID NO: 10), ptrA, or trpC.

In some configurations, the present teachings include a FAC dual-function vector that can be maintained in *E. coli* as a fungal artificial chromosome, can be induced to integrate into the fungal genome, and can be used as a *E. coli*-fungus shuttle BAC vector. A dual function vector has the same features as a regular FAC vector as described supra, and an additional gene cassette: an attP site and an integrase gene, such as but without limitation a phi31 integrase gene, under the control of fungal inducible promoter, such as but without limitation, alcA promoter or glaA(p). In various configurations, the integrase gene can be codon optimized for fungal expression.

In various configuration, a FAC system of the present teachings can be used in a wide variety of fungi, such as and without limitation *Aspergillus aculeatus, A. terreus, A. wentii, Fusarium solani, Penicillium expansum, P. marneffei, Neurospora crassa*, and fungi belonging to the phylum *Ascomycetes*.

Definitions

Various terms are used herein to refer to aspects of the present teachings. To aid in the clarification of description of the components of these teachings, the following definitions are included.

The term "fungus" as used herein refers to is any member of the group of eukaryotic organisms that includes unicellular microorganisms such as, without limitation, yeasts and molds, as well as multicellular fungi that produce familiar fruiting forms known as mushrooms. More particularly they are filamentous fungi or molds, such as, and without limitation. *Aspergillus aculeatus, A. terreus, A. wentii, Fusarium solani, Penicillium expansum*, and *P. marneffei*.

"Secondary metabolite (SM)" as used herein refers to a chemical compound that is not involved in primary metabolism, and therefore differs from the more prevalent macromolecules such as proteins and nucleic acids. Thousands of SMs have been described from various eukaryotic organisms including fungi (Donadio, S., et al., Nat. Prod. Rep., 2007, 24, 1073-1109).

"SM gene cluster or pathway" as used herein refers to a set of biosynthetic genes that comprise polynucleotide sequences encoding the proteins, such as but without limitation an enzyme, required for synthesis and activity of a secondary metabolite. SM gene clusters or pathways implement the conversion of a starting compound, such as but without limitation a substrate, into a final compound or NP.

The term "intact or full-length SM gene cluster or pathway" used herein refers to a SM gene cluster or pathway contains a complete set of biosynthetic genes and regulatory elements. Each fungal genome may harbor 50 or more different intact SM gene clusters ranging from 20 to more than 100 kb in size (Nordberg, H. et al., Nucleic Acids Res., 2014, 42 (Database issue), D26-31). Fungal SM clusters usually comprise one or more backbone gene(s) such as polyketide synthases (PKSs), nonribosomal peptide synthetases (NRPSs), dimethylallyl tryptophan synthases (DMATs), and terpene cyclases (TCs), surrounded by genes for modifying enzymes including, but not limited to, oxidoreductases, oxygenases, dehydrogenases, reductases, and transferases (Keller, N. P. and Hohn, T. M., Fungal Genet. Biol. 1997, 21, 17-29; Walton, J. D., Fungal Genet. Biol., 2000, 30, 167-171).

"Regulatory element" as used herein refers to a nucleic acid sequence element that controls or influences the expression of a gene, such as a gene within a large polynucleotide insert from a gene cassette, genetic construct or a FAC vector. A regulatory element can be, for example and without limitation, a promoter, an enhancer, a transcription factor or control sequence, a translation control sequence, a temporal or tissue-specific regulatory element, a polyadenylation signal sequence, a 5' or 3' UTR, a repressor or a terminator. Regulatory elements can be homologous or heterologous to the large polynucleotide insert or intact SM gene cluster to be expressed from a FAC construct or vector as described herein. When a FAC vector as described herein is present in a cell such as a heterologous *A. nidulans* cell, a regulatory element can be naturally occurring, endogenous, exogenous, and/or engineered with respect to the cell.

"Compatible" as used herein refers to two nucleic acid ends may mean that the ends are either both blunt or contain complementary single strand overhangs, such as that created by mechanically shearing DNA followed by DNA end repair, DNA linker ligation, or after digestion with a restriction endonuclease. At least one of the ends may contain a 5' phosphate group, which can allow ligation of the ends by a double-stranded DNA ligase.

"BstXI Linker" (Klickstein, L. B. and Neve, R. L., Current Protocols in Molecular Biology, John Wiley & Sons, Inc. 1991, 5.6.1-5.6.10) as used herein refers to two partially complementary strands of DNA that are annealed to one another to produce a double-strand DNA molecule with an overhang complementary to one end of the BstXI cutting sequences as above. An example of a BstXI linker for ligation of the blunt ends of large DNA fragments is the following:

```
BstXI Linker Top
                                    (SEQ ID NO: 5)
5'-CTGGAAAG-3'

BstXI Linker Bottom
                                    (SEQ ID NO: 6)
5'-CTTTCCAGCACA-3'
```

The blunt ends of the BstXI linker can be designed to be complementary to large DNA fragments. For example, the target large DNA fragments may be mechanically sheared DNA which is polished and made blunt by DNA end repairing enzyme mixture (Intact Genomics, St. Louis, Mo.). The blunt DNA can also be modified by non-template mediated addition of a single A nucleotide to each end of the target large DNA by Taq polymerase. In this case, the above linker can be modified with an additional single T nucleotide to the 3' of BstXI Linker Top strand.

"Shuttle bacterial artificial chromosome (BAC) vector" means a BAC vector that can be used for the transfer and the maintenance of genetic information from one (or more) donor bacterial species or strain(s) to one or more host organism(s) or strain(s) or species.

"FAC vector" as used herein refers to a fungal artificial chromosome vector, or a shuttle BAC vector between *E. coli* and *A. nidulans*.

"Library" as used herein refers to a plurality of clones each comprising an insert sequence and a vector.

Methods

Methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Nagy, A., Manipulating the Mouse Embryo: A Laboratory Manual (Third Edition), Cold Spring Harbor, N.Y., 2003 and Harlow, E., Using Antibodies: A Laboratory Manual, Cold Spring Harbor Laboratory Press, Cold Spring Harbor, N.Y., 1999. As used in the present description and any appended claims, the singular forms "a", "an" and "the" are intended to include the plural forms as well, unless the context indicates otherwise.

The following materials and methods are also used in various aspects of the present teachings.

The present teachings provide for the preparation of ultra-high quality of high molecular weight (HMW) genomic DNA from a fungus and the generation of an unbiased large insert FAC library by randomly shearing with average insert size 100 kb or larger. The large DNA population of a library includes not only fragments of all biosynthetic loci in the fungal genome with minimal bias, but also each DNA molecule is large enough (100 kb or larger) to cover at least one of the intact SM gene clusters.

High molecular weight (HMW) genomic DNA can be derived from any cultured, isolated, purified or mixed fungi, including fungi with published genome sequences. The HMW genomic DNA can be prepared directly from a population of uncultured fungi in their natural habitat, environment, or biomass without the need of fungal isolation and cultivation.

The techniques of HMW genomic DNA preparation for BAC cloning have been documented (Wu, C. C., et al, Encyclopedia of Molecular Cell Biology and Molecular Medicine Volume 3 (2nd Edition), Edited by Meyers R. A., Wiley-VCH Verlag GmbH: Weinheim, Germany 2004, pp 385-425; Zhang, M., et al., Nat. Protoc., 2012, 7: 467-478). In some configurations, HMW genomic DNA can include intact chromosomes or can be megabases in size.

For preparation of HMW genomic DNA, fungal cells, such as, but without limitation, spores, germinated spores, protoplasts, or nuclei can be collected and directly embedded in low-melting agarose plugs. The low-melt agarose plugs can be from about 0.4% to about 1% in concentration and can have a final concentration of about 0.5%. HMW genomic DNA can be purified by treatment with lauryl sarcosine and proteinase K in 0.5 M EDTA, pH 9.0. HMW genomic DNA can be prepared by preparing fungal protoplasts (Bok, J. W. and Keller, N. P., Methods Mol. Biol., 2012, 944, 163-174) and then embedding the fungal protoplasts in low melt agarose plugs.

HMW genomic DNA can be used to generate unbiased large insert recombinant DNA libraries to cover large intact SM gene clusters wherein one clone contains an intact SM gene cluster or pathway. The present teachings provide for preparation of liquid HMW genomic DNA by either electroelution or Gelase digestion of the agarose DNA plugs. The liquid HMW genomic DNA can then be mechanically sheared by hydroshearing, repeated pipetting, low-speed vortexing or a combination thereof. Conditions for a given fungal genome can be determined by running sheared HMW genomic DNA on a CHEFF gel with the size range of about 100 kb to about 300 kb.

Figure 1B:
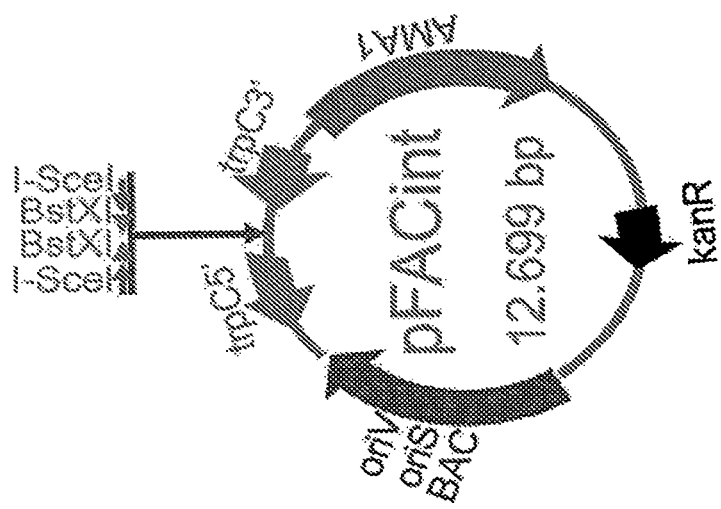
Figure 1A:
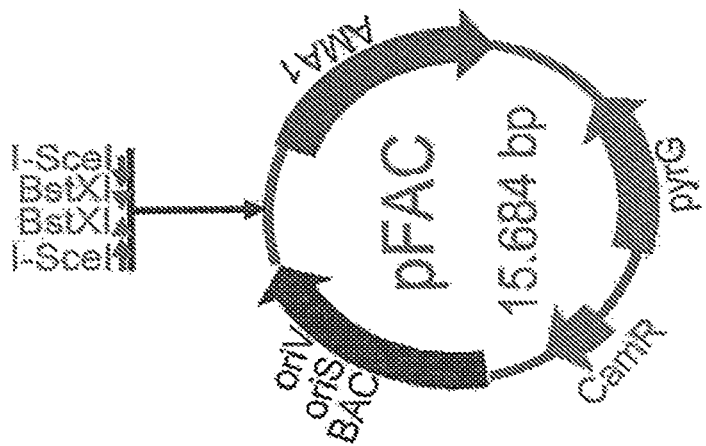
Figures 3A, 3B, 3C:
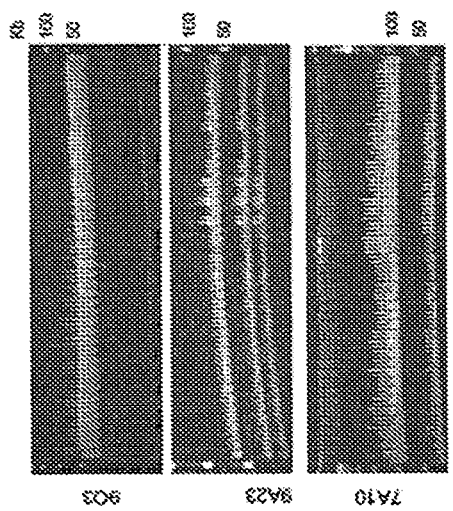
FIG. 3A-C CHEFF gels showing that *E. coli-Aspergillus* shuttle BACs or FACs are successfully transferred from transformed strains of *A. nidulans* back into *E. coli*.

The *E. coli*-fungal shuttle BAC vectors or FAC (FIG. 1) vectors disclosed herein (see Example 1) can be used for BAC/FAC library construction with average inserts 100 kb or larger. The present inventor has demonstrated that the large-insert FACs (at least 150 kb) can be shuttled into the heterologous *A. nidulan* host for stable maintenance and NP discovery (FIG. 3, Bok, J. W., et al., BMC Genomics, 2015, 16, 343).

Random Shear BAC Cloning Method for Construction of Unbiased FAC Libraries.

HMW genomic DNA was sheared as described in Methods. To 400 µl of sheared HMW genomic DNA (100~300 kb), 5 µl of DNA end repairing enzyme mixture (Intact Genomics, St. Louis Mo.), 100 µl of 5×DNA end repairing buffer to a total of 500 µl. The sample is mixed well by gently pipetting with a wide-bore tip and the reaction is incubated at room temperature for 30 min. The DNA end repairing enzymes are heat killed by incubating the large DNA end repair reaction at 70° C. for 15 min. 20 µl each of 100 µM BstXI linker TOP and Bottom ($10^6$~$10^7$-fold more molar rate excess linkers than the large DNA molecules), 61 µl of 10× T4 ligation buffer with ATP and 10 µl of large DNA T4 ligase (intactgenomics) are added immediately and then the reaction is mixed well by gently pipetting with a wide-bored tip. The linker ligation reaction is set at room temperature for 3-8 hours. The linker-ligated large DNA fragments are fractionated and excess BstXI linkers are removed by 1% agarose CHEFF gel electrophoresis at 0.5×TBE, 6V/cm, 90 s/90 s for 16 hours and 4V/cm, 5 s/5 s for additional 8 hours. Lambda DNA ladder marker (Intact Genomics) is used as a control to recover 100~150, 150~210, 210~300 kb large DNA fractions as gel slices, and then the gel slices are placed into dialysis tubes and the DNA is electreluted, and then the purified linker-ligated large DNA fragments are dialyzed against 100 ml of ice-cold and autoclaved ultra-pure water at least 3 times, for one hour each. The cloning-ready BstXI-FAC vectors (20 ng/µl, Intact Genomics) are mixed with the gel-purified BstXI-linker ligated DNA (2~3 ng/µl) at 1:3 molar rate, and the ligation reaction is set at 16° C. for overnight. For example, 200 µl large DNA (3 ng/µl) is mixed with 10 µl of the FAC vector (20 ng/µl), 60 µl of 5× T4 ligation buffer, 30 µl of BAC cloning T4 ligase (intactgenomics), ligation reaction is set at 16° C. for overnight, preferably 12~18 hours.

Large-Insert FAC Library Construction.

The large DNA fragments of the library are cloned into FAC vector(s) and serve as a screening library for covering the fungal SM gene clusters or pathways in E. coli. Preferably, the large-insert FAC library has average insert size 100 kb or larger, therefore it is sufficient to contain at least one intact SM gene cluster in an individual FAC clone. Furthermore, the large-insert FAC library is unbiased and a FAC library with only 10×, or even 5× genome coverage can be enough to capture an entire set of intact SM gene clusters from a sequenced fungal genome or a fungal sample. Using the methods described herein, the inventor can capture a complete set of intact SM gene clusters with 4~5 384-well plates of FAC clones (average about 100 kb, 4~5× genome coverage) from all 6 fungi studied (Table 1; Bok, J. W., et al., BMC Genomics, 2015, 16, 343).

Because the FAC system is a shuttle BAC system, vectors of the present teachings can be in the BAC/fosmid library screening techniques known in the art. To identify intact SM gene cluster-containing FAC clones, sequence-based approaches can be used for FAC library screening such as PCR or colony hybridization (Zhang, H. B. and Wu, C. C., Plant Physiol. Biochem., 2001, 39, 1-15; Kang, H. S. and Brady, S. F., Angew. Chem. Int. Ed. Engl., 2013, 52, 11063-11067). One application of sequence-based approaches involves the design of DNA probes or primers which are derived from conserved regions of already known genes or protein families, for example but without limitation, pooled FAC DNAs from each arrayed library are screened using degenerate primers designed to amplify the conserved domains/regions of PKS or NRPS (Kang, H. S. and Brady, S. F., Angew. Chem. Int. Ed. Engl., 2013, 52, 11063-11067). Positive FAC clones can be recovered from libraries by PCR screening of the respective pools, followed by screening of their plates, columns, and rows from which they are identified. Another sequence based approach is to use high throughput next generation sequencing of pooled FAC libraries by plate-column-row with multiplex barcodes. This strategy will reduce sequence complexity from whole fungal genomes into FAC pool-level (plate-column-row), therefore enabling the complete assembly of pooled FAC clones (each 100 kb or larger). The intact SM gene clusters will be identified by annotation of completely sequenced and assembled FAC clones. The individual SM gene cluster-containing FAC clones will then be de-convoluted by barcodes and plate-column-row coordinates. The advantage of these sequence-based approaches is to identify SM gene clusters and their FACs from fungi without the precondition of genome sequence or even metagenomes of unculturable fungal community. In the present teachings, another sequence-based approach is used to sequence the FAC clone ends by the traditional Sanger sequencing method, then identify the entire set of intact SM gene cluster-containing FACs by aligning the FAC end sequences onto the fungal reference genome sequences. Similarly a next-generation sequence method may be used for this purpose with FAC DNA pooling and barcoding to reduce the sequencing cost.

Microbial Strains and Culture Conditions

The parental strain RJW256 (pyrG89, pyroA4, Δnku70::argB, ΔST::afpyrG, veA1) was obtained by a sexual cross between LO4641 (riboB2, pyroA4, ΔST::AfpyrG, ΔAN7909::afpyrG, Δnku70::argB, veA1) and RJW113.5 (ΔveA::argB, pyrG89). RJW256 was transformed with FAC plasmids to produce FAC recombinant strains. ΔST::AfpyrG indicates that the entire endogenous sterigmatocystin gene cluster was removed from A. nidulans.

For antimicrobial activity tests, we used A. nidulans RDIT9.32, A. fumigatus 293, Candida albicans, Pseudomonas aeroginosa PAO1, Bacillus cerceus U85, and Micrococcus luteus strains. All of the fungal and bacterial strains were maintained as frozen glycerol stocks at −80° C. Fungal strains were grown at 37° C. on glucose minimal medium (GMM, Bok, J. W. and Keller, N. P., Eukaryot. Cell, 2004, 3, 527-535) and bacterial strains were cultured on tryptic soy broth medium.

A. nidulans Transformation and the Recovery of SM Cluster-Containing FACs

A modified PEG-calcium based transformation method was applied to improve transformation. The described method (Bok, J. W. and Keller, N. P., Eukaryot. Cell, 2004, 3, 527-535) was modified as follows: 200 µL containing 107 A. nidulans RJW256 protoplasts mixed with 2 µg FAC DNA were gently placed over 200 µL of 30% PEG 4,000 with 50 mM $CaCl_2$ in a 1.5 mL centrifuge tube. The centrifuge tube with protoplasts was incubated 30 min on ice. After centrifuging the incubated mixture for 5 min at 250×g, the solution was gently mixed using an autopipette. This mixture was then incubated for 10 minutes at room temperature before 1 mL of sorbitol-Tris-HCl—$CaCl_2$ (STC: 1.2M sorbitol, 10 mM Tris-HCl, 10 mM $CaCl_2$ pH7.5) buffer was added and gently mixed into the solution. After transferring the mixture into a 13 mL tube, an additional 5 mL of STC was added into the tube and gently mixed. One mL of this final solution was distributed onto regeneration media to obtain transformants.

A. nidulans FAC transformants were maintained on culture plates for three generations for phenotype and chemical screening. For FAC recovery, we prepared ~0.3 mL of 106/mL protoplasts from A. nidulans FAC strains and FAC DNA was isolated by the common alkali lysis method, and resuspended in 10 µL of TE. One microliter of recovered DNA was re-transformed back into E. coli cells (BAC cells, Intact Genomics).

Fungal Genomic DNA Extraction

Fungal DNA was extracted from lyophilized mycelia using previously described techniques (Bok, J. W. and Keller, N. P., Methods Mol. Biol., 2012, 944, 163-174) to perform PCR reaction.

Antimicrobial Screening

A disc-diffusion method (Bauer 1966) was used for antibiotic activity-guided screening. One plate of each A. nidulans FAC strain was inoculated on solid GMM and incubated for seven days at 37° C. Subsequently, the entire contents of the plates were collected and lyophilized for 48 hours. Samples were then pulverized with mortar and pestle prior to the addition of 10 mL of methanol. Air-dried methanol extracts were dissolved in 150 μL methanol for activity testing. Media preparation for antibacterial assays were performed as previously described (Bok, J. W. and Keller. N. P., Eukaryot. Cell, 2004, 3, 527-535). For antifungal assays, 10⁶ spores mentioned in the section above were embedded in 5 mL soft GMM agar (0.75% agar) and overlaid on solid GMM. 10 μL out of the 150 μL methanol extract above was loaded on a 1 cm diameter paper disc for each assay. Assay plates were incubated for 24 to 48 hour at 37° C. and observed for antimicrobial activity.

LC-HRMS Analysis

Five plates of *A. nidulans* FAC strain, for example and without limitation, AtFAC6J7 were inoculated on solid GMM and incubated for seven days at 37° C. Subsequently, the entire contents of the plates were collected and lyophilized for 48 hours. Samples were then pulverized with mortar and pestle prior to the addition of 10 mL of methanol. Air-dried methanol extracts were then further extracted with organic solvent (chloroform:methanol:ethylacetate=8:1:1). Organic extracts were evaporated to dryness and stored at −20° C. until analysis.

Organic extracts obtained were resuspended in methanol to a final concentration of 2 μg/μL. For each analysis, 40 μg of sample was loaded onto a LUNA® C18 column (150 mm×2 mm; 3 pun particle size) (Phenomenex, Torrance, Calif.). Chromatography was performed using an AGILENT® 1150 LC system (Agilent, Santa Clara, Calif.) at a flow rate of 200 μL/min. The following gradient was employed (Buffer A: water with 0.1% formic acid. Buffer B: acetonitrile with 0.1% formic acid): time 0 min, 2% B; 35 min, 70% B; 54 min, 98% B. A 1:7 split was employed post-column, resulting in a flow rate of 25 μL/min being directed to the mass spectrometer. A Q-EXACTIVE™ mass spectrometer (Thermo Fisher Scientific, Waltham, Mass.) was used for MS analysis with the following settings: capillary temperature 275° C., sheath gas 4 (arbitrary units), spray voltage 4.2 kV. Full MS spectra were acquired at 35,000 resolution for the mass range m/z 200 to 1500 for all samples. Following each full MS scan, the top 5 most intense ions were selected for a dependent MS2 scan. MS2 was conducted using higher-energy collisional dissociation (HCD) with a normalized collision energy of 30%. Three biological replicates of AtFAC6J7 extracts were prepared and analyzed in technical duplicate, followed by the data workup described below.

Data Analysis, Informatics, and Software

The SIEVE software suite (Thermo Fisher Scientific, Waltham, Mass.) was used for component detection and relative quantification of ions produced by electrospray during small molecule LC-HRMS. Component detection was performed using a mass tolerance of 10 part-per-million (ppm) and a retention time window of 2.5 min. A minimum intensity of 5×10⁶ was selected as the threshold for defining a peak as a component. For each component, a selected ion chromatogram was created and the integrated intensity of the peak was calculated. Peak areas were normalized based on total ion current. To increase statistical power and confidence of the final analysis, the procedure adopted here involved a decoy approach to multiple hypothesis testing. Specifically, the replicate data AtFAC6J7 was subjected to a uniqueness filter against processed LC-HRMS data generated from a control group of strains containing empty vectors, as well as 13 other strains containing a variety of other FACs with unique genetic content. For dereplication, all components were initially searched against a targeted accurate mass database consisting of known fungal metabolites produced by *A. nidulans* using a mass tolerance of 3 ppm. A dozen of these known compounds were present at consistent levels in nearly all samples, and were monitored to rapidly identify highly perturbed systems. All components were also searched against a comprehensive accurate mass database consisting of over 13,000 known fungal secondary metabolites. This fungal database was prepared using Antibase (2011), Dictionary of Natural Products (2013), as well as additional fungal natural products found in the literature (Caboche et al. 2008; Andersen et al. 2013).

Vector General Descriptions

The BstXI Linker overhang is not complementary to itself, nor is the BstXI-cut vector (above). Upon ligation of the linker-ligated large DNA fragments and vector, the preferred ligation reaction product can be a circle containing one vector joined to one large DNA fragment via a single adapter at each end. This molecule may be transformed into host cells to produce a clone.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example describes pFAC plasmid, a vector of the present teachings that maintains extra-chromosomes in *A. nidulans*.

In the present teachings, a FAC vector (pFAC, FIG. 1A, SEQ ID NO: 7) is a BAC-based shuttle vector that can shuttle large DNA between *E. coli* and *A. nidulans* hosts. Several features are required for maintaining the plasmid in *E. coli*, including two *E. coli* origins of replication: oriS and oriV. The first replication origin, oriS, is derived from a low-copy F plasmid for BAC-based large DNA cloning and library construction. The second replication origin, oriV, is an inducible high-copy replication origin oriV, which can produce higher yield of large inserts when grown in *E. coli* containing a TrfA gene under the control of an arabinose promoter when they are grown on arabinose containing media. pFAC also contains a chloramphenicol-resistance gene (cat) for plasmid selection. For cloning purposes, the plasmid contains a large DNA cloning site comprising pair of BstXI sites designed next to each other in oppose orientations. When digested with BstXI, this configuration produces a pair of identical BstXI overhangs, that are not self-complimentary, but are complimentary to unique BstXI linkers. Therefore, the digested vector will not religate itself, nor will the linkers concatermerize easily. Two 1-SceI homing restriction sites were inserted flanking the BstXI cloning site in reverse orientations. These sites facilitate clean excision of the cloned large DNA fragment and exchange with pFACint cloning vector (see example 2).

pFAC also contains features required for use in *A. nidulans*. These include a third replication origin, AMA1, the autonomous maintenance in *Aspergillus* (AMA1, SEQ ID NO: 8). This sequence is required for maintaining large intact SM pathways as extra-chromosomal elements, or FACs. pFAC also contains a fungal selection marker gene, the orotidine-5'-phosphate decarboxylase gene (pyrG from *A. parasiticus*, SEQ ID NO: 9 & 10).

Example 2

This example describes pFACint, a FAC integration vector.

FAC integration vector (pFACint, FIG. B, SEQ ID NO: 11) is a BAC-based shuttle BAC vector that can shuttle large DNA between *E. coli* and *A. nidulans* hosts. Several features are required for maintaining the plasmid in *E. coli*, including two *E. coli* origins of replication: oriS and oriV. The first replication origin, oriS, is derived from a low-copy F plasmid for BAC-based large DNA cloning and library construction. The second replication origin, oriV, is an inducible high-copy replication origin oriV, which can produce higher yield of large inserts when grown in *E. coli* containing a TrfA gene under the control of an arabinose promoter when they are grown on arabinose containing media. pFACint carries kanamycin-resistance gene (kan) as a selection marker gene, or cloning purposes, the plasmid contains a large DNA cloning site comprising pair of BstXI sites designed next to each other in oppose orientations. When digested with BstXI, this configuration produces a pair of identical BstXI overhangs, that are not self-complimentary, but are complimentary to unique BstXI linkers. Therefore, the digested vector will not religate itself, nor will the linkers concatermerize easily. Two 1-SceI homing restriction sites were inserted flanking the BstXI cloning site in reverse orientations. These sites facilitate clean excision of the cloned large DNA fragment and exchange with pFAC cloning vector. The I-Sce-I homing restriction sites also facilitate clean excision of the large intact SM gene pathways from the genomic integration site of the heterologous host *A. nidulans*.

pFACint also contains features integrating the plasmid into the *A. nidulans* genome: 1,000-bp 3'trpC (SEQ ID NO: 12) and 1,007-bp 5'trpC (SEQ ID NO: 13) homologous sequences, which were inserted flanking the I-Sce I restriction sites in the same orientations, thus enabling fungal site-specific integration of large pFACint clones into the *A. nidulans* trpC gene, which encodes a polypeptide homologous to polyketide. The plasmid also contains a fungal selection marker gene, the orotidine-5'-phosphate decarboxylase gene (pyrG, from *A. parasiticus*).

Example 3

This example describes the vector pFACdual.

pFACdual plasmid, which also substantially corresponds pFAC plasmid except that it includes an additional gene cassette: an attP site and a fungal codon-optimized phi31 integrase gene under the control of fungal inducible promoter, such as alcA(p). Therefore, the large DNA pFACdual clones are usually maintaining as FAC and also be able integrated into the fungal genome with an attB site whenever it is needed.

pFACdual vector is a fungal dual-function vector (pFACdual, FIG. 1C, SEQ ID NO: 14), and can act as both a fungal artificial chromosome and an inducible fungal genomic integration vector, or it can be used as an *E. coli*-*A. nidulans* shuttle BAC vector. pFACdual has similar features as pFAC (see Example 1), but pFAC dual has an additional gene cassette: an attP site and a fungal codon-optimized phi31 integrase gene (SEQ II) NO: 16 and SEQ ID NO: 17) under the control of the inducible alcA fungal promoter (alcA(p), SEQ ID NO: 15). Therefore, the large DNA pFACdual clones are usually maintained as a FAC but can be induced to integrated into the fungal genome with an attB site.

Example 4

This example illustrates the preparation of high molecular weight *A. wentii* DNA.

Figures 2A, 2B:
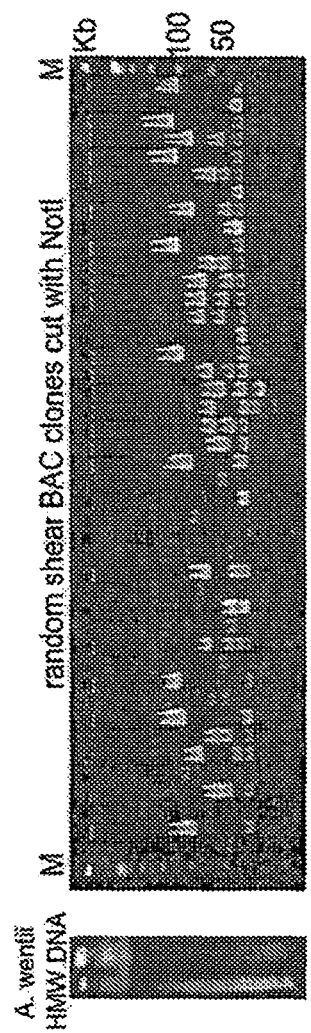
FIG. 2A-B illustrate preparation of HMW genomic DNA from *Aspergillus wentii* and random shear FAC cloning results.

*Aspergillus* wentii strain DTO 134E9 was used as a proof of concept. Different fungal species/strain starting materials were compared to test for quality of high molecular weight (HMW) genomic DNA: spores, germinated spores, protoplasts, or nuclei obtained from protoplasts. The protoplast preparation method was performed as previously described (Bok, J. W. and Keller, N. P., Eukaryot. Cell, 2004, 3: 527-535). To isolate nuclei, protoplasts were lysed with 0.5% Triton X-100 in HMW DNA preparation buffer (0.5 M Sucrose, 80 mM KCl, 10 mM Tris, 10 mM EDTA, 1 mM spermidine, 1 mM spermine, pH 9.4). The protoplasts in buffer were gently mixed, incubated on ice for 30 minutes, and the resulting nuclei pelleted at 1,800×g for 20 minutes. To prepare low melting agarose plugs of HMW DNA, the pellet ($\sim 5 \times 10^8$)—of nuclei, protoplasts, germinated spores, or spores—was resuspended with the HMW DNA preparation buffer to a total volume of 0.6 mL, and an equal volume of 1% low melting agarose was then added to the buffer to a total volume of 1.2 mL at 45° C. This was sufficient to make 10 plugs (about 100 μL per plug) which solidified at 4° C. The plugs were then incubated at 50° C. for 48 hours in 1 mL lysis buffer/plug: 0.5 M EDTA, pH 9.0, 1% lauryl sarcosine, 1 mg/mL proteinase K. Finally, the plugs were extensively washed in 10-20 volumes of the following buffers for one hour for each wash: once with buffer 1 (0.5 M EDTA, pH 9.0-9.3 at 50° C.), once with buffer 2 (0.05 M EDTA, pH 8.0 on ice), three times with buffer 3 (ice cold TE plus 0.1 mM phenylmethyl sulfonyl fluoride (PMSF) on ice), three times with buffer 4 (ice cold 11 on ice) and finally all plugs were stored in TE at 4° C. In order to estimate the size and yield of the extracted DNA, plugs were assessed using pulsed field gel electrophoresis (PFGE) (Bio-Rad CHEF Mapper, Hercules, Calif.). The final quality check conditions for the HMW genomic DNA were 6 V/cm, 10 sec to 1 min switch time for 12-16 hours at 14° C. by PFGE, along with appropriate HMW size markers (Zhang, M. et al., Nat. Protoc., 2012, 7, 467-478). The highest quality and quantity of HMW genomic DNA was obtained from the protoplast preparation (FIG. 2A). FIG. 2A shows a CHEF gel that contains *A. wentii* HMW genomic DNA ranging from greater than 50 kb but mainly Mb sizes of DNA fragments.

Example 5

This example illustrates the construction of unbiased shuttle BAC library of *A. wentii* DNA.

The HMW genomic DNA obtained from the protoplast preparation in Example 2 ranged from 50~>1,000 kb (mainly megabase sized fragments). The HMW DNA from three plugs was end-repaired with the DNA end repair enzyme kit (Intact Genomics) in a total volume of 500 μL with 10 μL of the end repair enzymes which were then heat inactivated (70° C., 15 min). The resulting DNA was ligated with BstXI adaptors (10 μL of 100 μM each) and 10 μL ligase (2 U/μL, Intact Genomics) in a total volume of 700 μL. Gel-fractionated DNA fragments ranging from 100 to 200 kb were purified by PFGE. Purified large DNA fragments (about 100 μL 1-3 ng/μL) were ligated into the cloning ready BAC BstXI shuttle vector (pFAC) at 16° C. for ~18 hours. Next, the ligated DNA mixture was electroporated into electroporation competent *E. coli* cells (BAC cells, Intact Genomics). Small-scale ligations and transformations (1 µL DNA per 20 µL cells) were used to judge the cloning efficiency. The insert sizes of about 50 BAC clones were determined and confirmed to include inserts of about 100 kb using CHEF gel electrophoresis and NotI digestion of random selected BAC clones in pFAC vector. FIG. 2B illustrates that the average insert size was estimated at ~100 kb (M, Lambda ladder Marker). Once the suitability of the ligated DNA was confirmed, large-scale ligations and transformations were conducted to achieve at least 7,680 clones for colony picking (20×384-well plates) for the unbiased shuttle BAC library.

Example 6

This example illustrates BAC/FAC end sequencing, and select SM cluster-containing candidate FAC clones.

BAC-end sequences of 1,536 clones from the unbiased Random Shear FAC library of *A. wentii* were completed by the Sanger BigDye sequencing method. The software Phred was used for base calling and sequence trimming. Vector masking was achieved using the DNAStar SeqMan Pro software package. The BAC end sequences were aligned against the *A. wentii* reference genome sequence by BLAST Assembled Genomes (NCBI). All 47 SM clusters-containing candidate FAC clones were successfully identified based on the FAC end sequence flanking one end of a SM cluster and the other FAC end sequence flanking the other end of the same SM cluster.

Example 7

This example illustrates construction of unbiased shuttle BAC library of *A. wentii* DNA and heterologous expression of SM clusters as FACs in *A. nidulans*.

*A. wentii* was used as an example for shuttle BAC DNA library construction, and it has a fully sequenced genome containing 47 annotated SM gene clusters (Cerqueira, G. C., et al., Nucleic Acids Res., 2013, 42 (Database issue), D705-D710). High molecular weight genomic DNA was prepared from *A. wentii* (see Example 4) and construction of the unbiased FAC library (see Example 5) resulted in ~20× genome coverage of the *A. wentii* genome, or a total of 7,680 FAC clones with an average insert size of 100 kb (FIG. 2A-B). The FAC library was arrayed into 384-well plates and both ends of 1,536 FAC clones were sequenced. Sequence alignment of these end sequences with the *A. wentii* reference genome was used to identify SM-BAC clones or candidate FACs containing all 47 SM gene clusters (Table 1). In addition, at least 10 of 56 SM clusters of *A. terreus* are located near telomeres and some telomeric sequences are still not complete in the whole genome sequence database. These data illustrate that these methods successfully overcome the potential bias against telomeric sequences in conventional BAC library construction through the introduction of randomly sheared genomic DNA into the FAC vectors.

Example 8

This example illustrates the validation of shuttle functions of FACs.

To date hundreds of FACs (ranging from 70 to 150 kb in size) were used for heterologous expression and analysis through transformation into *A. nidulans*. To validate the shuttle function of FACs, we also extracted five of the 15 FAC DNAs from transformed *A. nidulans* strains and successfully transformed FAC DNA back into *E. coli* (FIG. 3). *A. nidulans* was transformed with different FAC clones as determined by return of prototropy on medium without uracil and uridine. Forty or more colonies of *E. coli* each were then assessed from the recovery of the FACs in FIG. 3A-C respectively. The results show the recovery of FAC examples from all 3 *A. nidulans* transformants: AtFAC903 (~100 kb), AtFAC9A23 (~80 kb), and AtFAC7A10 (~90 kb) respectively. The 2nd and 3rd (D) lane(s) on the left hand side of the gels is the control FAC used to transform *A. nidulans*. All recovered FACs were digested with NotI, there is no obvious large mutation observed. M, Lambda ladder Marker. This was the first demonstration of the capability of AMA1 in supporting autonomous replication (FAC) of large DNA constructs at least 150 kb in *A. nidulans*. The present inventor and his collaborators the first to demonstrate that the FAC system allows for extrachromosomal replication of at least 150 kb in *A. nidulans* (Bok, J. W., et al. BMC Genomics, 2015, 16, 343).

Example 9

This example illustrates LC-HRMS linked FAC SM discovery.

For the initial identification and structure elucidation of SM compounds through FACs, *A. nidulans* AtFAC9D19 strain samples were prepared as described in the Methods section. *A. nidulans* AtFAC9D19 was found to produce the insecticide compounds: alantrypinone, serantrypinone, alantrypinene B, alantryleunone. *A. nidulans* AtFAC6J7 strain was also selected for initial proof-of-concept experiments, as it contained a cluster highly homologous to the recently characterized hexadehydroastechrome cluster in *A. fumigatus* (Yin, W. B., et al., ACS Synth. Biol., 2013, 2, 629-634,). AtFAC6J7 contains seven out of the eight genes found in the corresponding *A. fumigatus* cluster. The gene not present in this *A. terreus* cluster, hasG, encodes for an FAD binding protein responsible for converting a prenyl to a methylbutadienyl side chain to produce hexadehydroastechrome from astechrome. AtFAC6J7 metabolites were identified by analyzing organic extracts of the *A. nidulans* AtFAC6J7 transformant and control *A. nidulans* using LC-HRMS. Following data acquisition, Sieve software was used for component detection and relative quantitation (see Methods). When comparing AtFAC6J7 extracts to control sample extracts (wild type and other FAC strains), a compound that was present only in the AtFAC6J7 extract was identified as terezine D by both accurate mass (0.3 part-per-million error) and tandem mass spectrometry (MS/MS or MS2). Terezine D is a stable intermediate of astechrome biosynthesis (Watanabe, T., et al., Bioorg. Med. Chem., 2009, 17, 94-111; Bok, J. W., et al. BMC Genomics, 2015, 16, 343).

Example 10

This example illustrates an antibiotic activity test against FAC clones.

An antibiotic activity test was performed 14 FAC clones. Ten µl out of 150 µl methanol extract from FAC transformants cultured on GMM plate for 7 days at 37° C. were loaded on small disc (diameter: 1 cm) for antimicrobial activity test against *Aspergillus* spp., *Candida albicans*, *Bacillus cereus*, *Micrococcus luteus* and *Pseudomonas aeruginosa*. Antibiotic activity was observed against *Bacillus cereus* with two FAC extracts (Bok, J. W., et al. BMC Genomics, 2015, 16, 343).

Example 11

This example illustrates FAC recombineering and activating silent SM gene clusters.

Red/ET tools were used to elucidate the biosynthesis of benzomalvins from *A. terreus* FAC AtFAC9J20. Two smaller-size constructs (33.372 kb AtFAC9J20Δ#1 and 68.988 kb AtFAC9J20Δ#2) were created from the FAC clone AtFAC9J20 (102.715 kb) using the NIH BAC recombineering tool with the Red/ET homologous recombination. We also deleted 5 genes (AtFAC9J20ΔMtase, AtFAC9J20ΔNRPS1, AtFAC9J20ΔNRPS2, AtFAC9J20ΔNRPS3, and AtFAC9J20ΔPKS) in the benzomalvin cluster to obtain 5 additional FAC mutation constructs that helped to precisely elucidate biosynthetic pathway benzomalvin efficiently and effectively.

To activate a weakly expressed SM gene cluster in FAC AtFAC7O19, we have successfully inserted the fungal strong promoter gpdAp in front of the start codon 'ATG' of the transcription factor (TF) gene in this cluster. FAC recombineering was performed as a two step process. The inventor inserted the galK gene and selected Gal+ colonies on minimal media plus chloramphenicol and galactose and then replaced galK with the gpdA promoter by counter-selecting galK− colonies on minimal media plus chloramphicol, 2-deoxy-galactose, and glycerol. Eight out of eight trials produced FAC mutation constructs.

Fusion PCR was performed (FIG. 4A) to combine the selectable marker (e.g. KanR or galK gene) and a promoter (gpdA(p) or any genetic element) as one PCR product for FAC recombineering. The strong fungal promoter gpdAp was inserted in front of the ATG start codon of SM cluster genes in FAC AtFAC7019 with a kanamycin resistance gene. The Fusion PCR reactions are shown schematically in FIG. 4A (H1 and H2, homology sequences 1 and 2, respectively; cat, chloramphenicol acetyl transferase gene; FAC, origins of replication). For construction of the fusion PCR product of Kan gene and gpdA promoter, the primers used were: 38TF-Kan-leftendF (5'-TGGGACTTTGTCGCTCACGATTCGCCGAGTTGTATGGGCTGACCAGTGAC-cgacctgc agcctgttga-3', SEQ ID NO: 1) and Kan-leftendR (5'-GGTGCCCCAAGCCTTGGATCGTCCGTCGGAGGCT-GATCAGCGAgctc-3', SEQ ID NO: 2); gpdA-rightendF (5'-TCGCTGATCAGCCTCGACGGATCCAAGGC-TlGGGGCACCtgcgtt-3', SEQ ID NO: 3) and 38TF-gpdA-rightendR (5'-TCCTCATGAATTAGATGGTTAGATG-GACCTACCATCAGGATAGGTTCCATtgtgatgtc tgctcaagcggg-3', SEQ ID NO: 4). The result of the one-step targeting event is the insertion of constitutively active Kan-resistance gene next to gpdAp into a defined position on the FAC by selection on LB media with kanamycin and chloramphenicol for the maintenance of the engineered FAC. The fusion PCR insertions were confirmed with PCR followed by NotI restriction analysis of FAC DNA from 7 clones after the insertion of the kan-gpdAp selection cassettes, as shown in the gels in FIG. 4B. The first lane is unmodified FAC AtFAC7019 DNA, which was included as a control. All tested clones show the same pattern, had the intended insertion but no obvious mutation on the pulse field gel. M, Lambda ladder Marker. The bacteria are now phenotypically Kan+.

An example of recombineering using the modified RED/ET tools includes the deletion of 5 genes of AtFAC9J20 individually with the galK selection cassette. FIG. 5 shows the NotI restriction analysis of FAC miniprep DNA from 4 clones each were confirmed by PCR (M, Lambda ladder Marker). The second to last lane contains unmodified AtFAC9J20 DNA, which was included as a control. AtFAC9J20 contains 2 SM gene clusters. The five genes, all members of the same cluster, are 1.239-kb Mtase (dimethylallyltryptophan N-methyltransferase) gene, 3.334-kb NRPS1, 7.284-kb NRPS2, 7.815-kb NRPS3, and 7.741-kb PKS genes. Each set of 4 tested clones show the same pattern, and therefore had the intended deletion. No obvious mutations were detected by PCR, sequencing, or on the pulse field gel.

All engineered FACs were successfully transformed back into the *A. nidulans* host strain. Initially, heterologous expression of the intact FAC AtFAC9J20 identified a group of methylated NRPS products, which we successfully identified as belonging to benzomalvins family (benzomalvin A and benzomalvin E). Benzomalvin A is an indoleamine 2,3-dioxygenase (IDO) inhibitor with the potential of immune-therapy for cancer. With current FAC recombineering, we then observed a parallel 10,000-fold drop in signal of the NRPS products in the gene deletion mutants AtFAC9J20ΔNRPS1 and AtFAC9J20ΔNRPS2, which supports that these two NRPS are involved in the biosynthesis directly. We also observed accumulation of the expected biosynthetic precursors in our deletion mutants. In addition, accumulation of unmethylated intermediates in AtFAC9J20ΔMtase demonstrates identification of the methyl-transferase responsible for NRPS tailoring. In conclusion, we have established the biosynthesis of a known NRPS that has long eluded the field using the FAC technology and FAC deletants. These deletants not only allow us to see loss of their corresponding gene products, but also accumulation of biosynthetic precursors.

All cited references are incorporated by reference, each in its entirety. Applicant reserves the right to challenge any conclusions presented by the authors of any reference.

TABLE 1

Identified FAC clones covering intact SM gene clusters/pathways

| Fungal name | Cluster No. | FAC name | FAC Chromosome location | FAC size (bp) |
|---|---|---|---|---|
| A. wentii | 1 | 4O2 | 2:748867-861001 | 112,134 |
| A. wentii | 2 | 1K8 | 4:96694-210549 | 113,855 |
| A. wentii | 3 | 2F10 | 10:572788-655030 | 82,242 |
| A. wentii | 4 | 4E11 | 1:2038648-2143968 | 105,320 |
| A. wentii | 5 | 4L5 | 2:1829642-1920197 | 90,555 |
| A. wentii | 6 | 2P3 | 4:186740-312513 | 125,773 |
| A. wentii | 7 | 4I20 | 4:3165620-3255977 | 90,357 |
| A. wentii | 8 | 4D17 | 5:2466262-2562334 | 96,072 |
| A. wentii | 9 | 1H10 | 7:734062-839729 | 105,667 |
| A. wentii | 10 | 4D8 | 7:2270034-2350260 | 80,226 |
| A. wentii | 11 | 3M17 | 10:471140-562395 | 91,255 |
| A. wentii | 12 | 3A1 | 1:4161567-4254009 | 92,442 |
| A. wentii | 13 | 3D18 | 7:2189142-2288310 | 99,168 |
| A. wentii | 14 | 1C3 | 10:204841-294656 | 89,815 |
| A. wentii | 15 | 4A4 | 10:626528-706761 | 80,233 |
| A. wentii | 16 | 4H21 | 3:3886941-3984632 | 97,691 |
| A. wentii | 17 | 4H24 | 4:3696431-3796611 | 100,180 |
| A. wentii | 18 | 4F11 | 6:735456-839076 | 103,620 |
| A. wentii | 19 | 1H17 | 4:1-87455 | 87,454 |
| A. wentii | 20 | 2K17 | 1:3915914-4008958 | 93,044 |
| A. wentii | 21 | 2K14 | 2:47713-169410 | 121,697 |
| A. wentii | 22 | 3D13 | 4:1296201-1397275 | 101,074 |
| A. wentii | 23 | 3K2 | 6:2228078-2325930 | 97,852 |
| A. wentii | 24 | 3C22 | 8:121247-230196 | 108,949 |
| A. wentii | 25 | 3E24 | 8:318322-407365 | 89,043 |
| A. wentii | 26 | 3L2 | 9:672348-770093 | 97,745 |
| A. wentii | 27 | 3B4 | 9:1507369-1620289 | 112,920 |
| A. wentii | 28 | 3O22 | 5:115813-232664 | 116,851 |
| A. wentii | 29 | 4J7 | 2:84403-199331 | 114,928 |
| A. wentii | 30 | 2F2 | 2:2776606-2876645 | 100,039 |

TABLE 1-continued

Identified FAC clones covering intact SM gene clusters/pathways

| Fungal name | Cluster No. | FAC name | FAC Chromosome location | FAC size (bp) |
|---|---|---|---|---|
| A. wentii | 31 | 3D3 | 3:179174-288015 | 108,841 |
| A. wentii | 32 | 1B1 | 8:2015243-2105484 | 90,241 |
| A. wentii | 33 | 2B19 | 9:60968-155731 | 94,763 |
| A. wentii | 34 | 1C5 | 1:4290614-4374135 | 83,521 |
| A. wentii | 35 | 3B20 | 4:1742758-1828851 | 86,093 |
| A. wentii | 36 | 3M15 | 5:2345788-2464884 | 119,096 |
| A. wentii | 37 | 3L20 | 7:1356289-1462621 | 106,332 |
| A. wentii | 38 | 4H11 | 7:1563096-1662018 | 98,922 |
| A. wentii | 39 | 4F15 | 10:118366-207802 | 89,436 |
| A. wentii | 40 | 3H22 | 1:2934184-3041025 | 106,841 |
| A. wentii | 41 | 2I6 | 2:3977696-4074392 | 96,696 |
| A. wentii | 42 | 4D13 | 6:1689604-1829952 | 140,348 |
| A. wentii | 43 | 1J2 | 10:1-87900 | 87,899 |
| A. wentii | 44 | 4O4 | 2:2094226-2208140 | 113,914 |
| A. wentii | 45 | 2A12 | 1:241509-348838 | 107,329 |
| A. wentii | 46 | 2B23 | 5:4926109-5034905 | 108,796 |
| A. wentii | 47 | 4C1 | 4:1016467-1115739 | 99,272 |
| A. aculeatus | 1 | 4H17 | 13:812147-930096 | 117,949 |
| A. aculeatus | 2 | 4L4 | 1:1329301-1443690 | 114,389 |
| A. aculeatus | 3 | 5G11 | 11:918965-992874 | 73,909 |
| A. aculeatus | 4 | 10A5 | 4:1981-104478 | 102,497 |
| A. aculeatus | 5 | 1L24 | 3:256945-345686 | 88,741 |
| A. aculeatus | 6 | 4E3 | 3:1876432-1983658 | 107,226 |
| A. aculeatus | 7 | 2P8 | 4:870643-1011680 | 141,037 |
| A. aculeatus | 8 | 6P3 | 5:1830781-1950997 | 120,216 |
| A. aculeatus | 9 | 1K8 | 7:483343-596987 | 113,644 |
| A. aculeatus | 10 | 1E6 | 7:45-101465 | 101,420 |
| A. aculeatus | 11 | 2P10 | 8:211037-336059 | 125,022 |
| A. aculeatus | 12 | 10C21 | 8:1429400-1530871 | 101,471 |
| A. aculeatus | 13 | 2B9 | 9:86486-187588 | 101,102 |
| A. aculeatus | 14 | 2L14 | 11:315430-417137 | 101,707 |
| A. aculeatus | 15 | 4N8 | 11:404232-517227 | 112,995 |
| A. aculeatus | 16 | 2M19 | 15:923337-1012873 | 89,536 |
| A. aculeatus | 17 | 1M17 | 16:118922-222177 | 103,255 |
| A. aculeatus | 18 | 2K16 | 19:402235-497393 | 95,158 |
| A. aculeatus | 19 | 1J4 | 25:37-110883 | 110,846 |
| A. aculeatus | 20 | | | |
| A. aculeatus | 21 | 1D8 | 1:78626-186378 | 107,752 |
| A. aculeatus | 22 | 1D8 | 1:78626-186378 | 107,752 |
| A. aculeatus | 23 | 2N5 | 1:934347-1052021 | 117,674 |
| A. aculeatus | 24 | 6J24 | | |
| A. aculeatus | 25 | 2P10 | 8:211037-336059 | 125,022 |
| A. aculeatus | 26 | 4I23 | 9:285640-376987 | 91,347 |
| A. aculeatus | 27 | 1D4 | 9:1254796-1358882 | 104,086 |
| A. aculeatus | 28 | 1I21 | 11:392581-427849 | 35,268 |
| A. aculeatus | 29 | 3G18 | 13:521503-647022 | 125,519 |
| A. aculeatus | 30 | 6A16 | 16:18608-112106 | 93,498 |
| A. aculeatus | 31 | 4C19 | 23:290577-346496 | 55,919 |
| A. aculeatus | 32 | 8A16 | 1:2370038-2483583 | 113,545 |
| A. aculeatus | 33 | 4B9 | 3:31787-134936 | 103,149 |
| A. aculeatus | 34 | 10A5 | 4:1981-104478 | 102,497 |
| A. aculeatus | 35 | 10D7 | 5:13457-135109 | 121,652 |
| A. aculeatus | 36 | 1N19 | 5:540506-653619 | 113,113 |
| A. aculeatus | 37 | 4N5 | 11:505585-601756 | 96,171 |
| A. aculeatus | 38 | 1N17 | 17:406544-496393 | 89,849 |
| A. aculeatus | 39 | 1L21 | 18:355848-455803 | 99,955 |
| A. aculeatus | 40 | 3D12 | 22:235518-338083 | 102,565 |
| A. aculeatus | 41 | 2P8 | 4:870643-1011680 | 141,037 |
| A. aculeatus | 42 | 2H16 | 7:245753-358860 | 113,107 |
| A. aculeatus | 43 | 4G24 | 8:825803-930042 | 104,239 |
| A. aculeatus | 44 | 4N10 | 8:1046616-1187326 | 140,710 |
| A. aculeatus | 45 | 1A6 | 11:815776-909693 | 93,917 |
| A. aculeatus | 46 | 4P15 | 15:828019-921729 | 93,710 |
| A. aculeatus | 47 | | | |
| A. aculeatus | 48 | 3B14 | 16:743182-914054 | 170,872 |
| A. aculeatus | 49 | 2N10 | 19:21941-124962 | 103,021 |
| A. aculeatus | 50 | 3J24 | 19:179381-303639 | 124,258 |
| A. terreus | 1 | 4H7 | 1:341686-478144 | 136,458 |
| A. terreus | 1A | 10A3 | 1:780509-887159 | 106,650 |
| A. terreus | 2 | 9C14 | 1:596085-734818 | 138,733 |
| A. terreus | 3 | 4P7 | 1:846996-965042 | 118,046 |
| A. terreus | 4 | 3P14 | 1:1934917-2042485 | 107,568 |
| A. terreus | 5 | 7C11 | 1:2374190-2485502 | 111,312 |
| A. terreus | 6/7 | 6H10 | 1:2508820-2605929 | 97,109 |
| A. terreus | 7 | 8P6 | 2:37278-154428 | 117,150 |
| A. terreus | 8 | 5P8 | 2:175456-236080 | 60,624 |
| A. terreus | 9 | 5L9 | 2:2033593-2136987 | 103,394 |
| A. terreus | 10 | 6H11 | 3:7234-82997 | 75,763 |
| A. terreus | 11 | 4O12 | 3:1398587-1483241 | 84,654 |
| A. terreus | 12 | 8G17 | 3:1480896-1564240 | 83,344 |
| A. terreus | 13 | 5O9 | 4:98801-160061 | 61,260 |
| A. terreus | 14 | 8A13 | 4:420918-531892 | 110,974 |
| A. terreus | 15 | 9P15 | 4:791111-894250 | 103,139 |
| A. terreus | 15/16 | 9P15 | 4:791111-894250 | 103,139 |
| A. terreus | 16 | 9P15 | 4:791111-894250 | 103,139 |
| A. terreus | 17 | 3I8 | 4:1758828-1873324 | 114,496 |
| A. terreus | 18 | 6H12 | 4:1879158-1966492 | 87,334 |
| A. terreus | 19 | 8K17 | 4:2034110-2123632 | 89,522 |
| A. terreus | 20 | 9J20 | | |
| A. terreus | 21 | 4G11 | 5:133788-214705 | 80,917 |
| A. terreus | 22 | 10E11 | 5:1853747-1938725 | 102,692 |
| A. terreus | 23 | 9D19 | 6:159998-262690 | 102,692 |
| A. terreus | 24 | 10J22 | 6:1309309-1405640 | 96,331 |
| A. terreus | 25 | 9A23 | 7:69306-161456 | 92,150 |
| A. terreus | 25/26 | 9A23 | 26-7:69306-161456 | 92,150 |
| A. terreus | 26 | 6E22 | 7:115952-226883 | 110,931 |
| A. terreus | 27 | 4O15 | 7:389374-485106 | 95,732 |
| A. terreus | 28 | 3B22 | 8:378233-481460 | 103,227 |
| A. terreus | 29 | 3E2 | 8:1151835-1242603 | 95,425 |
| A. terreus | 30 | 9O3 | 8:1289965-1386325 | 96,360 |
| A. terreus | 31 | 9M17 | 8:1557569-1681014 | 123,445 |
| A. terreus | 32 | 2M16 | 9:37509-162692 | 125,183 |
| A. terreus | 33 | 6A19 | 9:1117011-1219649 | 102,638 |
| A. terreus | 34 | 1F7 | 9:1340453-1432992 | 92,539 |
| A. terreus | 35 | 9B9 | 10:388955-491178 | 102,223 |
| A. terreus | 36 | 9H19 | 10:590841-687211 | 96,370 |
| A. terreus | 37 | 4N23 | 10:1162818-1274448 | 111,630 |
| A. terreus | 38 | 7O19 | 10:1344783-1469927 | 125,144 |
| A. terreus | 39 | 5N15 | | 124,136 |
| A. terreus | 40 | 5L7 | 11:189737-313873 | |
| A. terreus | 41 | 6C13 | 11:591712-688498 | 96,786 |
| A. terreus | 42 | 10E15 | 11:1236080-1364157 | 128,077 |
| A. terreus | 43 | 6M16 | 12:499575-613644 | 114,069 |
| A. terreus | 44 | 6J7 | 12:1198845-1311006 | 112,161 |
| A. terreus | 44/45 | 6J7 | 12:1198845-1311006 | 112,161 |
| A. terreus | 45 | 6J7 | 12:1198845-1311006 | 112,161 |
| A. terreus | 46 | 5B9 | 13:398169-522253 | 124,084 |
| A. terreus | 47 | 8N10 | 13:400980-551101 | 150,121 |
| A. terreus | 48 | 5E10 | | |
| A. terreus | 49 | 6I22 | 14:10646-148251 | 137,605 |
| A. terreus | 50 | 7P13 | 14:102696-205536 | 102,840 |
| A. terreus | 51 | 7M4 | 14:179105-281612 | 102,507 |
| A. terreus | 52 | 8J19 | 14:332563-448705 | 116,142 |
| A. terreus | 53 | 6N3 | 15:324192-439862 | 115,670 |
| A. terreus | 54 | 3F4 | | |
| A. terreus | 55 | 9F18 | 16:293433-427730 | 134,297 |
| A. terreus | 56 | 7A10 | 17:146565-258022 | 111,457 |
| A. terreus | Terpene 1 | 6M13 | 1:1386583-1533388 | 146,805 |
| A. terreus | Terpene 2 | 9E17 | 6:455951-563970 | 108,019 |
| A. terreus | Terpene 3 | 9C13 | 12:88904-236514 | 147,610 |
| A. terreus | Terpene 4 | 3D22 | 12:523665-644377 | 120,712 |
| F. solani | 1 | 2E3 | 10:497417-625418 | 128,001 |
| F. solani | 2 | | | |
| F. solani | 3 | 3F14 | 7:2665228-2777004 | 111,776 |
| F. solani | 4 | 2O10 | 11:1324838-1472596 | 147,758 |
| F. solani | 5 | 4I22 | 3:4484998-4590707 | 105,709 |
| F. solani | 6 | 1J3 | 1:5947166-6058440 | 111,274 |
| F. solani | 7 | 2C9 | 1:6048796-6187694 | 138,898 |
| F. solani | 8 | 1C22 | 2:78648-189964 | 111,316 |
| F. solani | 9 | 2B1 | 2:1222891-1338942 | 116,051 |
| F. solani | 10 | 3L2 | 3:4121819-4262348 | 140,529 |
| F. solani | 11 | 3G19 | 4:2935800-3094350 | 158,550 |
| F. solani | 12 | 2O18 | 6:121424-277323 | 155,899 |
| F. solani | 13 | 2O18 | 6:121424-277323 | 155,899 |

TABLE 1-continued

Identified FAC clones covering intact SM gene clusters/pathways

| Fungal name | Cluster No. | FAC name | FAC Chromosome location | FAC size (bp) |
|---|---|---|---|---|
| F. solani | 14 | 10F21 | | |
| F. solani | 15 | | | |
| F. solani | 16 | 3E2 | 4:3834997-3969332 | 134,335 |
| F. solani | 17 | 3A18 | 7:1303685-1388079 | 843,94 |
| F. solani | 18 | 1E22 | 12:379009-512802 | 133,793 |
| F. solani | 19 | 2F18 | 3:4443819-4582383 | 138,564 |
| F. solani | 20 | 2L11 | 7:1936340-2050559 | 114,219 |
| F. solani | 21 | 2E21 | 11:1902682-2059573 | 156,891 |
| F. solani | 22 | 3N11 | 3:1629540-1770525 | 140,985 |
| P. expansum | 1 | 1C1 | 2:312817-450926 | 138,109 |
| P. expansum | 2 | | | |
| P. expansum | 3 | | | |
| P. expansum | 4 | 1I8 | 4:1247013-1372677 | 125,664 |
| P. expansum | 5 | 3F5 | 1:1428409-1585340 | 156,931 |
| P. expansum | 6 | | | |
| P. expansum | 7 | 1E10 | 6:2472012-2613808 | 141,796 |
| P. expansum | 8 | 3H13 | 1:91057-206469 | 115,412 |
| P. expansum | 9 | 1M17 | 2:2757993-2859810 | 101,817 |
| P. expansum | 10 | | | |
| P. expansum | 11 | 4J16 | 3:5156008-5276692 | 120,684 |
| P. expansum | 12 | 1F14 | 1:2595162-2676961 | 81,799 |
| P. expansum | 13 | 4L5 | 3:2479260-2593440 | 114,180 |
| P. expansum | 14 | 1I20 | 5:2892354-2942520 | 50,166 |
| P. expansum | 15 | 1D1 | 7:1213497-1276116 | 62,619 |
| P. expansum | 16 | 1A5 | 7:1772082-1843010 | 70,928 |
| P. expansum | 17 | 3M24 | 1:3415171-3497903 | 82,732 |
| P. expansum | 18 | 4K17 | 1:5004361-5150993 | 146,632 |
| P. expansum | 19 | 1C22 | 2:439256-579636 | 140,380 |
| P. expansum | 20 | 3L8 | 2:568926-619210 | 50,284 |
| P. expansum | 21 | 1I13 | 2:1939195-2068600 | 129,405 |
| P. expansum | 22 | 3E9 | 2:2550509-2673774 | 123,265 |
| P. expansum | 23 | 3L12 | 2:4051128-4199147 | 148,019 |
| P. expansum | 24 | 1D10 | 2:4697659-4828152 | 130,493 |
| P. expansum | 25 | 1C20 | 3:1422179-1537964 | 115,785 |
| P. expansum | 26 | 1F1 | 4:2105296-2219587 | 114,291 |
| P. expansum | 27 | 3K18 | 4:2396436-2517370 | 120,934 |
| P. expansum | 28 | | | |
| P. expansum | 29 | 4B6 | 4:4151706-4258120 | 106,414 |
| P. expansum | 30 | 1H7 | 5:724830-858181 | 133,351 |
| P. expansum | 31 | 3D20 | 5:2516815-2595970 | 79,155 |
| P. expansum | 32 | 1H19 | 5:3059991-3198248 | 138,257 |
| P. expansum | 33 | 4F11 | 6:680725-789653 | 108,928 |
| P. expansum | 34 | 4C4 | 6:2985678-3103152 | 117,474 |
| P. expansum | 35 | 1J1 | 7:1033873-1087766 | 53,893 |
| P. expansum | 36 | 1B3 | 7:1609591-1770767 | 161,176 |
| P. expansum | 37 | 1F15 | 2:3978538-4117151 | 138,613 |
| P. expansum | 38 | 2M3 | | |
| P. expansum | 39 | 4N19 | 151:25308 | |
| P. expansum | 40 | 1D4 | 2:165990-301959 | 135,969 |
| P. expansum | 41 | 1M17 | 2:2757993-2859810 | 101,817 |
| P. expansum | 42 | 1L13 | 1:308889-439300 | 130,411 |
| P. expansum | 43 | 3O7 | 1:5834693-5974698 | 140,005 |
| P. expansum | 44 | 1L7 | 1:5930187-6058354 | 128,167 |
| P. expansum | 45 | | | |
| P. expansum | 46 | 3O24 | 232:16292 | |
| P. expansum | 47 | 4G22 | 6:1472288-1616429 | 144,141 |
| P. expansum | 48 | 3O17 | 6:104113-216326 | 112,213 |
| P. expansum | 49 | 1I16 | 5:3575401-3696790 | 121,389 |
| P. expansum | 50 | | | |
| P. expansum | 51 | 4N1 | 5:109164 | |
| P. expansum | 52 | 1E11 | 4:1187046-1321378 | 134,332 |
| P. expansum | 53 | 1K17 | 1:1048988-1183651 | 134,663 |
| P. expansum | 54 | 3P1 | 1:5444486-5562376 | 117,890 |
| P. expansum | 55 | 3A22 | 1:6038144-6166932 | 128,788 |
| P. expansum | 56 | 3D24 | 2:4386733-4544595 | 157,862 |
| P. expansum | 57 | 4F17 | 4:3681331-3802040 | 120,709 |
| P. marneffei | 1 | 3J15 | 67:225170-125073 | 100,097 |
| P. marneffei | 2 | 2P11 | 67:404440-310929 | 93,511 |
| P. marneffei | 3 | 1P3 | 67:677233-567875 | 109,358 |
| P. marneffei | 4 | 4N6 | | |
| P. marneffei | 5 | 3K12 | | |
| P. marneffei | 6 | 1G19 | 68:315035-218073 | 96,962 |
| P. marneffei | 7 | 2P24 | 68:1558104-1459036 | 99,068 |
| P. marneffei | 8 | 3N18 | 61:373927-285735 | 88,192 |
| P. marneffei | 9 | 2A16 | 61:1391144-1286901 | 104,243 |
| P. marneffei | 10 | 2P19 | 61:1648049-1517595 | 130,454 |
| P. marneffei | 11 | 1A23 | 61:3962211-3875027 | 87,184 |
| P. marneffei | 12 | 1L1 | 61:4455251-4326752 | 128,499 |
| P. marneffei | 13 | 1P2 | 61:4488722-4396086 | 92,636 |
| P. marneffei | 14 | 1E15 | 66:144375-42300 | 102,075 |
| P. marneffei | 15 | 1E18 | 66:1890203-1788064 | 102,139 |
| P. marneffei | 16 | 4N2 | | |
| P. marneffei | 17 | 1D7 | 65:2792272-2681919 | 110,353 |
| P. marneffei | 18 | 4J6 | | |
| P. marneffei | 19 | 1I10 | 62:312523-220000 | 92,523 |
| P. marneffei | 20 | 1B14 | 62:32547-232187 | 94,360 |
| P. marneffei | 21 | 1F17 | 62:534989-424038 | 110,951 |
| P. marneffei | 22 | 3M19 | 62:1367736-1247185 | 120,551 |
| P. marneffei | 23 | 2D2 | 62:1808172-1705473 | 102,699 |
| P. marneffei | 24 | 1K4 | 62:2312436-2214666 | 97,770 |
| P. marneffei | 25 | 4A13 | 62:2748106-2635778 | 112,328 |
| P. marneffei | 26 | 4L14 | 62:3766925-3684552 | 112,373 |
| P. marneffei | 27 | | | |
| P. marneffei | 28 | 2J1 | 63:339173-235695 | 103,478 |
| P. marneffei | 29 | 4J24 | 63:1382725-1309149 | 73,576 |
| P. marneffei | 30 | 2P4 | 63:3217298-3115266 | 102,032 |
| P. marneffei | 31 | 4E11 | 64:1546365-1430552 | 115,813 |
| P. marneffei | 32 | 1J20 | 64:2842771-2737719 | 105,052 |
| P. marneffei | 33 | 3D3 | 64:3147532-3049393 | 98,139 |
| P. marneffei | 34 | 1N18 | 64:3206127-3074195 | 131,932 |

Table 2 Modifications of 55 SM Gene Clusters

| FAC Label | FAC Full Name | Cluster # | Fungal ID | Deletion | Engineered Gene ID | gdpA promoter insertion | gpdA promoter insertion site |
|---|---|---|---|---|---|---|---|
| pmFAC7nrps | PmFAC7-2P24-2P24gpdAp | 7 | Pm | | PMAA_01400 | yes | NRPS |
| pmFAC30TF | PmFAC30-2P4-2P4gpdAp | 30 | Pm | | PMAA_088090 | yes | TF |
| pmFAC23nrps | PmFAC23-2D2-2D2gpdAp | 23 | Pm | | PMAA_068360 | yes | NRPS |
| pmFAC19nrps | PmFAC19-1I10-1I10gpdAp | 19 | Pm | | PMAA_062600 | yes | NRPS |
| pmFAC13TF | PmFAC13-1P2-1P2gpdAp | 13 | Pm | | PMAA_031600 | yes | TF |
| pmFAC11TF | PmFAC11-1A23-1A23gpdAp | 11 | Pm | | PMAA_029860 | yes | TF |
| FsFAC19TF | FsFAC19-2F18-2F18gpdAp | 19 | Fs | | NECHADRAFT_78518 | yes | TF |

-continued

| FAC Label | FAC Full Name | Cluster # | Fungal ID | Deletion | Engineered Gene ID | gdpA promoter insersion | gpdA promoter insertion site |
|---|---|---|---|---|---|---|---|
| FsFAC7nrps | FsFAC7-2C9-NECHADRAFT_31971-gpdAp | 7 | Fs | | NECHADRAFT_31971 | yes | NRPS |
| FsFAC22pks | FsFAC22-3N11-NECHADRAFT_91827-gpdAp | 22 | Fs | | NECHADRAFT_91827 | yes | PKS |
| FsFAC14nrps | FsFAC14-10F21-NECHADRAFT_44426-gpdAp | 14 | Fs | | NECHADRAFT_44426 | yes | NRPS |
| AaFAC30 6A16Δnrps | AaFAC30-6A16-ΔAacu16872_046595 | 30 | Aa | yes | Aacu16872_046595 | | |
| AaFAC35 10D7Δpks | AaFAC35-10D7-ΔAacu16872_51108 | 35 | Aa | yes | Aacu16872_51108 | | |
| AaFAC39 1L21Δpks | AaFAC39-1L21-ΔAacu16872_054820 | 39 | Aa | yes | Aacu16872_054820 | | |
| AaFAC41 2P8Δnrps | AaFAC41-2P8-ΔAacu16872_058515 | 41 | Aa | yes | Aacu16872_058515 | | |
| AwFAC2-1K8Δ400 | AwFAC2-1K8-ΔAspwe1_0027400 | 2 | Aw | yes | Aspwe1_0027400 | | |
| AwFAC4-4E11Δ72 | AwFAC4-4E11-ΔAspwe1_0034272 | 4 | Aw | yes | Aspwe1_0034272 | | |
| AwFAC8-4D17Δ97 | AwFAC8-4D17-ΔAspwe1_0042597 | 8 | Aw | yes | Aspwe1_0042597 | | |
| AwFAC10-4D8Δ25 | AwFAC10-4D8-ΔAspwe1_0044725 | 10 | Aw | yes | Aspwe1_0044725 | | |
| AwFAC19-1H17Δ22 | AwFAC19-1H17-ΔAspwe1_0085322 | 19 | Aw | yes | Aspwe1_0085322 | | |
| AwFAC27-3B4Δ09 | AwFAC27-3B4-ΔAspwe1_0121409 | 27 | Aw | yes | Aspwe1_0121409 | | |
| AwFAC31-3D3Δ32 | AwFAC31-3D3-ΔAspwe1_0151732 | 31 | Aw | yes | Aspwe1_0151732 | | |
| AwFAC32-1B1Δ93 | AwFAC32-1B1-ΔAspwe1_0163793 | 32 | Aw | yes | Aspwe1_0163793 | | |
| AwFAC43-1J2Δ48 | AwFAC43-1J2-ΔAspwe1_0294248 | 43 | Aw | yes | Aspwe1_0294248 | | |
| AtFAC30-nrpsgpdA-p | AtFAC30-9O3-ATEG_06113-gpdAp | 30 | At | | ATEG_06113 | yes | NRPS |
| AtFAC35gpdA-p | AtFAC35-9B9-ATEG_06995-gpdAp | 35 | At | | ATEG_06995 | yes | TF |
| AtFAC46gpdA-p | AtFAC46-7J7-ATEG_08663-gpdAp | 48 | At | | ATEG_08663 | yes | TF |
| AtFAC36-9H19Δ7 | AtFAC36-9H19-ΔATEG_07067 | 36 | At | yes | ATEG_07067 | | |
| AtFAC39-5N15Δ80 | AtFAC39-5N15-ΔATEG_07380 | 39 | At | yes | ATEG_07380 | | |
| AtFAC40-5L7ΔPKS | AtFAC40-5L7-ΔATEG_07500 | 40 | At | yes | ATEG_07500 | | |
| AtFAC38gpdAp | AtFAC38-7O19-ATEG_07357-gpdAp | 38 | At | yes | ATEG_07357 | yes | TF |
| AtFAC38gpdaΔ63 | AtFAC38-7O19-ATEG_07357-gpdAp-ΔATEG_07363 | 38 | At | yes | ATEG_07363 | yes | TF |
| AtFAC38gpdaΔ62 | AtFAC38-7O19-ATEG_07357-gpdAp-ΔATEG_07362 | 38 | At | yes | ATEG_07362 | yes | TF |
| AtFAC38gpdaΔ61 | AtFAC38-7O19-ATEG_07357-gpdAp-ΔATEG_07361 | 38 | At | yes | ATEG_07361 | yes | TF |
| AtFAC38gpdaΔ60 | AtFAC38-7O19-ATEG_07357-gpdAp-ΔATEG_07360 | 38 | At | yes | ATEG_07360 | yes | TF |
| AtFAC38gpdaΔ59 | AtFAC38-7O19-ATEG_07357-gpdAp-ΔATEG_07359 | 38 | At | yes | ATEG_07359 | yes | TF |
| AtFAC38gpdaΔNRPS | AtFAC38-7O19-ATEG_07357-gpdAp-ΔATEG_07358 | 38 | At | yes | ATEG_07358 | yes | TF |
| AtFAC38gpdaΔ56 | AtFAC38-7O19-ATEG_07357-gpdAp-ΔATEG_07356 | 38 | At | yes | ATEG_07356 | yes | TF |
| AtFAC38gpdaΔ55 | AtFAC38-7O19-ATEG_07357-gpdAp-ΔATEG_07355 | 38 | At | yes | ATEG_07355 | yes | TF |
| AtFAC38gpdaΔ54 | AtFAC38-7O19-ATEG_07357-gpdAp-ΔATEG_07354 | 38 | At | yes | ATEG_07354 | yes | TF |
| AtFAC 20 Δ73 | AtFAC20-9J20-ΔATEG_03573 | 20 | At | yes | ATEG_03573 | | |
| AtFAC 20 Δ9 | AtFAC20-9J20-ΔATEG_03569 | 20 | At | yes | ATEG_03569 | | |
| AtFAC 20 ΔM | AtFAC20-9J20-ΔATEG_03568 | 20 | At | yes | ATEG_03568 | | Trans-isoprenyl diphosphate synthase, Isoprendoid C1 superfamily |
| AtFAC 20 ΔM2 | AtFAC20-9J20-ΔATEG_03567p | 20 | At | yes | ATEG_03567p | | Cytochrome P450 |
| AtFAC 20 ΔPKS | AtFAC20-9J20-ΔATEG_03575&ATEG_03574 | 20 | At | yes | ATEG_03575 and ATEG_03574 | | |
| AtFAC 20 ΔNRPS 3 | AtFAC20-9J20-ΔATEG_03576 | 20 | At | yes | ATEG_03576 | | |
| AtFAC 20 ΔOphio | AtFAC20-9J20-Δophio-entire region | 20 | At | yes | | | FAC20:7-33473 |
| AtFAC 20 ΔBenz | AtFAC20-9J20-Δbenz-entire region | 20 | At | yes | partial missing | | FAC20:33474-102556 |
| AtFAC 20 ΔMtase | AtFAC20-9J20-ΔbenX | 20 | At | yes | missing | | FAC20:90495-91733-(EasF) dimethylallyltryptophan N-methyltransferase |
| AtFAC 20 ΔNRPS 1 | AtFAC20-9J20ΔbenY | 20 | At | yes | missing | | FAC20:86362-89695-NRPS1 |
| AtFAC 20 ΔNRPS 2 | AtFAC20-9J20ΔbenZ | 20 | At | yes | missing | | FAC20:77576-84859-NRPS2 |
| AtFAC20 9J20benY | AtFAC20-9J20ΔbenY-TermC | 20 | At | yes | missing | | FAC20:88367-89741-NRPS1-Cterm |
| AtFAC20 9J20benZ | AtFAC20-9J20ΔbenZ-TermC | 20 | At | yes | missing | | FAC20:77529-78882-NRPS2-Cterm |

| FAC Label | FAC Full Name | Cluster # | Fungal ID | Deletion | Engineered Gene ID | gdpA promoter insertion | gpdA promoter insersion site |
|---|---|---|---|---|---|---|---|
| FAC20ΔPbenF/2R | AtFAC20-9J20ΔPbenF/2R-locus | 20 | At | yes | | | FAC20:33474-84859 |
| FAC20Δ2F/PbenR | AtFAC20-9J20-Δ2F/PbenR-locus | 20 | At | yes | | | FAC20:86362-102556 |
| FAC20ΔMtaseF/PKSR | AtFAC20-9J20-ΔMtaseF/PKSR-locus | 20 | At | yes | | | FAC20:50160-91733 |

What is claimed is:

1. A fungal artificial chromosome (FAC) comprising a bacterial artificial chromosome (BAC) vector comprising:
   a low-copy number bacterial origin of replication;
   an inducible high-copy number bacterial origin of replication;
   an *E. coli* selectable marker gene;
   an *Aspergillus* selectable marker gene; and
   an AMA1 filamentous fungal autonomous replicating element,
   wherein the FAC is a plasmid that replicates extrachromosomally in an *E. coli* host and in an *Aspergillus* fungal host.

2. A fungal artificial chromosome in accordance with claim 1, further comprising a pair of recognition sites in a head-to-head orientation for a restriction enzyme that generates non-complementary single-stranded overhangs upon digestion of the FAC.

3. A fungal artificial chromosome in accordance with claim 2, wherein the restriction enzyme that generates non-complementary single-stranded overhangs upon digestion of the FAC is selected from the group consisting of BstXI and I-SceI.

4. A fungal artificial chromosome in accordance with claim 1, wherein the low-copy number bacterial origin of replication is an oriS and the inducible high-copy number bacterial origin of replication is an oriV.

5. A fungal artificial chromosome in accordance with claim 1, wherein the *E. coli* selectable marker gene is selected from the group consisting of a chloramphenicol resistance gene (camR), kanR, ampR, genR, tetA, strepR, galK, and a combination thereof.

6. A fungal artificial chromosome in accordance with claim 1, wherein the *Aspergillus* selectable marker gene is selected from the group consisting of pyrG, ptrA, trpC, and a combination thereof.

7. A fungal artificial chromosome in accordance with claim 1, further comprising an insert of at least 20 kb.

8. A fungal artificial chromosome in accordance with claim 1, further comprising an insert of at least 100 kb.

9. A fungal artificial chromosome in accordance with claim 1, further comprising an insert comprising at least one secondary metabolite (SM) gene cluster.

10. A fungal artificial chromosome in accordance with claim 1, further comprising an integration site and an integrase gene.

11. An *Aspergillus* fungus comprising the fungal artificial chromosome of claim 1.

12. An *Aspergillus* fungus in accordance with claim 11, wherein the fungal artificial chromosome comprises at least one secondary metabolite (SM) gene cluster that is heterologous to the fungus.

13. A method of unbiased FAC library construction, comprising:
   providing high molecular weight (HMW) genomic DNA from a filamentous fungus;
   mechanically shearing the HMW genomic DNA into fragments of 100 kb-300 kb in length;
   generating blunt ends on the DNA fragments;
   ligating BstXI linkers to the blunt ends, thereby generating linker-ligated DNA fragments;
   purifying the linker-ligated DNA fragments by pulse field gel electrophoresis; and
   ligating the purified and linker-ligated DNA fragments into a BstXI-cut fungal artificial chromosome (FAC) of claim 1.

14. A method in accordance with claim 13, further comprising transforming a host microorganism with the ligated BstXI-cut FAC, wherein the host microorganism is an *E. coli*.

15. A method of inserting a DNA sequence into a targeted location in a secondary metabolite (SM) gene cluster, comprising:
   providing a fungal artificial chromosome (FAC) comprising a secondary metabolite (SM) gene cluster in accordance with claim 9;
   providing an insertion DNA comprising a) a first sequence homologous to a sequence flanking a first side of the targeted location, b) a sequence to be inserted, c) a second sequence homologous to a sequence flanking a second side of the targeted location and d) a bacterial selectable marker;
   transforming the FAC and the insertion DNA into an *E. coli* strain that expresses Red/ET recombinase enzymes; and
   selecting a transformed *E. coli* cell that comprises the bacterial selectable marker.

16. A method of deleting a targeted DNA sequence from a secondary metabolite (SM) gene cluster, comprising:
   providing a fungal artificial chromosome (FAC) comprising a secondary metabolite (SM) gene cluster in accordance with claim 9;
   providing a deletion DNA comprising a) a first sequence homologous to a sequence flanking a first side of the targeted DNA sequence, b) a second sequence homologous to a sequence flanking a second side of the targeted DNA sequence, and c) a bacterial selectable marker;
   transforming the FAC and the insertion DNA into an *E. coli* strain that expresses Red/ET recombinase enzymes; and
   selecting a transformed *E. coli* cell that comprises the bacterial selectable marker.

17. A fungal artificial chromosome in accordance with claim 1, wherein:
   the low-copy number bacterial origin of replication is an oriS;
   the inducible high-copy number bacterial origin of replication is an oriV;
   the *E. coli* selectable marker gene is selected from the group consisting of a chloramphenicol resistance gene (camR), kanR, ampR, genR, tetA, strepR, galK, and a combination thereof; and
   the *Aspergillus* selectable marker gene is selected from the group consisting of pyrG, ptrA, trpC, and a combination thereof.

18. A fungal artificial chromosome in accordance with claim 17, further comprising a pair of recognition sites in a head-to-head orientation for a restriction enzyme that generates non-complementary single-stranded overhangs upon digestion of the plasmid.

19. A fungal artificial chromosome comprising a nucleic acid sequence as set forth in SEQ ID NO:7, SEQ ID NO:11, or SEQ ID NO:14.

* * * * *